(12) United States Patent
Han et al.

(10) Patent No.: US 9,783,552 B2
(45) Date of Patent: Oct. 10, 2017

(54) SOLUBLE GUANYLATE CYCLASE ACTIVATORS

(71) Applicant: MERCK SHARP & DOHME CORP., Rahway, NJ (US)

(72) Inventors: Xiaoqing Han, Edison, NJ (US); Alan Whitehead, Scotch Plains, NJ (US); Subharekha Raghavan, Teaneck, NJ (US); Timothy A. Cernak, Boston, MA (US); Spencer Dreher, Metuchen, NJ (US); Jonathan Groeper, Indianapolis, IN (US); Jian Guo, Scotch Plains, NJ (US); Yong Zhang, West Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/103,148

(22) PCT Filed: Dec. 5, 2014

(86) PCT No.: PCT/US2014/068689
§ 371 (c)(1),
(2) Date: Jun. 9, 2016

(87) PCT Pub. No.: WO2015/088886
PCT Pub. Date: Jun. 18, 2015

(65) Prior Publication Data
US 2016/0304537 A1  Oct. 20, 2016

Related U.S. Application Data

(60) Provisional application No. 61/914,568, filed on Dec. 11, 2013.

(51) Int. Cl.
| | | |
|---|---|---|
| *C07D 519/00* | (2006.01) | |
| *A61K 31/519* | (2006.01) | |
| *A61K 31/52* | (2006.01) | |
| *A61K 45/06* | (2006.01) | |

(52) U.S. Cl.
CPC .......... *C07D 519/00* (2013.01); *A61K 31/519* (2013.01); *A61K 31/52* (2013.01); *A61K 45/06* (2013.01)

(58) Field of Classification Search
CPC .................................................. C07D 519/00
See application file for complete search history.

(56) References Cited

U.S. PATENT DOCUMENTS

| | | | |
|---|---|---|---|
| 3,211,732 A | 10/1965 | Schmidt et al. | |
| 5,977,118 A | 11/1999 | Bacon et al. | |
| 6,743,798 B1 | 6/2004 | Straub et al. | |
| 7,173,037 B2 | 2/2007 | Alonso-Alija et al. | |
| 8,420,656 B2 | 4/2013 | Follmann et al. | |
| 8,455,638 B2 | 6/2013 | Bittner et al. | |
| 8,507,512 B2 | 8/2013 | Kim et al. | |
| 8,741,910 B2 | 6/2014 | Brockunier et al. | |
| 8,859,569 B2 | 10/2014 | Follmann et al. | |
| 8,895,583 B2 | 11/2014 | Tan et al. | |
| 9,023,849 B2 | 5/2015 | Follmann et al. | |
| 9,090,610 B2 | 7/2015 | Follmann et al. | |

(Continued)

FOREIGN PATENT DOCUMENTS

| | | |
|---|---|---|
| WO | WO2012004258 | 1/2012 |
| WO | WO2015088885 A1 | 6/2015 |
| WO | WO2015187470 A1 | 12/2015 |

OTHER PUBLICATIONS

Follmann, N. et al., The Chemistry and Biology of Soluble Guanylate Cyclase Stimulators and Activators, Angewandte Chemie—International Edition, 2013, pp. 9442-9462, vol. 52 Issue 36.

(Continued)

*Primary Examiner* — Susanna Moore
(74) *Attorney, Agent, or Firm* — Eric A. Meade; Catherine D. Fitch

(57) ABSTRACT

A compound of Formula I or a pharmaceutically acceptable salt thereof, are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, or a pharmaceutically acceptable salt thereof, for their use in the therapy and prophylaxis of the abovementioned diseases and for preparing pharmaceuticals for this purpose, and to pharmaceutical preparations which comprise compounds of Formula I or a pharmaceutically acceptable salt thereof.

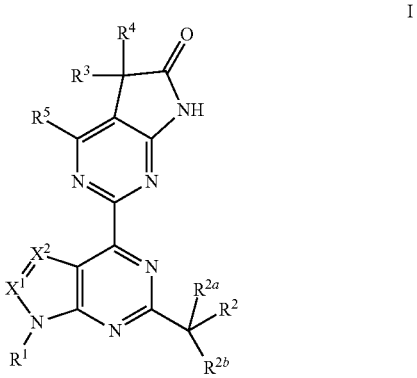

18 Claims, No Drawings

(56) References Cited

U.S. PATENT DOCUMENTS

| | | |
|---|---|---|
| 9,216,978 B2 | 12/2015 | Follmann et al. |
| 9,284,301 B2 | 3/2016 | Schmidt et al. |
| 9,365,574 B2 | 6/2016 | Raghavan et al. |
| 2011/0172216 A1 | 7/2011 | Dotson et al. |
| 2013/0072492 A1 | 3/2013 | Raghavan et al. |
| 2014/0171434 A1 | 6/2014 | Follmann et al. |
| 2014/0228366 A1 | 8/2014 | Follmann et al. |
| 2014/0357637 A1 | 12/2014 | Follmann et al. |
| 2016/0145272 A1 | 5/2016 | Berger et al. |

OTHER PUBLICATIONS

International Search Report and Written Opinion for PCT/US2014/068689, mailed Mar. 11, 2015, 11 pages.

SOLUBLE GUANYLATE CYCLASE ACTIVATORS

CROSS-REFERENCE TO RELATED APPLICATIONS

This application is a U.S. National Phase application under 35 U.S.C. §371 of PCT/US2014/068689, filed Dec. 5, 2014, which claims priority from U.S. provisional application No. 61/914,568 filed Dec. 11, 2013.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are composed of an α and a β subunit each. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore suitable for the therapy and prophylaxis of disorders which are associated with a low cGMP level.

SUMMARY OF THE INVENTION

The present invention relates to compounds which activate soluble guanylate cyclase and are valuable pharmaceutically active compounds for the therapy and prophylaxis of diseases, for example for cardiovascular diseases such as hypertension, heart failure, pulmonary hypertension, angina pectoris, diabetes, cardiac insufficiency, thrombosis, chronic kidney disease or atherosclerosis. The compounds of Formula I

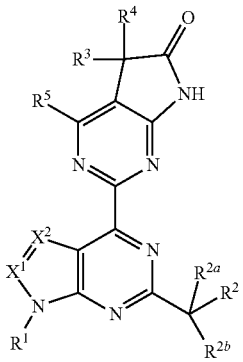

are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of Formula I, to their use for the therapy and prophylaxis of the abovementioned diseases and for preparing pharmaceuticals for this purpose, and to pharmaceutical preparations which comprise compounds of Formula I.

DETAILED DESCRIPTION OF THE INVENTION

The present invention is directed to compounds having structural Formula I:

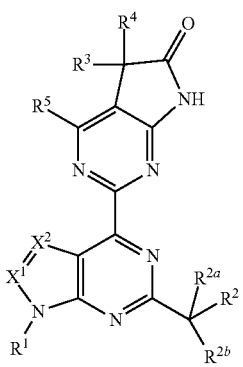

or a pharmaceutically acceptable salt thereof wherein:
$X^1$ and $X^2$ are each independently CR or N;
R is —H, halo or cyclopropyl;
$R^1$ is —H or —$C_{1-6}$alkyl unsubstituted or substituted with one to three of —F;
$R^2$ is (a) —$C_{1-6}$alkyl unsubstituted or substituted with
  (i) one to six of —F,
  (ii) —$C_{3-6}$cycloalkyl unsubstituted or substituted with one to three of —F or
  (iii) phenyl unsubstituted or independently substituted at each occurrence with one to three of halo, —CN, —$CH_3$ or —$OCH_3$,
(b) —$C_{3-6}$cycloalkyl unsubstituted or substituted with one to three of —F, or
(c) phenyl unsubstituted or independently substituted at each occurrence with one to three of halo, —CN, —$CH_3$ or —$OCH_3$;

$R^{2a}$ is —H or —$C_{1-3}$alkyl unsubstituted or substituted with one to three of —F;
$R^{2b}$ is —H or —$C_{1-3}$alkyl unsubstituted or substituted with one to three of —F;
or $R^{2b}$ is —H and $R^2$ and $R^{2a}$ are joined together with the carbon to which they are both attached to represent
  (a) —$C_{3-6}$cycloalkyl unsubstituted or substituted with one to three of —F, or
  (b) a 4 to 6 membered heterocycle comprised of carbons and one or two heteroatoms independently selected from N, O or S, wherein the heterocycle is unsubstituted or independently substituted at each occurrence with one to three of halo, —CN, —$CH_3$ or —$OCH_3$;
$R^3$ is —$C_{1-6}$alkyl or —$C_{3-6}$cycloalkyl;
$R^4$ is (a) —$C_{1-6}$alkyl,
  (b) —$OC_{1-6}$alkyl
  (c) —$C_{2-6}$alkynyl,
  (d) —$C_{3-6}$cycloalkyl,
  (e) —COO—$C_{1-6}$alkyl
  (f) —$NHR^a$,
  (g) —NH—C(O)—$R^a$,
  (h) —C(O)$NHR^a$,
  (i) —CN,
  (j) phenyl unsubstituted or substituted with one to three substituents independently selected at each occurrence from halo, —$C_{1-6}$alkyl, —$OC_{1-6}$alkyl, —OH or —CN; or
  (k) phenyl substituted with a 5 or 6 membered heteroaryl comprised of carbon atoms, one to three of N, and zero or one of O, wherein the heteroaryl is unsubstituted or substituted with —$C_{1-3}$alkyl;
$R^a$ is (a) —H, (b) —$C_{1-6}$alkyl unsubstituted or substituted with one or more substituents independently selected from —OH, one to three of —F,
  (c) —$C_{1-3}$alkyl-$C_{3-6}$cycloalkyl, (d) —$C_{3-6}$cycloalkyl, or
  (e) a 5 or 6 membered heteroaryl comprised of carbon atoms and one to three heteroatoms independently selected from N, O and S, wherein the heteroaryl is unsubstituted or substituted with —$C_{1-3}$alkyl;
$R^5$ is —H, —$OR^6$ or —$NHR^6$; and
$R^6$ is —H, —$C_{1-6}$alkyl or —$C_{3-6}$cycloalkyl.

In an embodiment of this invention, which is referred to herein as Embodiment 1, are compounds of Formula I wherein:
$X^1$ and $X^2$ are each independently CH or N,
$R^1$ is —H or —$C_{1-3}$alkyl;
$R^3$ is —$C_{1-6}$alkyl or —$C_{3-6}$cycloalkyl; and
$R^5$ is —H, —OH or —$NH_2$.

In another embodiment of this invention, which is referred to herein as Embodiment 2, are compounds of Formula I wherein:
$X^1$ and $X^2$ are each independently CH or N,
$R^1$ is —H or —$C_{1-3}$alkyl;
$R^2$ is (a) —$C_{1-6}$alkyl substituted with
  (i) one to six of —F,
  (ii) —$C_{3-6}$cycloalkyl substituted with one to three of —F, or
  (iii) phenyl substituted with one to three of —F,
(b) —$C_{3-6}$cycloalkyl substituted with one to three of —F, or
(c) phenyl substituted with one to three of —F;
$R^3$ is —$C_{1-6}$alkyl or —$C_{3-6}$cycloalkyl;
$R^4$ is (a) —$C_{1-6}$alkyl,
  (b) —$OC_{1-6}$alkyl
  (c) —$C_{2-3}$alkynyl and particularly —C≡CH,
  (d) —$C_{3-6}$cycloalkyl,
  (e) —COO—$C_{1-3}$alkyl, (f) —NHR$^a$,
(g) —NH—C(O)—R$^a$,
(h) —C(O)NHR$^a$,
(i) —CN,
(j) phenyl unsubstituted or substituted with one to three substituents independently selected at each occurrence from halo, —C$_{1-3}$alkyl, —OC$_{1-3}$alkyl, —OH or —CN; or
(k) phenyl substituted with a 5 or 6 membered heteroaryl comprised of carbon atoms, one to three of N, and zero or one of O, wherein the heteroaryl is unsubstituted or substituted with —C$_{1-3}$alkyl;

R$^a$ is (a) —H,
(b) —C$_{1-6}$alkyl unsubstituted or substituted with one or more substituents independently selected from —OH and one to three of —F,
(c) —C$_{1-3}$alkyl-C$_{3-6}$cycloalkyl,
(d) —C$_{3-6}$cycloalkyl, or
(e) 5 or 6 membered heteroaryl comprised of carbon atoms and one to three of N, wherein the heteroaryl is unsubstituted or substituted with —C$_{1-3}$alkyl; and R$^5$ is —H, —OH or —NH$_2$.

In another embodiment of this invention are compounds of Formula I, Embodiment 1 or Embodiment 2 having structural Formula Ia:

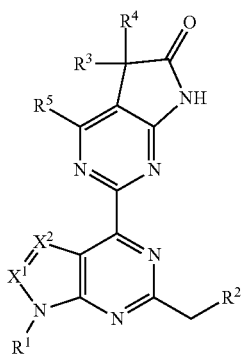

wherein all variables including R$^1$, R$^2$, R$^3$, R$^4$, R$^5$, X$^1$ and X$^2$ are as defined in Formula I.

In another embodiment of this invention are compounds of Formula I, Embodiment 1 or Embodiment 2 having structural Formula Ib:

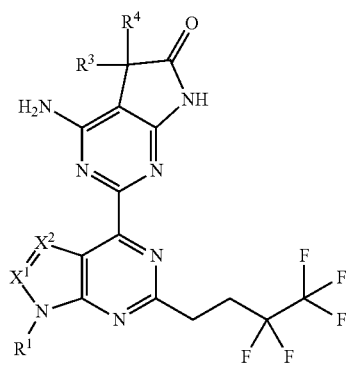

wherein all variables including R$^1$, R$^3$, R$^4$, X$^1$ and X$^2$ are as defined in Formula I.

In another embodiment of this invention are compounds of Formula I, Formula Ia, Formula Ib or Embodiment 1 wherein X$^1$ and X$^2$ are both N. In another embodiment, X$^1$ and X$^2$ are both CR in Formula I Formula Ia or Formula Ib; or X$^1$ and X$^2$ are both CH in Formula I, Formula Ia, Formula Ib, Embodiment 1 or Embodiment 2. In another embodiment, X$^1$ is N and X$^2$ is CR in Formula I, Formula Ia or Formula Ib; or X$^1$ is N and X$^2$ is CH in Formula I, Formula Ia, Formula Ib, Embodiment 1 or Embodiment 2.

In another embodiment of this invention are compounds of Formula I, Formula Ia, Formula Ib, Embodiment 1 or Embodiment 2 wherein R$^1$ is —H or —C$_{1-3}$alkyl unsubstituted or substituted with one to three of —F; particularly it is —H, —CH$_3$, —CD$_3$, —CH$_2$CH$_3$ or —CD$_2$CD$_3$; and more particularly it is —CH$_3$ or —CD$_3$.

In another embodiment of this invention are compounds of Formula I, Formula Ia or Embodiment 1 wherein R$^2$ is unsubstituted —C$_{1-6}$alkyl, unsubstituted —C$_{3-6}$cycloalkyl or unsubstituted phenyl.

In an alternate embodiment are compounds of Formula I, Embodiment 1 or Embodiment 2 wherein:
R$^2$ is (a) —C$_{1-6}$alkyl substituted with
(i) one to six of —F,
(ii) —C$_{3-6}$cycloalkyl substituted with one to three of —F, or
(iii) phenyl independently substituted at each occurrence with one to three of halo, —CN, —CH$_3$ or —OCH$_3$,
(b) —C$_{3-6}$cycloalkyl substituted with one to three of —F, or
(c) phenyl independently substituted at each occurrence with one to three of halo, —CN, —CH$_3$ or —OCH$_3$.

Particularly, R$^2$ can be —C$_{1-5}$alkyl-CF$_3$, —C$_{1-4}$alkyl-CF$_3$, —C$_{1-3}$alkyl-CF$_3$, or —C$_{1-2}$alkyl-CF$_3$, wherein each group is unsubstituted or substituted with one to three of —F on one or more available carbons. Alternatively, R$^2$ can be —C$_{3-6}$cycloalkyl or —C$_{1-3}$alkyl-C$_{3-6}$cycloalkyl wherein a carbon in the cycloalkyl ring is di-substituted with —F, for example but no limited to:

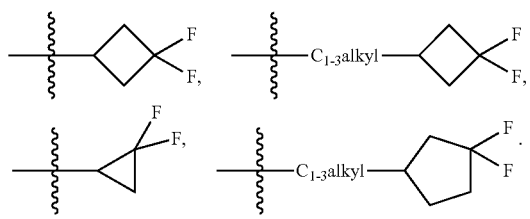

Alternatively, R$^2$ can be -phenyl or —C$_{1-3}$alkyl-phenyl, wherein each phenyl is substituted with one to three of —F.

In another embodiment of this invention are compounds of Formula I, Formula Ia, Formula Ib, Embodiment 1 or Embodiment 2 wherein R$^3$ is —C$_{1-6}$alkyl or —C$_{3-6}$cycloalkyl, and particularly it is —C$_{1-3}$alkyl or cyclopropyl.

In another embodiment of this invention are compounds of Formula I, Formula Ia, Formula Ib or Embodiment 1 wherein R$^4$ is
(a) —C$_{1-4}$alkyl,
(b) —OC$_{1-4}$alkyl, and particularly —OCH$_3$ or —OCD$_3$,
(c) —C$_{2-3}$alkynyl and particularly —C≡CH,
(d) —C$_{3-6}$cycloalkyl,
(e) —COO—C$_{1-3}$alkyl
(f) —NHR$^a$,
(g) —NH—C(O)—R$^a$,
(h) —C(O)NHR$^a$, (i) —CN,
(j) phenyl unsubstituted or substituted with one to three substituents independently selected at each occurrence from —F, —Cl, —Br, —$C_{1-3}$alkyl, —$OC_{1-3}$alkyl, —OH or —CN; or
(k) phenyl substituted with a 5 or 6 membered heteroaryl comprised of carbon atoms, one to three of N, and zero or one of O, wherein the heteroaryl is unsubstituted or substituted with —$C_{1-3}$alkyl; and particularly wherein the unsubstituted or substituted heteroaryl is pyridyl, oxadiazolyl or pyrazolyl.

In another embodiment of this invention are compounds of Formula I, Formula Ia, Formula Ib, Embodiment 1 or Embodiment 2 wherein $R^a$ is (a) —H, (b) —$C_{1-4}$alkyl unsubstituted or substituted with one or more substituents independently selected from —OH and one to three of —F, (c) —$C_{1-3}$alkyl-$C_{3-6}$cycloalkyl and particularly —$CH_2$—$C_{3-6}$cycloalkyl or —$CH_2$-cyclopropyl, (d) —$C_{3-6}$cycloalkyl and particularly cyclopropyl, or (e) a heteroaryl which is pyridyl or pyrazolyl, wherein the heteroaryl is unsubstituted or substituted with —$C_{1-3}$alkyl.

In another embodiment of this invention are compounds of Formula I, Formula Ia, Embodiment 1 or Embodiment 2 wherein $R^5$ is —H, —OH or —$NH_2$, or particularly it is —$NH_2$.

In another embodiment of this invention are each of the following compounds of Formula I, including the S and R enantiomers of such compounds, and the pharmaceutically acceptable salts of each said compound:

| EX | Compound Name |
|---|---|
| 1 | 4-Amino-5-methyl-2-(1-methyl-6-(3,3,4,4,4-pentafluorobutyl)-1H-pyrazolo[3,4-d]pyrimidin-4-yl)-5-phenyl-5H-pyrrolo[2,3-d]pyrimidin-6(7H)-one |
| 2 | 4-Amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 3 | 4-Amino-5-methyl-2-(1-methyl-6-(4,4,4-trifluorobutyl)-1H-pyrazolo[3,4-d]pyrimidin-4-yl)-5-phenyl-5H-pyrrolo[2,3-d]pyrimidin-6(7H)-one |
| 4 | 4-Amino-5-methyl-2-(1-methyl-6-(3,3,3-trifluoropropyl)-1H-pyrazolo[3,4-d]pyrimidin-4-yl)-5-phenyl-5H-pyrrolo[2,3-d]pyrimidin-6(7H)-one |
| 5 | 4-Amino-2-(6-((3,3-difluorocyclobutyl)methyl)-1-methyl-1H-pyrazolo[3,4-d]pyrimidin-4-yl)-5-(4-fluorophenyl)-5-methyl-5H-pyrrolo[2,3-d]pyrimidin-6(7H)-one |
| 6 | 4-Amino-2-(6-(2,3-difluorobenzyl)-1-methyl-1H-pyrazolo[3,4-d]pyrimidin-4-yl)-5-(4-fluorophenyl)-5-methyl-5H-pyrrolo[2,3-d]pyrimidin-6(7H)-one |
| 7 | 4-Amino-2-(1-ethyl-6-(3,3,4,4,4-pentafluorobutyl)-1H-pyrazolo[3,4-d]pyrimidin-4-yl)-5-methyl-5-phenyl-5H-pyrrolo[2,3-d]pyrimidin-6(7H)-one |
| 8 | 4-Amino-5-(4-fluorophenyl)-5-methyl-2-(6-(3,3,4,4,4-pentafluorobutyl)-1H-pyrazolo[3,4-d]pyrimidin-4-yl)-5H-pyrrolo[2,3-d]pyrimidin-6(7H)-one |
| 9 | 4-Amino-5-(4-fluorophenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 10 | 4-Amino-5-(4-bromophenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 11 | 4-Amino-5-(4-fluorophenyl)-5-methyl-2-(1-methyl-6-(3,3,3-trifluoropropyl)-1H-pyrazolo[3,4-d]pyrimidin-4-yl)-5H-pyrrolo[2,3-d]pyrimidin-6(7H)-one |
| 12 | 4-Amino-5,5-dimethyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 13 | 4-Amino-5-methyl-2-(6-(3,3,4,4,4-pentafluorobutyl)-1-trideuteriomethyl-1H-pyrazolo[3,4-d]pyrimidin-4-yl)-5-phenyl-5H-pyrrolo[2,3-d]pyrimidin-6(7H)-one |
| 14 | 4-Amino-5-(3-methoxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 15 | 4-Amino-5-(3-fluoro-4-methoxyphenyl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one |
| 16 | 4-Amino-5-(3-fluoro-4-methoxyphenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 17 | 4-Amino-5-cyclopropyl-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 18 | 4-Amino-5-cyclohexyl-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 19 | 4-Amino-2-(1-ethyl-6-(3,3,4,4,4-pentafluorobutyl)-1H-pyrazolo[3,4-d]pyrimidin-4-yl)-5-(4-fluorophenyl)-5-methyl-5H-pyrrolo[2,3-d]pyrimidin-6(7H)-one |
| 20 | 4-Amino-2-(1-ethyl-6-(4,4,4-trifluorobutyl)-1H-pyrazolo[3,4-d]pyrimidin-4-yl)-5-(4-fluorophenyl)-5-methyl-5H-pyrrolo[2,3-d]pyrimidin-6(7H)-one |
| 21 | 4-Amino-5-ethynyl-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 22 | 4-Amino-5-ethynyl-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 23 | 4-Amino-5-ethyl-5-ethynyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 24 | 4-Amino-5-cyclopropyl-5-ethynyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 25 | 4-Amino-5-butyl-5-cyclopropyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 26 | Ethyl 4-amino-5-cyclopropyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxylate |
| 27 | Ethyl 4-amino-5-cyclopropyl-2-(1-methyl-6-(4,4,4-trifluorobutyl)-1H-pyrazolo[3,4-d]pyrimidin-4-yl)-6-oxo-6,7-dihydro-5H-pyrrolo[2,3-d]pyrimidine-5-carboxylate |
| 28 | 4-Amino-N,5-dicyclopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 29 | 4-Amino-5-cyclopropyl-N-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |

-continued

| EX | Compound Name |
|---|---|
| 30 | 4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide |
| 31 | 4-Amino-N-cyclopropyl-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide |
| 32 | 4-Amino-N-cyclopropyl-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 33 | 4-Amino-N,5-dicyclopropyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide |
| 34 | 4-Amino-N-cyclopropyl-5-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 35 | 4-Amino-N-cyclopropyl-5-isopropyl-2-(6-(3,3,4,4,4-pentafluorobutyl)-1-trideuteriomethyl-1H-pyrazolo[3,4-d]pyrimidin-4-yl)-6-oxo-6,7-dihydro-5N-pyrrolo[2,3-d]pyrimidine-5-carboxamide |
| 36 | 4-Amino-5-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 37 | 4-Amino-5-isopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 38 | 4-Amino-N,5-dicyclopropyl-2-(1-ethyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide |
| 39 | 4-Amino-N-ethyl-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 40 | 4-Amino-N-cyclopropyl-2-(6-(2,3-difluorobenzyl)-1-methyl-1H-pyrazolo[3,4-d]pyrimidin-4-yl)-5-methyl-6-oxo-6,7-dihydro-5H-pyrrolo[2,3-d]pyrimidine-5-carboxamide |
| 41 | 4-Amino-5-cyclopropyl-2-(6-(3,3,4,4,4-pentafluorobutyl)-1-trideuteriomethyl-1H-pyrazolo[3,4-d]pyrimidin-4-yl)-6-oxo-N-(pyridin-2-yl)-6,7-dihydro-5H-pyrrolo[2,3-d]pyrimidine-5-carboxamide |
| 42 | 4-amino-5-methyl-N-(1-methyl-1H-pyrazol-4-yl)-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide |
| 43 | 4-Amino-5-(4-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 44 | 4-Amino-5-(3-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 45 | 5-(4-(1,3,4-Oxadiazol-2-yl)phenyl)-4-amino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 46 | 4-Amino-5-methyl-5-(4-(1-methyl-1H-pyrazol-4-yl)phenyl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 47 | 4-(4-Amino-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidin-5-yl)benzonitrile |
| 48 | 5-(4-Fluorophenyl)-4-hydroxy-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one |
| 49 | 4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carbonitrile |
| 50 | 4,5-Diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 51 | N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)picolinamide |
| 52 | N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)-2-cyclopropylacetamide |
| 53 | N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)cyclopropanecarboxamide |
| 54 | 4-Amino-5-((cyclopropylmethyl)amino)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 55 | 4-Amino-5-(isopropylamino)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 56 | 4-Amino-5-methoxy-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 57 | 4-Amino-5-methyl-5-trideuteriomethoxy-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one |
| 58 | 4-Amino-2-(3-chloro-1-methyl-6-(3,3,4,4,4-pentafluorobutyl)-1H-pyrazolo[3,4-d]pyrimidin-4-yl)-5-(4-fluorophenyl)-5-methyl-5H-pyrrolo[2,3-d]pyrimidin-6(7H)-one |
| 59 | 4-Amino-2-(3-cyclopropyl-6-(3,3,4,4,4-pentafluorobutyl)-1-trideuteriomethyl-1H-pyrazolo[3,4-d]pyrimidin-4-yl)-5-(4-fluorophenyl)-5-methyl-5H-pyrrolo[2,3-d]pyrimidin-6(7H)-one |
| 60 | 4-Amino-5-methyl-2'-(3,3,4,4,4-pentafluorobutyl)-5-phenyl-7'-trideuteriomethyl-5H,7'H-[2,4'-bipyrrolo[2,3-d]pyrimidin]-6(7H)-one |
| 61 | 4-Amino-5-(4-fluorophenyl)-5,7'-dimethyl-2'-(3,3,4,4,4-pentafluorobutyl)-5H,7'H-[2,4'-bipyrrolo[2,3-d]pyrimidin]-6(7H)-one |

| EX | Compound Name |
|---|---|
| 62 | 4-Amino-5,7'-dimethyl-2'-(3,3,4,4,4-pentafluorobutyl)-5-phenyl-5H,7'H-[2,4'-bipyrrolo[2,3-d]pyrimidin]-6(7H)-one |
| 63 | 4-Amino-5,5,7'-trimethyl-2'-(3,3,4,4,4-pentafluorobutyl)-5H,7'H-[2,4'-bipyrrolo[2,3-d]pyrimidin]-6(7H)-one |
| 64 | 4-Amino-2'-(2,3-difluorobenzyl)-5,7'-dimethyl-5-phenyl-5H,7'H-[2,4'-bipyrrolo[2,3-d]pyrimidin]-6(7H)-one |
| 65 | 4-Amino-5-methyl-2'-(3,3,4,4,4-pentafluorobutyl)-5-phenyl-5H,7'H-[2,4'-bipyrrolo[2,3-d]pyrimidin]-6(7H)-one |
| 66 | 4-Amino-2-(5-(2,3-difluorobenzyl)-3-methyl-3H-[1,2,3]triazolo[4,5-d]pyrimidin-7-yl)-5-(4-fluorophenyl)-5-methyl-5H-pyrrolo[2,3-d]pyrimidin-6(7H)-one |
| 67 | 4-Amino-5-(4-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one |
| 68 | 4-Amino-5-methyl-2-(5-(3,3,4,4,4-pentafluorobutyl-3-trideuteriomethyl)-3H-[1,2,3]triazolo[4,5-d]pyrimidin-7-yl)-5-phenyl-5H-pyrrolo[2,3-d]pyrimidin-6(7H)-one |
| 69 | 4-Amino-5-cyclopropyl-5-(4-fluorophenyl)-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one |
| 70 | 4-Amino-5-(4-chlorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one |
| 71 | 4-Amino-5-(4-methoxyphenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one |
| 72 | 4-Amino-5-(4-fluoro-3-methoxyphenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one |
| 73 | 4-Amino-5-(4-chloro-2-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one |

All structural Formulas, embodiments and classes thereof described herein include the pharmaceutically acceptable salts of the compounds defined therein. Reference to the compounds of structural Formula I includes the compounds of other generic structural Formulas and embodiments that fall within the scope of Formula I, including but not limited to Formula Ia, Formula Ib, and Embodiment 1 and Embodiment 2.

As used herein except where noted, "alkyl" is intended to include both branched- and straight-chain saturated aliphatic hydrocarbon groups having the specified number of carbon atoms when noted. Commonly used abbreviations for alkyl groups are used throughout the specification, e.g. methyl may be represented by conventional abbreviations including "Me" or $CH_3$ or a symbol that is an extended bond without a defined terminal group, e.g., a methyl substituent on phenyl may be represented as:

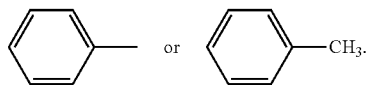

Ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. A phrase like or similar to "$C_{1-6}$ alkyl unsubstituted or substituted with 1-3 fluorine atoms" refers to alkyl groups having 0, 1, 2 or 3 fluorine atoms wherein each fluorine attached to one or more carbon atoms. The term "cycloalkyl" means a cyclized alkyl ring (i.e., a carbocycle) containing no heteroatoms. Examples of cycloalkyl include cyclopropyl, cyclobutyl, cyclopentyl, cyclohexyl, cycloheptyl, decahydronaphthyl and the like. In an embodiment, cycloalkyl is cyclopropyl or cyclobutyl, and particularly cyclopropyl.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "alkynyl" refers to a hydrocarbon radical straight or branched, containing the specified number of carbon atoms and at least one carbon to carbon triple bond. Alkynyl groups include ethynyl, propynyl, butynyl, 3-methylbutynyl and so on.

Alkyl, alkenyl, alkynyl and cycloalkyl are each intended to include such carbon moieties containing isotopic forms of hydrogen (H) such as protium ($^1$H), for example but not limited to —$CH_3$, and/or deuterium ($^2$H, also denoted herein as D), for example but not limited to —$CD_3$.

"Heteroaryl" unless otherwise indicated, means a mono- or bicyclic aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyrimidyl, pyridazinyl, pyrazinyl, and the like. Heteroaryl also includes a bicyclic ring system comprised of a mono-heteroaryl ring fused to a heterocyclic ring or a cycloalkyl ring. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium.

"Heterocyclyl," "heterocyclic," "heterocycle" or the like, unless otherwise indicated, means a 5- or 6-membered monocyclic non-aromatic or saturated ring containing at least one heteroatom selected from N, S and O, in which the point of attachment may be via an available carbon or nitrogen in the ring. Examples include, but are not limited to, pyrrolidinyl, piperidinyl, piperazinyl, morpholinyl, imidazolidinyl, 2,3-dihydrofuro(2,3-b)pyridyl, benzoxazinyl, oxetanyl, tetrahydrofuranyl or tetrahydropyranyl and the like. The terms also includes partially unsaturated monocyclic rings that are not aromatic, such as 2- or 4-pyridones attached through the nitrogen or N-substituted-(1H, 3H)-pyrimidine-2, 4-diones (N-substituted uracils). The terms also include such moieties in charged form, e.g., piperidinium.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., $R^1$, $R^2$, etc.) occurs more than one time in any constituent or in Formula I or other generic Formulae herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

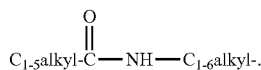

Unless expressly depicted or described otherwise, variables depicted in a structural formula with a "floating" bond are permitted on any available carbon atom in the ring to which the variable is attached. When a moiety is noted as being "optionally substituted" in Formula I or any embodiment thereof, it means that Formula I or the embodiment thereof encompasses compounds that contain the noted substituent (or substituents) on the moiety and also compounds that do not contain the noted substituent (or substituents) on the moiety.

Compounds of structural Formula I may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. The compounds of this invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formula I and embodiments thereof. For example, different isotopic forms of hydrogen (H) include protium (1H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts thereof. and also salts that are not pharmaceutically acceptable when they are used as precursors to the free compounds or their pharmaceutically acceptable salts or in other synthetic manipulations. The compounds of the present invention, including the compounds of the Examples, also includes all salts of the compounds of Formula I which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise.

The present invention also relates to processes for the preparation of the compounds of Formula I which are described in the following and by which the compounds of the invention are obtainable.

The compounds of Formula I according to the invention effect an increase of cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formula I can be examined, for example, in the activity assay described below.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. As an example, the dosage a patient receives can be selected so as to achieve the desired reduction in blood pressure; the dosage a patient receives may also be titrated over time in order to reach a target blood pressure. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Disorders and pathological conditions which are associated with a low cGMP level or in which an increase of the cGMP level is desired and for whose therapy and prophylaxis it is possible to use compounds of Formula I are, for example, cardiovascular diseases, such as endothelial dysfunction, diastolic dysfunction, atherosclerosis, hypertension, heart failure, pulmonary hypertension, which includes pulmonary arterial hypertension (PAH), stable and unstable angina pectoris, thrombosis, restenosis, myocardial infarction, strokes, cardiac insufficiency or pulmonary hypertonia, or, for example, erectile dysfunction, asthma bronchiale, chronic kidney disease and diabetes. Compounds of Formula I can additionally be used in the therapy of cirrhosis of the liver and also for improving a restricted memory performance or ability to learn.

The compounds of Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

A subject of the present invention therefore also are the compounds of Formula I and their pharmaceutically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component an effective dose of said compound and/or a pharmaceutically acceptable salt thereof and a customary pharmaceutically acceptable carrier, and the uses of said compound and/or a pharmaceutically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formula I and/or its pharmaceutically acceptable salts in the pharmaceutical preparations normally is from 0.2 to 200 mg, preferably from 1 to 200 mg, per dose, but depending on the type of the pharmaceutical preparation it can also be higher. The pharmaceutical preparations usually comprise 0.5 to 90 percent by weight of the compounds of Formula I and/or their pharmaceutically acceptable salts. The preparation of the pharmaceutical preparations can be carried out in a manner known per se. For this purpose, one or more compounds of Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results.

The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

The compounds of Formula I activate soluble guanylate cyclase. On account of this property, apart from use as pharmaceutically active compounds in human medicine and veterinary medicine, they can also be employed as a scientific tool or as an aid for biochemical investigations in which such an effect on soluble guanylate cyclase is intended, and also for diagnostic purposes, for example in the in vitro diagnosis of cell samples or tissue samples. The compounds of Formula I and salts thereof can furthermore be employed, as already mentioned above, as intermediates for the preparation of other pharmaceutically active compounds.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloroderivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, verapamil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®) and ezetimibe in combination with any other lipid lowering agents such as the HMG-CoA reductase inhibitors noted above and particularly with simvastatin (e.g., VYTORIN®) or with atorvastatin calcium (e.g. LIPTRUZET®); niacin in immediate-release or controlled release forms; niacin receptor agonists such as acipimox and acifran, as well as niacin receptor partial agonists; metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The "R" and "X" groups in the Schemes correspond to the variables defined in Formula I at the same positions on the structures. Compounds 2, 9 and 17a, which each have a —CH$_2$—R$^2$ moiety, are used for illustration purposes in Schemes 1, 4 and 5, but analogs of each compound having —CR$^{2a}$R$^{2b}$R$^2$ in place of —CH$_2$—R$^2$ can likewise be employed resulting in downstream intermediates and final products containing the corresponding —CR$^{2a}$R$^{2b}$R$^2$ moiety.

Compounds with structure 1 may be prepared by the sequence depicted in Scheme 1.

SCHEME 1

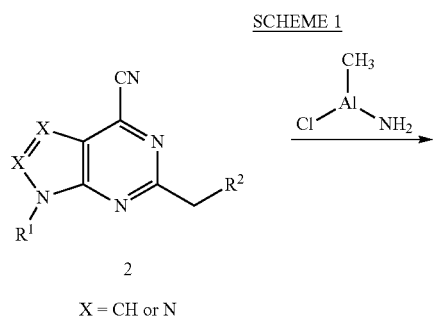

X = CH or N

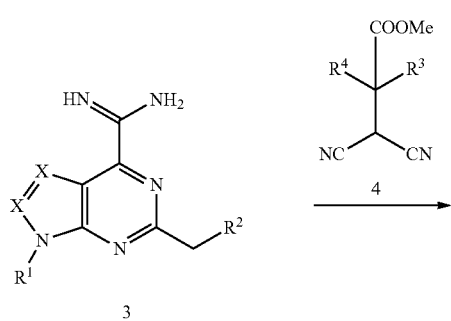

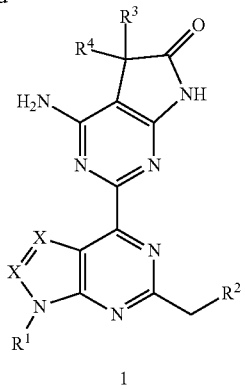

1

Conversion of the nitrile 2 to the amidine 3 can be accomplished with a reagent such as amino(chloro)methylaluminum, prepared from trimethylaluminum and ammonium chloride, in a non-polar solvent such as toluene at 100° C. as described by Garigipati, R. S. et al *Tetrahedron Letters* 1990, 31(14), 1969. The reaction may also be carried out on the corresponding methyl ester of compound 2. Reaction of compound 4 with the amidine 3 in an alcoholic solvent such as MeOH, n-BuOH or t-BuOH and a base such as NaOMe, NaOEt, t-BuOK, K$_2$CO$_3$ or NaHCO$_3$ at 90° C. to 150° C. affords the pyrimidine lactam 1. The reaction may also be carried out in the absence of a base. Additionally, the reaction may also be carried out on the corresponding ethyl or propyl ester of compound 4.

SCHEME 2

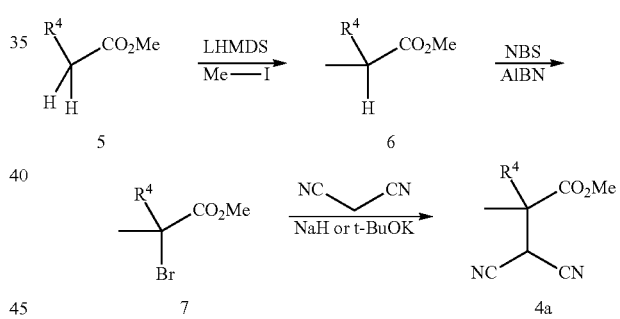

The preparation of compound 4a is outlined in Scheme 2. Deprotonation of ester 5 using a base such as LiHMDS, NaHMDS, NaH or LDA in a solvent such as THF or DMF followed by treatment with MeI affords the ester 6. The esters 5 and 6 may be prepared from the corresponding carboxylic acid by treatment with trimethylsilyl diazomethane or MeOH with catalytic sulfuric acid. The compound 7 is prepared by treating compound 6 with a brominating reagent such as NBS and AIBN in a solvent such as carbon tetrachloride at refluxing temperatures. Compound 4a, wherein R$^3$ is phenyl, methyl or an ester, is obtained from 7 by reaction with malononitrile and a base such as NaH, t-BuOK, K$_2$CO$_3$ or DBU in a solvent such as THF or DMF at ambient temperature to 100° C. The synthetic sequence depicted in Scheme 2 may also used to prepare the corresponding ethyl or propyl ester of compound 4a.

SCHEME 3

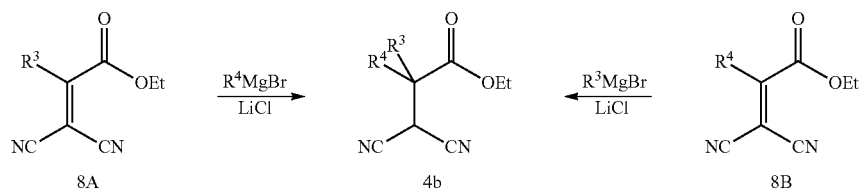

In addition to the methods described in Scheme 2, compound 4b (depicted as the ethyl ester) may also be prepared as shown in Scheme 3. Reaction of a suitable alkyl, or aryl magnesium halide with the dicyanopropenoate 8a (or 8b) and lithium chloride in a solvent such as THF affords compound 4b. Cycloalkyl and alkynyl magnesium halides are also suitable reagents for this reaction. Compound 8a ($R^3$ is $CO_2Et$) can be prepared using the procedure described by Sentman et. al. *J. Org. Chem.* 1982, 47, 4577. Compound 8b ($R^4$ is Me) can be prepared using the procedure described by Hagiware et. al. *Synthesis* 1974, 9, 669.

SCHEME 4

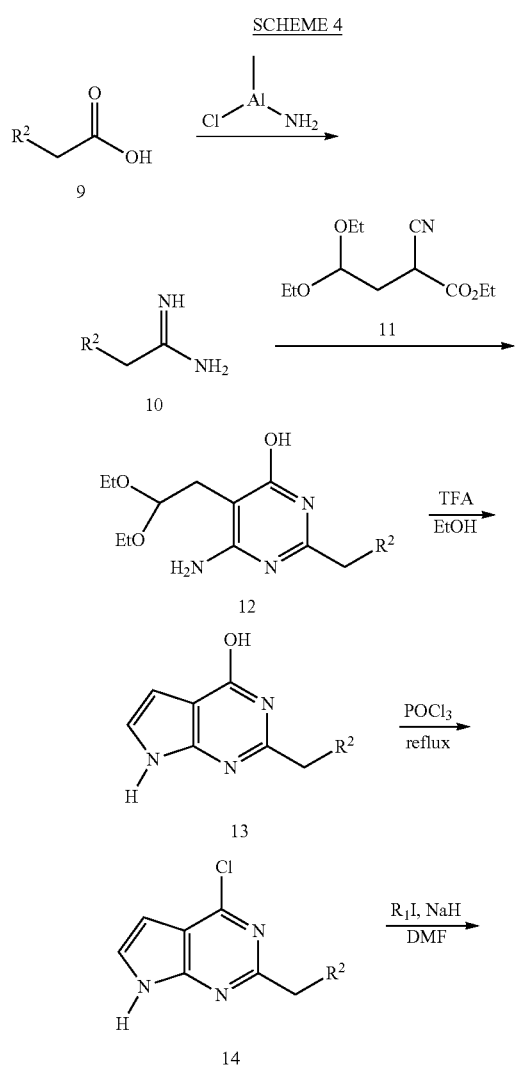

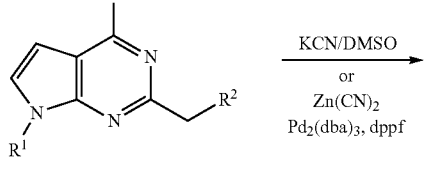

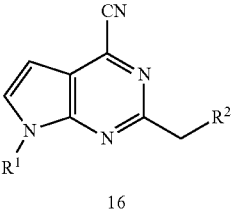

Compounds with structure 16 may be prepared by the sequence depicted in Scheme 4. Conversion of an appropriately substituted acid 9 to the amidine 10 can be accomplished with a reagent such as amino(chloro)methylaluminum, prepared from trimethylaluminum and ammonium chloride, in a non-polar solvent such as toluene. Treatment of 10 with ethyl 2-cyano-4,4-diethoxybutanoate (11) under refluxing conditions in an alcoholic solvent such as ethanol and suitable base such as sodium ethoxide affords the pyrimidine 12. De-protection of the acetal under standard conditions such as TFA in ethanol at RT affords 13 which can be converted to 14 by refluxing in $POCl_3$. Alkylation of the NH can be accomplished using a suitable alkyl or benzyl halide and a base such as NaH in a suitable solvent such as DMF to give 15. Finally, conversion of the chloride 15 to the nitrile 16 can be accomplished either by treatment of 15 with potassium cyanide in DMSO or treatment of 15 with zinc cyanide in the presence of a suitable catalyst such as $Pd_2(dba)_3$ and a ligand such as dppf in a polar solvent such a DMF.

SCHEME 5

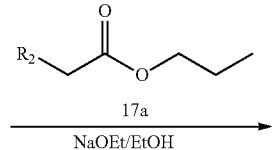

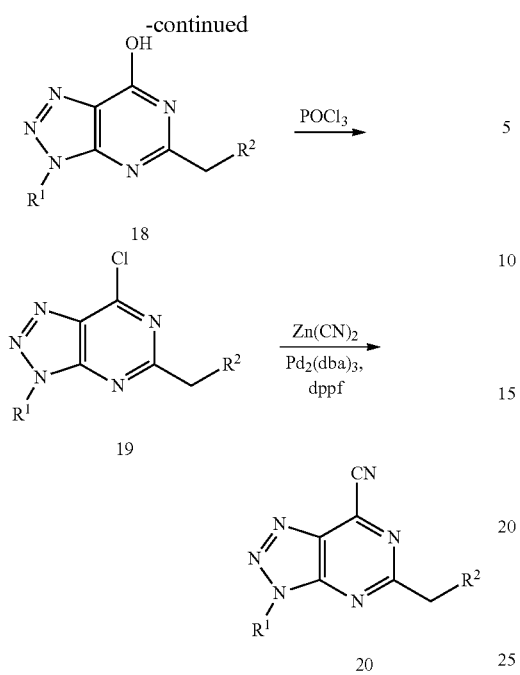

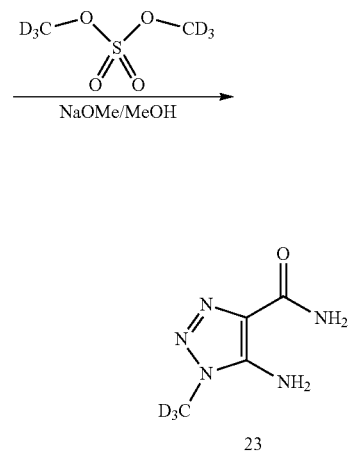

Compounds with structure 20 may be prepared by the sequence depicted in Scheme 5. Treatment of 17 with an appropriate propyl ester 17a and a suitable base such as NaOEt in an alcoholic solvent such as EtOH under refluxing conditions gives the cyclized product 18. This can be converted to the chloro compound 19 with phosphorous oxychloride either neat or in a chlorinated solvent such as DCE under refluxing conditions. The nitrile 20 can be prepared by treatment of the chloride 19 with zinc cyanide in the presence of a suitable catalyst such as $Pd_2(dba)_3$ and a ligand such as dppf in a polar solvent such a DMF.

accomplished with an alkylating agent such as dimethyl sulfate in the presence of a suitable base such as NaOMe in an alcoholic solvent such as MeOH to give 17 as a mixture of regioisomers.

Intermediate 22 can be converted to the deuterium intermediate 23 with dimethyl sulfate-$d_6$ using the methods described in scheme 6.

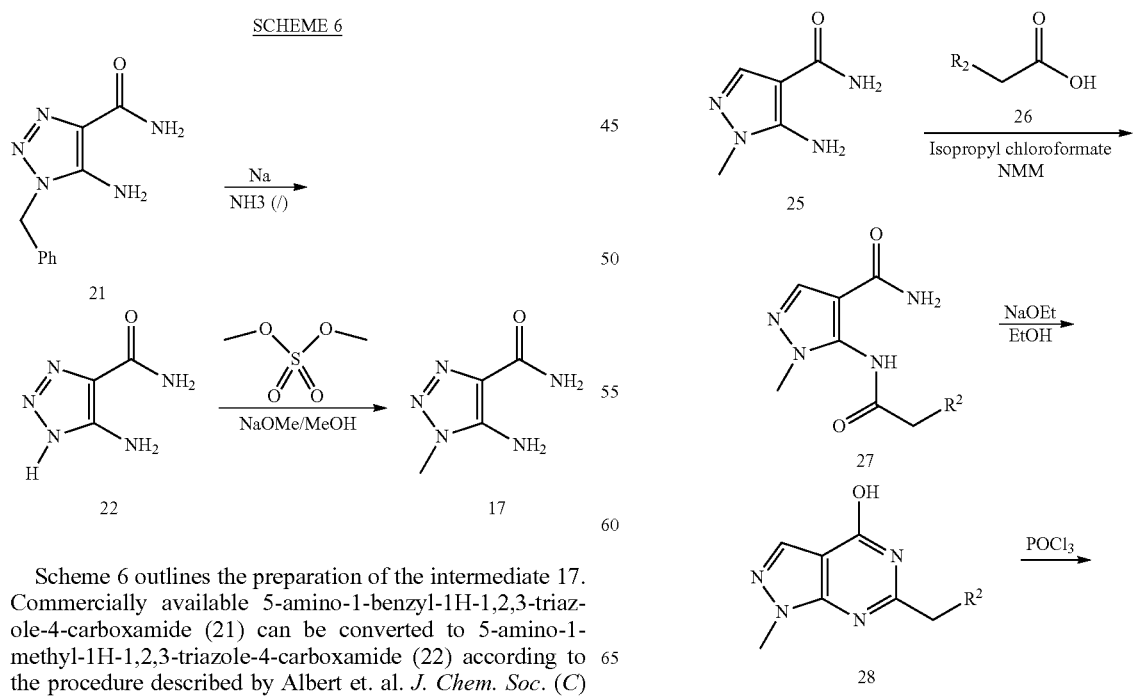

Scheme 6 outlines the preparation of the intermediate 17. Commercially available 5-amino-1-benzyl-1H-1,2,3-triazole-4-carboxamide (21) can be converted to 5-amino-1-methyl-1H-1,2,3-triazole-4-carboxamide (22) according to the procedure described by Albert et. al. *J. Chem. Soc. (C)* 1969, 9, 152. Installation of the methyl group can be -continued

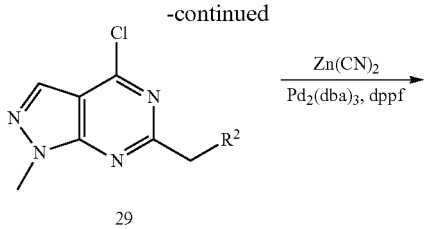

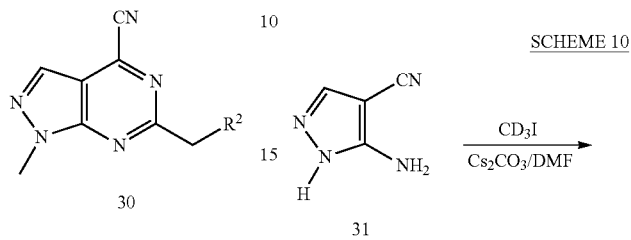

Compounds with structure 30 may be prepared by the sequence depicted in Scheme 8. Commercially available 5-amino-1-methyl-1H-pyrazole-4-carbonitrile (24) can be converted the amide 25 by treatment with concentrated sulfuric acid, which can be coupled to a suitable acid (26) in the presence of isopropyl chloroformate and a base such as N-methyl morpholine to afford 27. Treatment of 27 with a suitable base such as sodium ethoxide in an alcoholic solvent such as EtOH under refluxing conditions gives the cyclized product 28 which can be converted to 29 by refluxing in either neat POCl$_3$ or in a mixture of DCE and POCl$_3$. Finally, the nitrile 30 can be prepared by treatment of the chloride 29 with zinc cyanide in the presence of a suitable catalyst such as Pd$_2$(dba)$_3$ and a ligand such as dppf in a polar solvent such a DMF.

SCHEME 9

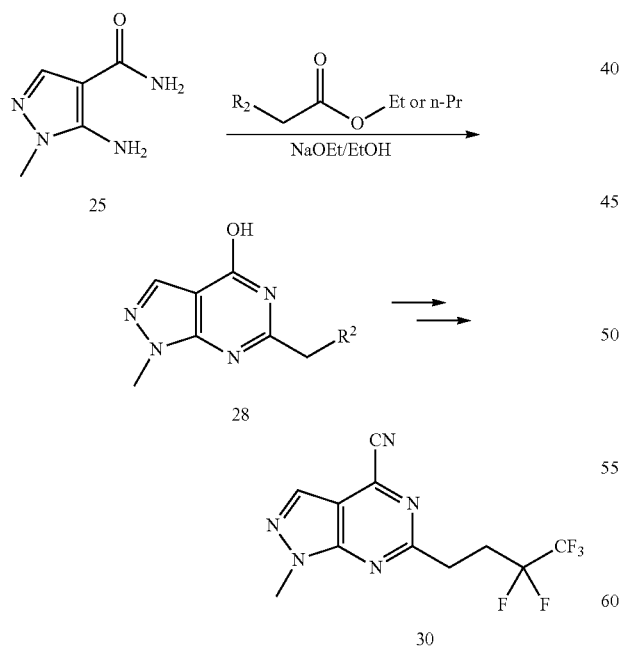

In addition to the methods described in Scheme 8, compound 28 may also be prepared as shown in Scheme 9. Treatment of 25 with an appropriate ethyl or propyl ester and a suitable base such as NaOEt in an alcoholic solvent such as ethanol under refluxing conditions gives the cyclized product 28, which can be elaborated to 30 using the procedures described in Scheme 8.

SCHEME 10

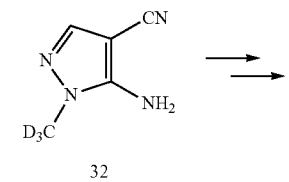

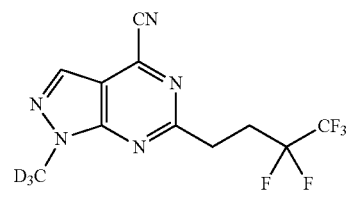

Compounds with structure 33 may be prepared by the sequence depicted in Scheme 10. Thus, treatment of commercially available 3-amino-1H-pyrazole-4-carbonitrile with a suitable base such as solid Cs$_2$CO$_3$ in a solvent such as DMF at 0° C. followed by the addition of iodomethane-d$_3$ at 0° C. to ambient temperature affords 32, which can be elaborated to 33 using the procedures described in Schemes 8 and 9.

SCHEME 11

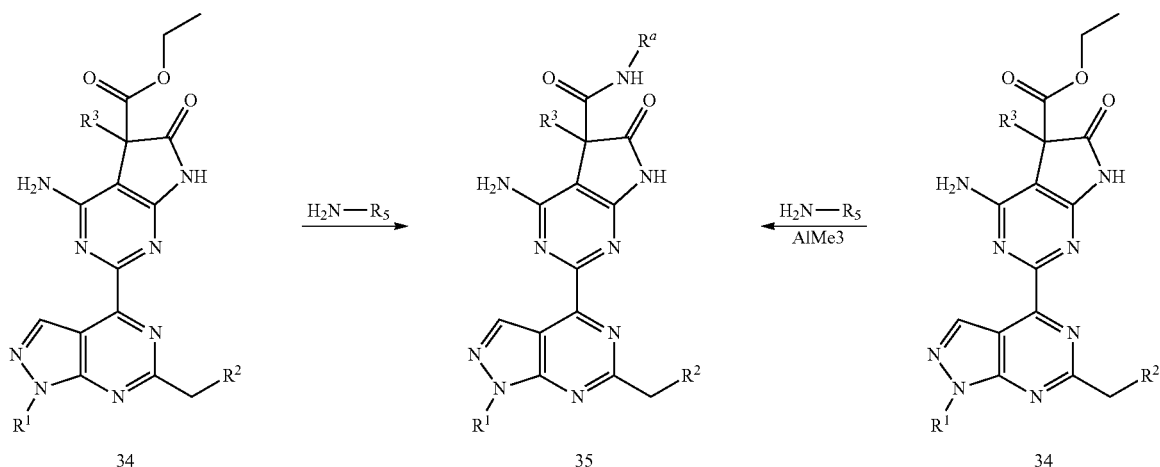

Compounds with structure 35 maybe prepared by the sequence as shown in Scheme 11. Structure 34 (depicted as the ethyl ester) can be formed analogous to the conversion of 3 to 1 as outlined in Scheme 1. Treatment of an intermediate of type 34 with ammonia and alkyl amine with or without a solvent such as THF and MeOH forms 35. In the case that heteroaryl amines are used, conversion of the ester 34 to the amidine 35 can be accomplished with a reagent prepared from trimethylaluminum and corresponding heteroarylamine in a non-polar solvent such as toluene at 80° C.

-continued

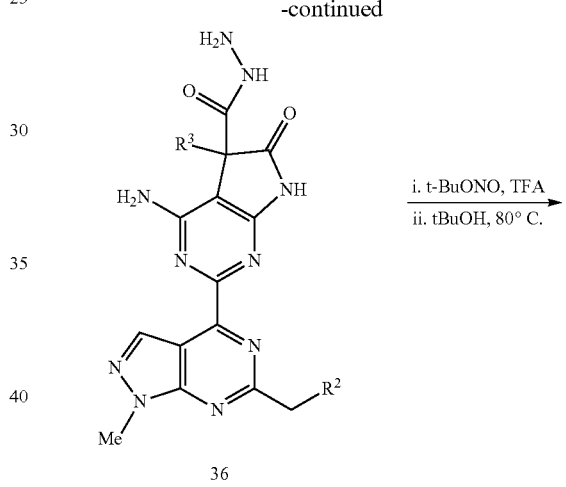

SCHEME 12

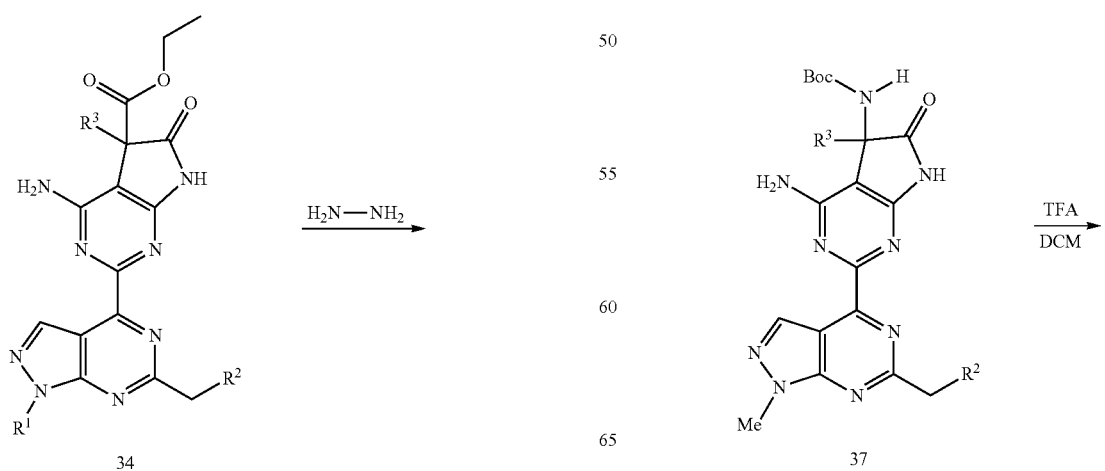

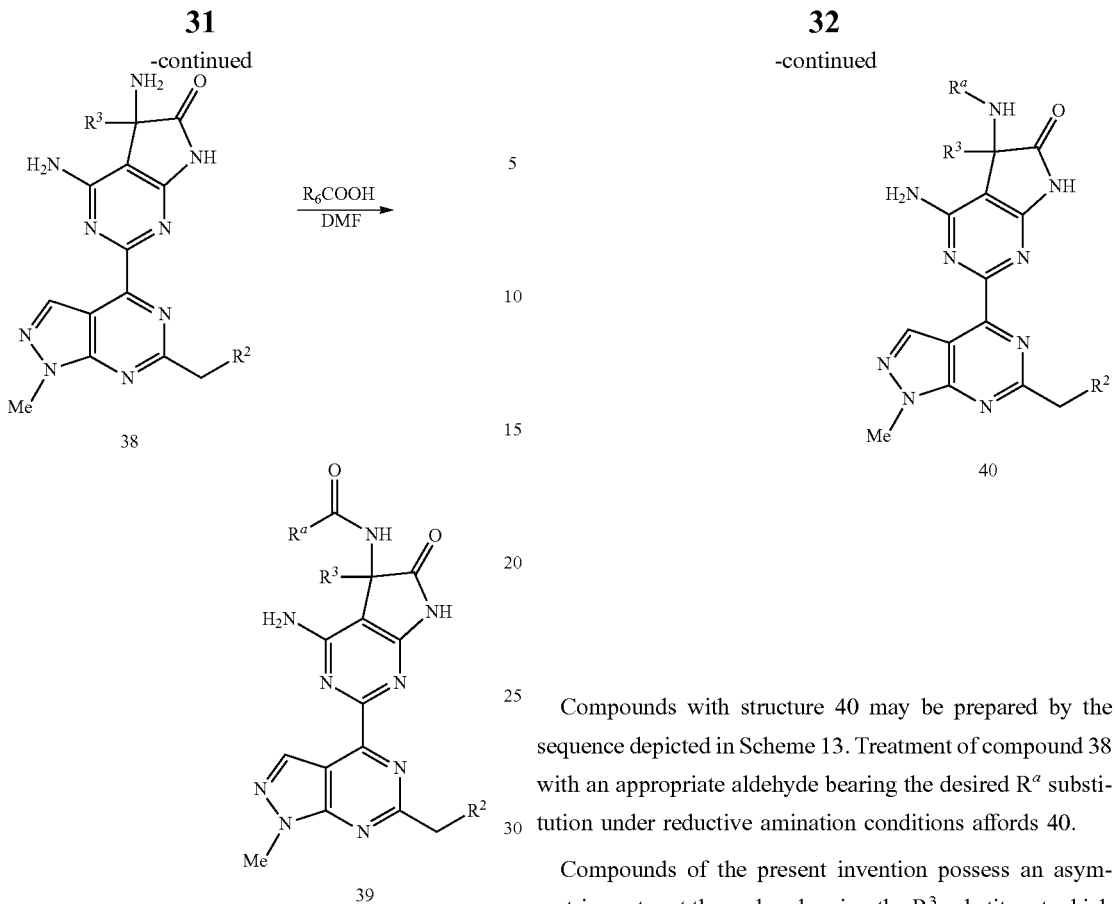

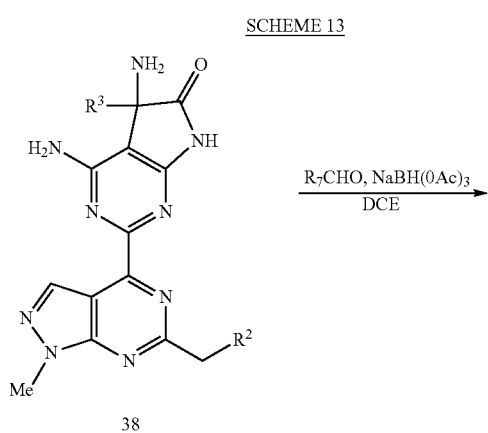

Compounds with structure 39 may be prepared by the sequence depicted in Scheme 12. Treatment of an intermediate of type 34 with hydrazine forms the acyl hydrazide intermediate 36. Oxidation of the acyl hydrazide 36 to an acyl azide occurs upon treatment with t-butyl nitrite in the presence of an TFA. Subsequent heating in an alcohol solvent such as t-BuOH affords the carbamate 37. Following TFA mediated carbamate removal, treatment of the primary amine 38 with an appropriate acylation reagent bearing the desired $R^a$ substitution affords 39.

Compounds with structure 40 may be prepared by the sequence depicted in Scheme 13. Treatment of compound 38 with an appropriate aldehyde bearing the desired $R^a$ substitution under reductive amination conditions affords 40.

Compounds of the present invention possess an asymmetric center at the carbon bearing the $R^3$ substituent which can be either R or S configuration. These enantiomeric isomers may be separated or resolved using methods familiar to those skilled in the art. For example, the compounds of the present invention may be resolved to the pure stereoisomers using chiral SFC chromatography. Use of the enantiomerically pure compound 4 as described in Schemes 2 and 3 affords enantiomerically pure products 1. Unless otherwise noted, the examples in the present invention are enantiomerically pure isomers (R or S). Biochemical assay data is listed for the more active enantiomer if only one of the enantiomers is active.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and Examples, abbreviations and acronyms may be used with the following meanings unless otherwise indicated:

aq, aq. = aqueous
Ar = aryl
BF₃OEt₂ = boron trifluoride diethyl etherate
Bu = butyl, t-Bu = tert-butyl
t-BuONO = tert-butyl nitrite
cPr or cyPr = cyclopropyl
DPPF, dppf = 1,1'-Bis(diphenylphosphino)ferrocene
DCE = 1,2-dichloroethane DIEA = diisopropylethylamine
DMA, DMAC = dimethylacetamide
DMAP = 4-dimethylaminopyridine
Et = ethyl
EtOAc = ethyl acetate eq., equiv = equivalent(s)
HOAc = acetic acid
h, hr = hour
iPr = isopropyl
IPA, i-PrOH = isopropanol
LAH = Lithium aluminum hydride Me = methyl
min, min. = minute
mCPBA = 3-chloroperoxybenzoic acid
NaHMDS = sodium bis(trimethylsilyl)amide
NIS = N-iodosuccinimide
PDA = photodiode array
Pd₂(dba)₃ = tris(dibenzylideneacetone)dipalladium (0)
Pd(PPH₃)₄ = tetrakis(triphenylphosphine)palladium (0)
iPrMgCl = isopropylmagnesium chloride
rt = retention time
RT = room temperature
SFC = supercritical fluid chromatography
TFA = trifluoroacetic acid
TLC = thin layer chromatography TMSCN = trimethylsilyl cyanide
LCMS, LC/MS = liquid chromatography-mass spectrometry
% ACT = percent activation
MeI = methyl iodide
v = volume
m.p. = melthing point
mL = milliliter(s)
mmol = millimole(s)
μM = micromolar AIBN = 2,2'-Azobisisobutyronitrile
Ac = acetate
Bn = benzyl
t-BuOK = potassium tert-butoxide
t-Boc₂O = di-tert-butyl dicarbonate
conc, conc. = concentrated
DBU = 1,8-Diazabicyclo[4.3.0]undec-7-ene dba = dibenzylideneacetone;
Pd₂dba₃ = tris(dibenzylidineacetone)dipalladium
DCM = dichloromethane
DME = 1,2-dimethoxyethane
DMF = N,N-dimethylformamide
DMSO = dimethylsulfoxide
EDC = 1-Ethyl-3-(3-dimethylaminopropyl)carbodiimidehydrochloride
EtOH = ethanol
Fe(acac)₃ = iron(III) acetylacetonate
HPLC = High pressure liquid chromatography
HMPA = hexamethylphosphoramide
LDA = lithium diisopropylamide
LiHMDS, LHMDS = lithium bis(trimethylsilyl)amide
MeOH = methanol
Mp = melting point
NMP = N-methylpyrrolidone
NBS = N-bromo succinmide
NMR = nuclear magnetic resonance
Pd/C = palladium on activated carbon
Ph = phenyl Pr = propyl psig = pounds per square inch gauge
PTFE = polytetrafluoroethylene
sat. = saturated
TEA = triethylamine
THF = tetrahydrofuran
prep TLC = preparative thin layer chromatography
TsCl = 4-toluenesulfonyl chloride
EX = example INT = intermediate
w = weight
b.p. = boiling point
L = liter(s)
Mol = mole(s)
nM = nanomolar The following examples are provided to more fully illustrate the present invention, and shall not be construed as limiting the scope in any manner. Unless stated otherwise, the following conditions were employed:

1) All operations were carried out at RT, that is, at a temperature in the range 18-25° C.;
2) Reactions are generally done using commercially available anhydrous solvents under an inert atmosphere, either nitrogen or argon;
3) Microwave reactions were done using a Biotage Initiator™ or CEM Explorer® system;
4) Evaporation of solvent was carried out using a rotary evaporator under reduced pressure (4.5-30 mmHg) with a bath temperature of up to 50° C.;
5) The course of reactions was followed by TLC and/or tandem HPLC followed by electron spray mass spectroscopy (MS), herein termed LCMS, and any reaction times are given for illustration only;
6) The structure of all final compounds was assured by at least one of the following techniques: MS or proton nuclear magnetic resonance (¹H NMR) spectrometry, and the purity was assured by at least one of the following techniques: TLC or HPLC;
7) ¹H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;
8) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection.
9) Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (typically 5% acetonitrile to 95% acetonitrile);
10) Purification of compounds by preparative thin layer chromatography (PTLC) was conducted on 20×20 cm glass plates coated with silica gel, commercially available from Analtech; or E. Merck.

11) Flash column chromatography was carried out on a Biotage SiO$_2$ cartridge system using the Biotage Horizon and Biotage SP-1 systems; or a Teledyne Isco SiO$_2$ cartridge using the CombiFlashRf system;

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any Intermediates described below may be referred to herein by their number preceded by "I-." For illustration, in the example titled "Intermediate 2," the racemic parent title compound would be referred to as Intermediate 2 (or 1-2), and the separated stereoisomers are noted as Intermediates 2A and 2B (or I-2A and I-2B). In some examples, compounds having a chiral center were derived synthetically from a single isomer intermediate; e.g., Example 1 was made using stereoisomer I-2B. Absolute stereochemistry (R or S) of each of the separated isomers was not determined, unless specifically described otherwise. An asterisk (*) may be used in a chemical structure drawing that indicates the location of a chiral center.

Intermediate 1, 1A and 1B

Methyl 3,3-dicyano-2-(4-fluorophenyl)-2-phenylpropanoate and the S and R enantiomers thereof

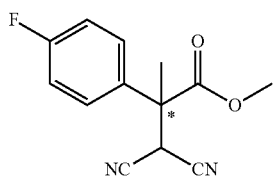 [SMILES: COC(=O)C(C)(c1ccc(F)cc1)C(C#N)C#N]

Step A: Methyl 2-(4-fluorophenyl)propanoate

Methyl 2-(4-fluorophenyl)acetate (25 g, 149 mmol) was dissolved in THF (300 mL). Hexamethylphosphoramide (26.6 g, 149 mmol) was added and the solution was cooled to −78° C. Then, lithium diisopropylamide (2 M, 78 mL, 156 mmol) was added dropwise over several min. After aging for 15 min, iodomethane (42.2 g, 297 mmol) was rapidly added and the solution was then allowed to warm to ambient temperature. The solvents were then removed under reduced pressure and the resulting residue was dissolved in EtOAc (300 mL) and washed with 1N HCl (2×200 mL) and brine (200 mL). The EtOAc layer was then dried with MgSO$_4$, filtered, and concentrated in vacuo. The resulting material was purified by silica gel chromatography eluting with a 0% to 10% EtOAc in hexanes gradient to afford the title product.

Step B: Methyl 2-bromo-2-(4-fluorophenyl)propanoate

A carbon tetrachloride (212 mL) solution of the intermediate from Step A (27 g, 148 mmol), NBS (29 g, 163 mmol) and AIBN (0.730 g, 4.45 mmol) was heated to reflux. After hr the solution was filtered while still hot and the filter cake was washed with ether (50 mL). The filtrate was concentrated and the resulting residue was dissolved in EtOAc (300 mL) and washed with water (2×300 mL) and 37% aq Na$_2$SO$_3$ (100 mL). The EtOAc was then dried with MgSO$_4$, filtered, and removed to afford the title product which was used without further purification.

Step C: Methyl 3,3-dicyano-2-(4-fluorophenyl)-2-methylpropanoate

Malononitrile (10.58 g, 160 mmol) was added to a stirred THF (300 mL) solution of potassium t-butoxide (17.97 g, 160 mmol). The resulting suspension was heated to 60° C. for 30 min then a solution of the intermediate from Step B (38 g, 146 mmol) in THF (100 mL) was added. The reaction solution was then heated at 60° C. oil bath for 2 h. THF was then removed under reduced pressure and the resulting material was dissolved in EtOAc (400 mL) and washed with 1N HCl (200 mL) and brine (200 mL). The EtOAc was then dried, filtered, and conc. in vacuo. The resulting material was purified by silica gel chromatography eluting with a 0% to 25% EtOAc in hexane gradient to give the title racemic product. $^1$H NMR (500 MHz, CDCl$_3$): δ 7.38 (2H, m), 7.16 (2H, m), 4.49 (1H, s), 3.83 (3H, s), 2.02 (3H, s). The racemic material was resolved on a Berger SFC preparative instrument using a ChiralPak AD-H column to obtain enantiomer I-1A (faster eluting) and enantiomer I-1B (slower eluting).

Intermediate 2, 2A and 2B

Methyl 3,3-dicyano-2-methyl-2-phenylpropanoate and the S and R enantiomers thereof

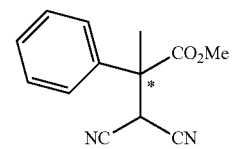 [SMILES: COC(=O)C(C)(c1ccccc1)C(C#N)C#N]

Step A: Methyl 2-phenylpropanoate

Trimethylsilyl diazomethane (2.0M in hexanes, 40 mL, 80 mmol) was added dropwise to a solution of racemic 2-phenylpropionic acid (10.0 g, 66.6 mmol) in benzene (100 mL) and MeOH (20 mL) cooled in an ice bath. After the addition was complete the reaction solution was stirred at RT for 2 h. The solution was then concentrated to give the title product.

Step B: Methyl 2-bromo-2-phenylpropanoate

A carbon tetrachloride (150 mL) solution of the intermediate from Step A (10.39 g, 66.6 mmol), NBS (14.22 g, 80 mmol) and AIBN (0.547 g, 3.33 mmol) was heated to reflux. After 4 h the reaction solution was cooled to RT and the mixture filtered. The filtrate was concentrated and the residue purified by silica gel chromatography using a 10% to 50% EtOAc in hexanes gradient to give the title product.

Step C: Methyl 3,3-dicyano-2-methyl-2-phenylpropanoate

Malononitrile (4.29 g, 65 mmol) and potassium t-butoxide (7.29 g, 65 mmol) were added to a THF (100 mL) solution containing the intermediate from Step B (15.8 g, 65 mmol). The reaction solution was then placed in an 85° C. oil bath for 4 h. The solution was then cooled to RT and partitioned between saturated aqueous ammonium chloride and EtOAc. The organic layer was washed with brine, dried over sodium sulfate, filtered, and concentrated. The crude material was purified by silica gel chromatography eluting with a 0% to 30% EtOAc in hexanes gradient to give the title racemic product. $^1$H NMR (500 MHz, CDCl$_3$): δ 7.44-7.42 (3H, m), 7.38-7.36 (2H, m), 4.50 (1H, s), 3.80 (3H, s), 2.00 (3H, s). The racemic material was resolved on a Berger SFC preparative instrument using a ChiralPak AD-H to obtain enantiomer I-2A (faster eluting) and enantiomer I-2B (slower eluting).

Using essentially the same procedures described for Intermediates 1 and 2, the following compounds in Table 1 were made.

mL) at 0° C. was added propanedinitrile (120 g, 1.818 mol) dropwise. After the addition, the resulting solution was stirred at 70° C. overnight and concentrated under vacuum. The residue was purified by silica gel chromatography using a 10/1 gradient of EtOAc/petroleum ether to give the title product.

Step 2: Ethyl 2-(4-chlorophenyl)-3,3-dicyano-2-methylpropanoate

To a stirred mixture of intermediate from Step A (82.0 g, 0.315 mol) and LiCl (26.2 g, 0.624 mol) in THF (1.3 L) at 0° C. was added MeMgBr (213 mL, 639 mmol, 3 mol/L) dropwise. The resulting solution was then stirred for 2 h at RT and quenched by the addition of 500 mL of NH$_4$Cl (sat.). The resulting mixture was extracted with EtOAc (500 mL×3). The organic layers were combined, dried over anhydrous sodium sulfate, and concentrated under vacuum. The residue was purified by silica gel chromatography using a EtOAc/petroleum ether=10/1 gradient to give the title product. $^1$H NMR (500 MHz, CDCl$_3$): δ 7.44-7.46 (2H, m), 7.33-7.35 (2H, m), 4.48 (1H, s), 4.25-4.34 (2H, m), 2.01 (3H, s), 1.28 (3H, t, J=7.13 Hz). The racemic material was resolved on a SHIMADZU LC-8A preparative instrument using a Chiralcel OJ column to obtain enantiomer I-5A (faster eluting) and enantiomer I-5B (slower eluting).

TABLE 1

| INT | R$^1$ | R$^2$ | Characterizaton Data |
|---|---|---|---|
| 3 | CO$_2$Et | Et | $^1$H NMR (500 MHz, CDCl$_3$): δ 4.55 (1 H, s), 4.41-4.28 (4 H, m), 1.83 (3 H, s), 1.35 (6 H, t, J = 7.15 Hz). |
| 4 | 4-Br-phenyl | Et | $^1$H NMR (300 MHz, CDCl3): δ 7.60-7.55 (2 H, m), 7.27-7.21 (2 H, m), 4.47 (1 H, s), 4.37-4.13 (2 H, m), 1.97 (3 H, s), 1.25 (3 H, t, J = 7.2 Hz). Enantiomers resolved using Chiracel OJ column. |

Intermediate 5, 5A and 5B

Ethyl 2-(4-chlorophenyl)-3,3-dicyano-2-methylpropanoate and the S and R enantiomers thereof

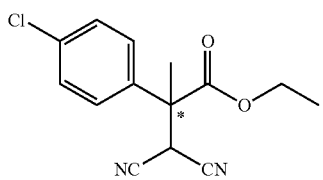 [SMILES: CCOC(=O)C(C)(c1ccc(Cl)cc1)C(C#N)C#N]

Step 1: Ethyl 2-(4-chlorophenyl)-3,3-dicyanoacrylate

To a solution of ethyl 2-(4-chlorophenyl)-2-oxoacetate (90.0 g, 0.425 mol) and piperidine (6.3 mL) in EtOH (900

Intermediate 6

ETHYL 2-(DICYANOMETHYL)-2-METHYLBUT-3-YNOATE

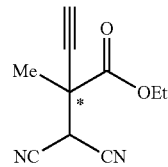

To a flask containing anhydrous LiCl (25.8 mg, 0.609 mmol) in THF (1 mL), was added a solution of ethynylmagnesium bromide (1.3 mL, 0.640 mmol, 0.5M in THF). The reaction was stirred at RT for 25 min. The resulting solution was then added to a solution of ethyl 3,3-dicyano-2-methylprop-2-enoate (prepared according to Hagiware et. al. *Synthesis* 1974, 9, 669) (0.609 mL, 0.609 mmol, 1M solution in benzene) in THF (22.5 mL) at −10 to −20 C fast dropwise via syringe. The reaction was stirred for 10 min and quenched with saturated aq NH₄Cl, and then diluted with water and EtOAc. The layers were separated and the organic layer was dried with anhydrous sodium sulfate and concentrated. The residue was purified by silica gel chromatography using a 0% to 40% EtOAc in hexanes gradient to give the title product. ¹H NMR (500 MHz, CDCl₃): δ 4.34 (q, J=7.17 Hz, 2H), 4.31 (s, 1H), 2.66 (s, 1H), 1.80 (s, 3H), 1.35 (t, J=7.14 Hz, 3H). The title racemic intermediate was used for the synthesis of final products.

Intermediate 7

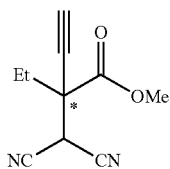

Step A: Methyl 2-(dicyanomethylene)butanoate

Methyl 2-oxobutanoate (15 g, 129 mmol) and malononitrile (12.80 g, 194 mmol) were added to a flask followed by the addition of 3-aminopropanoic acid (0.575 g, 6.46 mmol) as a solution in water (12.92 ml), followed by the addition of EtOH (12.92 ml) and the reaction is left to stir for two h. The mixture was diluted with EtOAc and water. The layers were separated and the organic layer was dried with anhydrous sodium sulfate and concentrated. Silica gel chromatography (0% to 40% EtOAc in hexanes gradient) afforded the title product.

Step B Methyl 2-(dicyanomethyl)-2-ethylbut-3-ynoate

The intermediate from step A in THF (3.50 ml) under nitrogen was cooled to −50° C. Ethynylmagnesium bromide (4.20 ml, 2.102 mmol) was added dropwise and the reaction was slowly allowed to warm in the bath for ~30 min. The mixture was quenched with saturated aq. NH₄Cl and diluted with EtOAc and water. The layers were separated and the organic layer was dried with anhydrous sodium sulfate and concentrated. Silica gel chromatography (0% to 40% EtOAc in hexanes gradient) gave the title compound. ¹H NMR (500 MHz, CDCl₃): 4.28 (1H, s), 3.88 (3H, s), 2.70 (1H, s), 2.04-2.16 (2H, m), 1.07 (3H, t, J=7.44 Hz). The title racemic intermediate was used for the synthesis of final products.

Intermediate 8

Methyl 2-cyclopropyl-2-(dicyanomethyl)but-3-ynoate

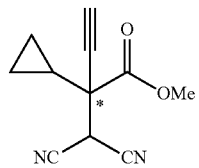

Step A: Methyl 3,3-dicyano-2-cyclopropylacrylate

A mixture of methyl 2-cyclopropyl-2-oxoacetate (prepared similarly to: *Russian Chemical Bulletin* 2007, 56, 1515-1521) (800 mg, 6.24 mmol) and malononitrile (516 mg, 7.80 mmol) was stirred for 2-3 min. A solution of beta-alanine (27.8 mg, 0.312 mmol) in water (535 μl) was added in small portions over ~5 min period. The reaction was cooled in an ice-bath and EtOH (350 μl) was added. The reaction was stirred at RT for 24 h. The reaction was diluted with water and extracted with ethyl ether. The ether layer was back extracted 2× with water. The ether layer was further diluted with EtOAc and dried (sodium sulfate). The combined organic layers were purified by silica gel column chromatography eluting with a 0% to 30% EtOAc in hexanes gradient to give the title product.

Step B: Methyl 2-cyclopropyl-2-(dicyanomethyl)but-3-ynoate

To a flask containing anhydrous LiCl (144 mg, 3.41 mmol) in THF (2 mL) was added a solution of ethynylmagnesium bromide (6.8 mL, 3.41 mmol, 0.5M in THF). The reaction was stirred at RT for 30 min. The resulting solution was cooled to −30° C. A solution of the intermediate from Step A (0.500 g, 2.84 mmol) in THF (5 mL) was added. The reaction was stirred for 1 h in the cooling bath then raised up to RT slowly. The mixture was quenched with saturated aqueous NH₄Cl, and then diluted with water and EtOAc. The layers were separated and the organic layer was dried with sodium sulfate and concentrated in vacuo. Purification by silica gel column chromatography eluting with a 0% to 30% EtOAc in hexanes gradient afforded the title product. ¹H NMR (500 MHz, CDCl₃): δ 4.41 (1H, s), 3.93 (3H, s), 2.63 (1H, s), 1.31-1.24 (1H, m), 1.03-0.96 (1H, m), 0.92-0.79 (2H, m), 0.77-0.67 (1H, m). The title racemic intermediate was used for the synthesis of final products.

Intermediate 9

Methyl 3,3-dicyano-2-(4-iodophenyl)-2-methylpropanoate, (S)-methyl 3,3-dicyano-2-(4-iodophenyl)-2-methylpropanoate, and (R)-methyl 3,3-dicyano-2-(4-iodophenyl)-2-methylpropanoate

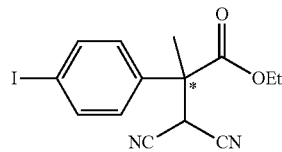 [SMILES: CCOC(=O)C(C)(c1ccc(I)cc1)C(C#N)C#N]

Isopropylmagnesium chloride LiCl complex (6.09 mL, 7.92 mmol, 1.3 M in THF) was added to a solution of 1,4-diiodobenzene (2.61 g, 7.92 mmol) in THF (25 mL) cooled to −30° C. The reaction was stirred for 2 h with the temperature maintained −30° C. A solution of ethyl 3,3-dicyano-2-methylprop-2-enoate (prepared according to Hagiware et. al. *Synthesis* 1974, 9, 669) (1.0 g, 6.09 mmol) in benzene (2 mL) was added. The resulting mixture was warmed to RT and stirred for 5 min. The reaction was then quenched with saturated aqueous NH₄Cl and extracted with EtOAc. The organic layer was dried (sodium sulfate) and concentrated in vacuo. Purification by silica gel column chromatography eluting with a 0% to 25% EtOAc in hexanes gradient afforded the title product. ¹H NMR (500 MHz, CDCl₃): δ 7.80 (2H, d, J=8.31 Hz), 7.14 (2H, d, J=8.31 Hz), 4.47 (1H, s), 4.36-4.24 (2H, m), 1.99 (3H, s), 1.28 (3H, t, J=7.14 Hz). The racemic material was resolved on a Berger SFC preparative instrument using a Chiralpak AD-H column to obtain enantiomer I-9A (faster eluting) and enantiomer I-9B (slower eluting).

Intermediate 10

Diethyl cyclopropyl (dicyanomethyl)propanedioate

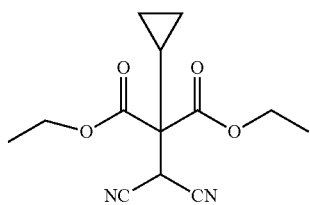 [SMILES: CCOC(=O)C(C(=O)OCC)(C(C#N)C#N)C1CC1]

A THF (45.0 ml) solution of diethyl (dicyanomethylidene)propanedioate (prepared analogous to Sentman et. al. *J. Org. Chem.* 1982, 47, 4577) (4.5 ml, 4.5 mmol, 1M solution in benzene) was cooled to 0° C. and cyclopropylmagnesium bromide (9.00 ml, 4.50 mmol) and lithium chloride (0.191 g, 4.5 mmol) were added. The reaction was stirred at 0° C. for 2 h and then warmed to RT while stirring for an additional 2 h. The reaction was diluted with EtOAc and quenched with saturated aqueous NH₄Cl. The layers were separated and the organic layer was dried with MgSO₄, filtered, and concentrated in vacuo. Purification by silica gel column chromatography eluting with a 0% to 40% EtOAc in hexanes gradient afforded the title product. ¹H NMR (500 MHz, CDCl₃): δ 4.41 (1H, s), 4.38-4.26 (4H, m), 1.52-1.45 (1H, m), 1.33 (6H, t, J=7.14 Hz), 0.86-0.79 (2H, m), 0.71-0.66 (2H, m).

Intermediate 11

ETHYL 3,3-DICYANO-2-CYCLOHEXYL-2-METHYLPROPANOATE

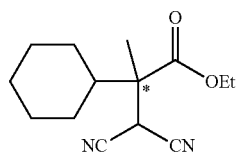 [SMILES: CCOC(=O)C(C)(C(C#N)C#N)C1CCCCC1]

Step A: Ethyl 2-cyclohexyl-2-oxoacetate

A 250-mL 3-necked round-bottom flask was purged and maintained with an inert atmosphere of nitrogen, and into it was added diethyl oxalate (7.3 g, 49.95 mmol, 1.0 equiv) and THF (80 mL), and then bromo(cyclohexyl)magnesium (50 mL, 50 mmol, 1.0 equiv, 1 N) was added dropwise at 0° C. The resulting solution was stirred for 2 h at ambient temperature. The reaction was then quenched by the addition of NH₄Cl (3 N, 100 mL). The resulting solution was extracted with EtOAc (3×100 mL) and the organic layers were combined, dried over anhydrous sodium sulfate and filtered. The filtrate was concentrated in vacuo to afford the title product.

Step B: Ethyl 3, 3-dicyano-2-cyclohexylprop-2-enoate

Into a 250-mL round-bottom flask, was placed the intermediate from Step A (9.0 g, 48.85 mmol, 1.00 equiv), propanedinitrile (3.2 g, 48.44 mmol, 1.00 equiv), 3-aminopropanoic acid (2.17 g, 24.36 mmol, 1.50 equiv), water (10 mL), the mixture was stirred for 10 min at ambient temperature, EtOH (10 mL) was added. The resulting solution was stirred for 16 h at ambient temperature. The reaction was then quenched by the addition of brine (100 mL). The resulting solution was extracted with EtOAc (3×100 mL) and the organic layers were combined, dried over anhydrous sodium sulfate and filtered. The filtrate was concentrated in vacuo to dryness. The residue was applied onto a C18 column with water/acetonitrile=1/4 to afford the title product.

Step C: Ethyl 3,3-dicyano-2-cyclohexyl-2-methylpropanoate

Into a 100-mL 3-necked round-bottom flask purged and maintained with an inert atmosphere of nitrogen, were placed the intermediate from Step B (1.3 g, 5.6 mmol, 1.0 equiv), lithium chloride (0.35 g, 8.30 mmol, 1.50 equiv) and THF (18 mL). Bromo(methyl)magnesium (2.24 g, 0.56 mmol, 1.2 equiv) was added dropwise at 0° C. The resulting solution was stirred for 3 h at ambient temperature. The reaction was then quenched by the addition of saturated aq. ammonium chloride solution (50 mL). The mixture was extracted with EtOAc (3×80 mL) and the organic layers were combined, dried over anhydrous sodium sulfate and filtered. The filtrate was concentrated in vacuo. Purification by silica gel column chromatography eluting with 10% petroleum ether in diethyl ether afforded the title product. ¹H NMR (300 MHz, CDCl₃): δ 4.34-4.22 (3H, m), 1.87-1.81 (3H), 1.77-1.57 (3H, m), 1.53 (3H, s), 1.34 (3H, t, J=7.2 Hz), 1.26-1.21 (2H, m), 1.18-1.14 (3H, m). The title racemic intermediate was used for the synthesis of final products.

Using essentially the same procedures as described for making Intermediates 5 to 11, the following compounds in Table 1A were synthesized. NMR characterization data for the noted intermediates is provided in Table 1B.

TABLE 1A

| INT | R¹ | R² | R³ | Resolution Conditions |
|---|---|---|---|---|
| 12 | ![4-methoxyphenyl] | Me | Et | Chiralpak AD-H |
| 13 | ![3-methoxyphenyl] | Me | Et | Racemate used |

TABLE 1A-continued

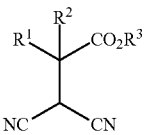

| INT | R¹ | R² | R³ | Resolution Conditions |
|---|---|---|---|---|
| 14 | 4-(CO₂Et)-phenyl | Me | Et | Chiralpak AD-H |
| 15 | 4-F-phenyl | cyclopropyl | Me | Chiralcel OJ |
| 16 | 3-F-4-OMe-phenyl | Me | Et | Racemate used |
| 17 | n-Bu | cyclopropyl | Me | Racemate used |
| 18 | Me | cyclopropyl | Et | Racemate used |
| 19 | CO₂Et | Et | Et | N/A (Not Applicable) |
| 20 | CO₂Et | i-Pr | Et | N/A |
| 21 | 3-F-4-Cl-phenyl | Me | Et | Chiralcel OJ-H |
| 22 | 3-OMe-4-F-phenyl | Me | Me | Chiralpak AS-H |

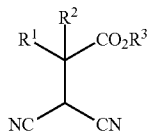

TABLE 1B

| INT | Characterizaton Data |
|---|---|
| 12 | ¹H NMR (500 MHz, CDCl₃): δ 7.31 (2 H, t, J = 8.89 Hz), 6.97 (2 H, d, J = 8.69 Hz), 4.49 (1 H, s), 4.36-4.22 (2 H, m), 3.85 (3 H, s), 2.00 (3 H, s), 1.31-1.25 (3 H, m). |
| 13 | ¹H NMR (500 MHz, CDCl₃): δ 7.38 (1 H, t, J = 8.05 Hz), 6.98-6.91 (3 H, m), 4.52 (1 H, s), 4.36-4.22 (2 H, m), 3.84 (3 H, s), 2.00 (3 H, s), 1.28 (3 H, t, J = 7.13 Hz), |
| 14 | ¹H NMR (500 MHz, CDCl₃): δ 8.14 (2 H, d, J = 8.35 Hz), 7.48 (2 H, d, J = 8.37 Hz), 4.53 (1 H, s), 4.42 (2 H, q, J = 7.13 Hz), 4.36-4.25 (2 H, m), 2. 2.02 (3 H, s), 1.43 (3 H, q, J = 7.00 Hz), 1.28 (3 H, q, J = 7.04 Hz). |
| 15 | ¹H NMR (500 MHz, CDCl₃): δ 6.97-6.92 (2 H, m), 6.82-6.77 (2 H, m), 4.79 (1 H, s), 3.93 (3 H, s), 2.32-2.25 (1 H, m), 1.47-1.26 (4 H, m). |
| 16 | ¹H NMR (500 MHz, CDCl₃): δ 7.09-7.12 (2 H, m), 6.99 (1 H, t, J = 8.58 Hz), 4.48 (1 H, s), 4.23-4.31 (2 H, m), 3.89 (3 H, s), 1.94 (3 H, s), 1.24 (3 H, t, J = 7.14 Hz). |
| 17 | ¹H NMR (500 MHz, CDCl₃): δ 4.31 (1 H, s), 3.79 (3 H, s), 1.91-1.67 (2 H, m), 1.45-1.29 (3 H, m), 1.28-1.09 (2 H, m), 0.99-0.87 (3 H, m), 0.78-0.64 (3 H, m), 0.55-0.47 (1 H, m). |
| 18 | ¹H NMR (500 MHz, CDCl₃): δ 4.30-4.17 (3 H, m), 1.35 (3 H, s) 1.32-1.24 (3 H, m), 1.17-1.11 (1 H, m), 0.71-0.58 (3 H, m), 0.50-0.45 (1 H, m). |
| 19 | ¹H NMR (500 MHz, CDCl₃): δ 4.41 (1 H, s), 4.35-4.27 (4 H, m), 2.28-2.20 (2 H, m), 1.31 (6 H, t, J = 7.16 Hz), 1.05 (3 H, t, J = 7.50 Hz). |
| 20 | ¹H NMR (500 MHz, CDCl₃): δ 4.48 (1 H, s), 4.39 (4 H, q, J = 7.13 Hz), 2.74-2.80 (1 H, m), 1.38 (6 H, t, J = 7.15 Hz),, 1.18 (6 H, d, J = 6.94 Hz). |
| 21 | ¹H NMR (400 MHz, CDCl₃): δ 7.42 (1 H, t, J = 8.40 Hz), 7.31 (1 H, dd, J = 7.20, 2.25 Hz), 7.21-7.18 (1 H, m), 4.58 (1 H, s), 4.35-4.27 (2 H, m), 2.01 (3 H, s), 1.28 (3 H, t, J = 7.20 Hz). |
| 22 | ¹H NMR (500 MHz, CDCl₃): δ 7.12 (1 H, dd, J = 10.72, 8.46 Hz), 6.95-6.88 (2 H, m), 4.46 (1 H, s), 4.34-4.21 (2 H, m), 3.90 (3 H, s), 1.98 (3 H, s), 1.26 (3 H, td, J = 7.12, 2.88 Hz). |

Intermediate 23

METHYL 3,3-DICYANO-2,2-DIMETHYLPROPANOATE

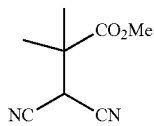

A 12 L, 3 neck round bottom flask equipped with a mechanical stirrer, thermometer, condenser and nitrogen bubbler, was charged with malononitrile (251 g, 3.802 moles) and THF (2 liters). Potassium t-butoxide (1M THF, 3.802 L, 3.802 moles) was then added. The mixture was stirred at 50° C. for 30 min. Methyl 2-bromoisobutyrate (688 g, 3.80 moles) was added and the reaction mixture was stirred overnight at 50° C. The reaction was partitioned between aqueous 1 N HCl and EtOAc. The organic phase was washed with brine, dried over $MgSO_4$, filtered, and concentrated to give the title product. $^1$H NMR (400 MHz, $CD_3CN$): δ 4.35 (1H, s) 3.73 (3H, s), 1.43 (6H, s).

EXAMPLE 1

4-Amino-5-methyl-2-(1-methyl-6-(3,3,4,4,4-pentafluorobutyl)-1H-pyrazolo[3,4-d]pyrimidin-4-yl)-5-phenyl-5H-pyrrolo[2,3-d]pyrimidin-6(7H)-one

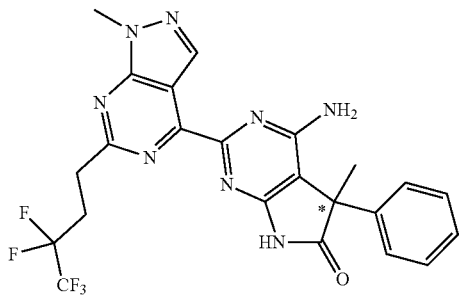 [SMILES: Cn1ncc2c(-c3nc(N)c4c(n3)NC(=O)C4(C)c3ccccc3)nc(CCC(F)(F)C(F)(F)F)nc21]

Step A: 4,4,5,5,5-Pentafluoropentanoic acid

To a stirred solution of Jones Reagent (a solution of chromium trioxide in diluted sulfuric acid) (20 ml, 160 mmol) in acetone (20 mL) at 0° C., a solution of 4,4,5,5,5-pentafluoropentan-1-ol (7.12 g, 40 mmol) in acetone (30 mL) was added dropwise. After in remaining ice bath, the mixture was stirred continuously at RT for 1 h. The mixture was poured into ice/water and extracted with diethyl ether. Crude ether mixture was extracted with aqueous 2N sodium hydroxide. On the inorganic layer was acidified with aqueous 6N HCl and the organic layer was extracted with diethyl ether. The ether layer was washed with brine, dried over anhydrous sodium sulfate and concentrated in vacuo to give the title product.

Step B: Propyl 4,4,5,5,5-pentafluoropentanoate

To a solution of the intermediate from Step A (25 g, 0.13 mol) in propanol (100 mL) at 0° C. was added thionyl chloride (14.9 mL, 0.195 mol). The mixture was then stirred at RT for 5 h. The solution was concentrated in vacuo. The residue was diluted with EtOAc and poured into ice water. The organic layer was washed by aqueous $NaHCO_3$ solution, dried over anhydrous $Na_2SO_4$, concentrated in vacuo to give the title product.

Step C: 1-Methyl-6-(3,3,4,4,4-pentafluorobutyl)-1H-pyrazolo[3,4-d]pyrimidin-4-ol The mixture of 5-amino-1-methyl-1H-pyrazole-4-carboxamide (70 g, 0.49 mol), EtONa (117 g, 1.72 mol) and the intermediate from Step B ((272 g, 1.16 mol) in EtOH (1 L) was stirred in a sealed bottle at 120° C. overnight. The mixture was concentrated and the residue was diluted with $H_2O$ (2 L) and then adjusted to pH=6 with 2 N aqueous HCl solution. The mixture was extracted with EtOAc (1 L×3). The combined organic layer was dried over $Na_2SO_4$, filtered and concentrated. The residue was purified by silica gel column chromatography using petroleum ether/EtOAc=1:1 to give the title product.

Step D: 4-Chloro-1-methyl-6-(3,3,4,4,4-pentafluorobutyl)-1H-pyrazolo[3,4-d]pyrimidine The intermediate from Step C (43 g, 0.145 mmol) in $POCl_3$ (250 mL) was stirred at 115° C. overnight. The mixture was diluted with EtOAc (2 L) and then washed with $H_2O$ (1 L×5). The organic layer was dried and concentrated in vacuo. The residue was purified by silica gel column chromatography using EtOAc/petroleum ether=1:5 to give the title product.

Step E: 1-Methyl-6-(3,3,4,4,4-pentafluorobutyl)-1H-pyrazolo[3,4-d]pyrimidine-4-carbonitrile A mixture of the intermediate from Step D (38 g, 0.12 mol), $ZnCN_2$ (38 g, 0.33 mol), $Pd_2(dba)_3$ (3.5 g), dppf (4.3 g) in DMF (1 L) was stirred at 115° C. for 4 h. The mixture was filtered and the filtrate was concentrated in vacuo. The residue was purified by silica gel column chromatography using EtOAc/petroleum ether=1:10 to give the title product.

Step F: 1-Methyl-6-(3,3,4,4,4-pentafluorobutyl)-1H-pyrazolo[3,4-d]pyrimidine-4-carboximidamide To $NH_4Cl$ (27 g, 0.51 mol) in toluene (1 L) was added $Me_3Al$ (254 mL, 0.51 mol, 2 mol/L) dropwise, then stirred at RT for 1 h. The intermediate from Step D (77.5 g, 0.25 mol) was added to the above solution and heated to 120° C. The mixture was stirred at this temperature for 2 h, and then cooled to RT. MeOH, DCM and silica gel were added and stirred for 15 min, filtered off solid. The filtrate was concentrated and the crude was suspended in THF and filtered again. The filtrate was concentrated and washed with petroleum ether:EtOAc=10:1 (100 mL). The solid was dried in vacuo to get the title product

Step G: 4-Amino-5-methyl-2-(1-methyl-6-(3,3,4,4,4-pentafluorobutyl)-1H-pyrazolo[3,4-d]pyrimidin-4-yl)-5-phenyl-5H-pyrrolo[2,3-d]pyrimidin-6(7H)-one A tert-butanol (2.0 mL) solution containing the intermediate from Step F (40 mg, 0.124 mmol), Intermediate 2B (45 mg, 0.186 mmol) and potassium tert-butoxide (17 mg, 0.149 mmol) was heated at 120° C. in a sealed tube for 1.5 h. The reaction was then purified by reverse phase HPLC using water/acetonitrile (0.1% TFA) to give the title product. $^1$H NMR (500 MHz, DMSO-d$_6$): δ 11.30 (1H, s), 9.01 (1 H, s), 7.41-7.26 (5H, m), 6.79 (2H, s), 4.07 (3H, s), 3.36-3.21 (2H, partially overlapping with H$_2$O), 2.95-2.82 (2H, m), 1.81 (3H, s), m/z=519 (M+H).

EXAMPLE 2

4-Amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one

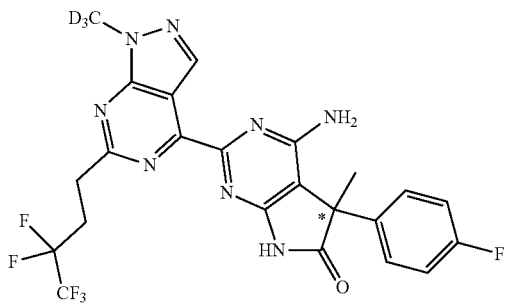 [SMILES: [2H]C([2H])([2H])n1ncc2c(-c3nc(N)c4c(n3)NC(=O)C4(C)c3ccc(F)cc3)nc(CCC(F)(F)C(F)(F)F)nc21]

Step A: 5-Amino-1-trideuteriomethy-1H-pyrazole-4-carbonitrile

3-Amino-1H-pyrazole-4-carbonitrile (200 g, 1.85 mol) was dissolved in 1 L of DMF in a 2 L of three-necked flask. Cs$_2$CO$_3$ (260 g, 2.03 mol) was then added. The mixture was cooled to 0° C. and CD$_3$I (280 g, 1.93 mol) was added slowly at 0° C.-10° C. The solution was stirred for 6 h at 0-1° C. The solvent was concentrated and DCM (500 mL) was added and the mixture was stirred for 0.5 hr at RT. The mixture was filtered and the filter cake was washed with DCM (250 mL). Another 250 mL of DCM was added to the filter cake and the mixture was stirred for 0.5 hr at RT. It was filtered again and the filter cake was washed again with DCM (250 mL) and dried to give the title product.

Step B: 5-Amino-1-trideuteriomethyl-1H-pyrazole-4-carboxamide

To the intermediate from Step A (120 g, 0.96 mol) was added conc.H$_2$SO$_4$ (500 mL) at 10° C. The resulting mixture was stirred for 6 h at RT and CH$_3$CN (300 mL) was added slowly at 0-1° C. The mixture was filtered and washed the filter cake with CH$_3$CN (1 L). The solid was dissolved in water (600 mL) and NaOH aqueous solution (50 wt %) was added until the pH=7. Water was removed in vacuo and DMF (200 mL) was added. The mixture was filtered. The filter cake was washed with DMF (100 mL) and DMF filtrate was saved. The cake was recovered and stirred in DMF (200 mL) for 0.5 h at RT. The mixture was filtered again. The cake was washed with DMF (200 mL) and DMF filtrate was also saved. Both saved DMF filtrates were combined and concentrated to give the title product.

Step C: 6-(3,3,4,4,4-Pentafluorobutyl)-1-trideuteriomethyl-1H-pyrazolo[3,4-d]pyrimidine-4-carboximidamide The title compound was prepared from the intermediate in 5-Amino-1-trideuteriomethyl-1H-pyrazole-4-carboxamide and Propyl 4,4,5,5,5-pentafluoropentanoate (see Example 1, Step B) according to the procedure described in Step C to Step F of Example 1.

Step D: 4-Amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one A tert-butanol (7 mL) solution containing the intermediate from Step C (210 mg, 0.646 mmol), Intermediate 1B (238 mg, 0.968 mmol) and KHCO$_3$ (129 mg, 1.29 mmol) was heated at 120° C. in a sealed tube for 18 h. The solvents were then removed under reduced pressure and the resulting material was purified on silica gel chromatography eluting with a 0% to 100% EtOAc in hexanes gradient to afford the title product. $^1$H NMR (500 MHz, DMSO-d$_6$): δ 11.32 (1H, s), 9.02 (1H, s), 7.31 (2H, t, J=6.43 Hz), 7.18 (2H, t, J=8.59 Hz), 6.84 (2H, s), 3.40-3.21 (2H, partially overlapping with H$_2$O), 2.95-2.82 (2H, m), 1.81 (3H, s), m/z=537 (M+H).

EXAMPLE 3

4-Amino-5-methyl-2-(1-methyl-6-(4,4,4-trifluorobutyl)-1H-pyrazolo[3,4-d]pyrimidin-4-yl)-5-phenyl-5H-pyrrolo[2,3-d]pyrimidin-6(7H)-one

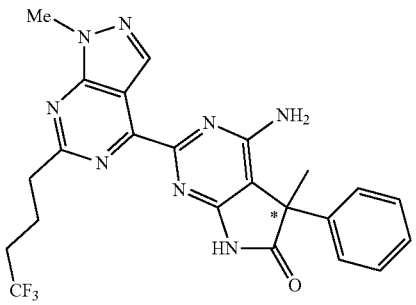 [SMILES: Cn1ncc2c(-c3nc(N)c4c(n3)NC(=O)C4(C)c3ccccc3)nc(CCCC(F)(F)F)nc21]

Step A: Ethyl 5,5,5-trifluoropentanoate

To a solution of 5,5,5-trifluoropentanoic acid (9.89 g, 63.4 mol) in EtOH (60 mL) at 0° C. was added thionyl chloride (6.94 mL, 95.0 mol) dropwise. The mixture was then stirred at RT for 5 h. The solution was concentrated in vacuo. The residue was diluted with diethyl ether and poured into ice water. The organic layer was washed by aqueous NaHCO$_3$ solution, dried over MgSO$_4$, concentrated in vacuo to give the title product.

Step B: 1-Methyl-6-(4,4,4-trifluorobutyl)-1H-pyrazolo[3,4-d]pyrimidine-4-carboximidamide The title compound was prepared using the intermediate from Step A and 5-amino-1-methyl-1H-pyrazole-4-carboxamide according to the procedure described in Step C to Step F of Example 1.

Step C: 4-Amino-5-methyl-2-(1-methyl-6-(4,4,4-trifluorobutyl)-1H-pyrazolo[3,4-d]pyrimidin-4-yl)-5-phenyl-5H-pyrrolo[2,3-d]pyrimidin-6(7H)-one The title compound was prepared from the intermediate from Step B and Intermediate 2B according to the procedures described in Step G of Example 1. $^1$H NMR (500 MHz, CDCl$_3$): δ 11.30 (1H, s), 8.99 (1H, s), 7.35 (2H, t, J=7.39 Hz), 7.29 (2H, t, J=8.09 Hz), 6.78 (2H, s), 4.06 (3H, s), 3.15 (2H, t, J=7.69 Hz), 2.48-2.40 (2H, partially overlapping with DMSO), 2.08 (2H, t, J=7.78 Hz), 1.81 (3H, s), m/z=483 (M+H).

EXAMPLE 4

4-Amino-5-methyl-2-(1-methyl-6-(3,3,3-trifluoropropyl)-1H-pyrazolo[3,4-d]pyrimidin-4-yl)-5-phenyl-5H-pyrrolo[2,3-d]pyrimidin-6(7H)-one

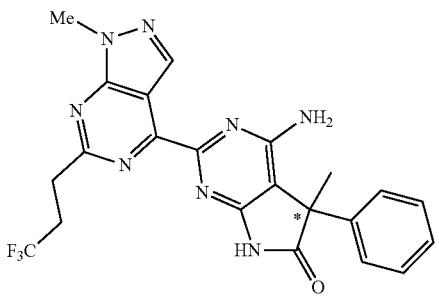 [SMILES: Cn1ncc2c(-c3nc(N)c4c(n3)NC(=O)C4(C)c3ccccc3)nc(CCC(F)(F)F)nc21]

Step A: 1-Methyl-5-(4,4,4-trifluorobutanamido)-1H-pyrazole-4-carboxamide

Isopropyl chloroformate (1.95 g, 14.3 mmol) and N-methylmorpholine (1.44 g, 14.3 mmol) were added to a solution of 4,4,4-trifluorobutanoic acid (2.03 g, 14.3 mmol) in THF (40 mL) at −15° C. The solution was stirred for 10 min then cooled to −50° C. and a solution of 5-amino-1-methyl-1H-pyrazole-4-carboxamide (2.0 g, 14.3 mmol) and DIEA (2.49 ml, 14.3 mmol) in DMF (20 ml) was added. The solution was allowed to slowly warm to ambient temperature over 2 h. The solution was diluted with EtOAc and washed with brine. The organic layer was dried, filtered, and concentrated in vacuo. The crude product was purified by silica gel chromatography using 0% to 15% MeOH in CH$_2$Cl$_2$ gradient to give the title compound.

Step B: 1-Methyl-6-(3,3,3-trifluoropropyl)-1H-pyrazolo[3,4-d]pyrimidin-4-ol

The intermediate from Step A (1.2 g, 4.54 mmol) and sodium ethoxide (0.31 g, 4.54 mmol) were suspended in EtOH (20 ml) and heated for 2 h under reflux. The solution was cooled to RT and saturated aqueous NH$_4$Cl was added. The material was extracted EtOAc. The organic layer was dried, filtered, and concentrated in vacuo to give the title compound.

Step C: 1-Methyl-6-(3,3,3-trifluoropropyl)-1H-pyrazolo[3,4-d]pyrimidine-4-carboximidamide The title compound was prepared from the intermediate from Step B according to the procedure described in Step D to Step F of Example 1.

Step D: 4-Amino-5-methyl-2-(1-methyl-6-(3,3,3-trifluoropropyl)-1H-pyrazolo[3,4-d]pyrimidin-4-yl)-5-phenyl-5H-pyrrolo[2,3-d]pyrimidin-6(7H)-one The title compound was prepared from the intermediate from Step C and Intermediate 2B according to the procedures described in Step G of Example 1. $^1$H NMR (500 MHz, DMSO-d$_6$): δ11.29 (1H, s), 9.01 (1H, s), 7.40-7.26 (5H, m), 6.75 (2H, s), 4.03 (3H, s), 3.36-3.21 (2H, partially overlapping with H$_2$O), 3.00-2.87 (2H, m), 1.81 (3H, s), m/z=469 (M+H).

EXAMPLE 5

4-Amino-2-(6-((3,3-difluorocyclobutyl)methyl)-1-methyl-1H-pyrazolo[3,4-d]pyrimidin-4-yl)-5-(4-fluorophenyl)-5-methyl-5H-pyrrolo[2,3-d]pyrimidin-6(7H)-one

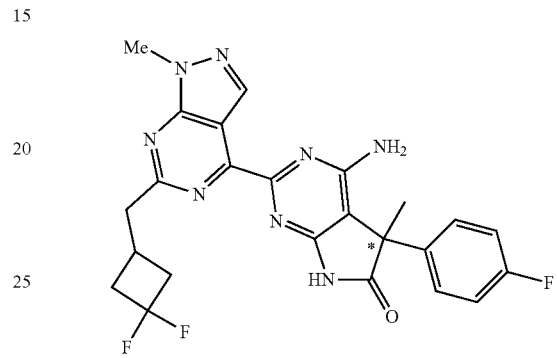

Step A: (3,3-Difluorocyclobutyl)methyl 4-methylbenzenesulfonate

To a 250 mL round-bottom flask in a water bath at RT, (3,3-difluorocyclobutyl)methanol (20 g, 164 mmol), DCM (100 ml), triethylamine (34.2 mL, 246 mmol), DMAP (2 g, 16.38 mmol) and Tosyl-Cl (37.5 g, 197 mmol) were added and the reaction was stirred at RT overnight. The mixture was then poured into ice-water (200 mL). The water phase was extracted with EtOAc (200 mL). The organic phase was combined and concentrated. The crude product was redissolved in EtOAc (200 mL), washed with water (200 mL), brine (200 mL), dried by MgSO$_4$, filtered and the solvent was evaporated under reduced pressure. The resulting crude was filtered through an one inch silica gel pad, rinsed with a mixture of EtOAc and Hexane (1:1, 500 mL), and concentrated to afford the title product.

Step B: 2-(3,3-Difluorocyclobutyl)acetonitrile

To a 100 mL round flask, the intermediate from Step A (5 g, 18.10 mmol), sodium cyanide (0.976 g, 19.91 mmol) and DMSO (36.2 mL) were added. The reaction was flushed with nitrogen for 2 min and heated to 90° C. for 5 h. The reaction was cooled down to RT. Ether (50 mL) and water (50 mL) were added and the resulting mixture was stirred for 10 min. The ether layer was washed with brine (50 mL×2), dried by MgSO$_4$, filtered and concentrated to afford title compound.

Step C: Propyl 2-(3,3-difluorocyclobutyl)acetate

To a 40 mL microwave vial, the intermediate from Step B (3.3 g, 70% w/w, 9.61 mmol) and propanol (19.22 ml) were added. HCl gas was bubbled through the reaction mixture for 20 min. The reaction vial was sealed and was heated to 90° C. for 1.5 h. The reaction was cooled down to RT, filtered, and rinsed with ether. The filtrate was concentrated in vacuo to afford title compound.

Step D: 6-((3,3-Difluorocyclobutyl)methyl)-1-methyl-1H-pyrazolo[3,4-d]pyrimidine-4-carboximidamide The title compound was prepared using the intermediate from Step C and 5-amino-1-methyl-1H-pyrazole-4-carboxamide according to the procedure described in Step C to Step F of Example 1.

Step E: 4-Amino-2-(6-((3,3-difluorocyclobutyl)methyl)-1-methyl-1H-pyrazolo[3,4-d]pyrimidin-4-yl)-5-(4-fluorophenyl)-5-methyl-5H-pyrrolo[2,3-d]pyrimidin-6(7H)-one The title compound was prepared from the intermediate from Step D and Intermediate 1B according to the procedures described in Step D of Example 2. $^1$H NMR (500 MHz, CD$_3$OD): δ 8.93 (1H, s), 7.41 (2H, m), 7.13 (2H, t, J=9.0 Hz), 4.14 (3H, s), 3.38 (2H, d, J=7.7 Hz), 2.91 (1H, m), 2.77 (2H, m), 2.50 (2H, m), 1.92 (3H, s), m/z=495 (M+1).

EXAMPLE 6

4-Amino-2-(6-(2,3-difluorobenzyl)-1-methyl-1H-pyrazolo[3,4-d]pyrimidin-4-yl)-5-(4-fluorophenyl)-5-methyl-5H-pyrrolo[2,3-d]pyrimidin-6(7H)-one

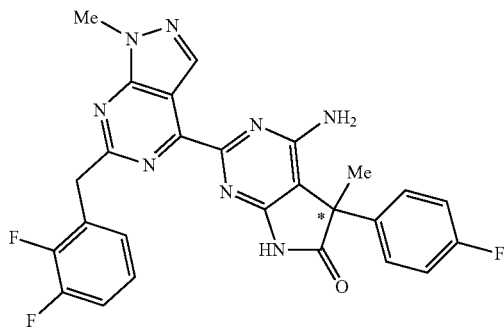 [SMILES: Cn1ncc2c(-c3nc(N)c4c(n3)NC(=O)C4(C)c3ccc(F)cc3)nc(Cc3cccc(F)c3F)nc21]

Step A: 6-(2,3-Difluorobenzyl)-1-methyl-1H-pyrazolo[3,4-d]pyrimidine-4-carboximidamide The title compound was prepared from methyl 2-(2,3-difluorophenyl)acetate and 5-amino-1-methyl-1H-pyrazole-4-carboxamide according to the procedure described in Step C to Step F of Example 1.

Step B: 4-Amino-2-(6-(2,3-difluorobenzyl)-1-methyl-1H-pyrazolo[3,4-d]pyrimidin-4-yl)-5-(4-fluorophenyl)-5-methyl-5H-pyrrolo[2,3-d]pyrimidin-6(7H)-one The title compound was prepared using the intermediate from Step A and Intermediate 1B according to the procedures described in Step G of Example 1. $^1$H NMR (500 MHz, DMSO-d$_6$): δ 11.35 (1H, s), 9.02 (1H, s), 7.35-7.28 (3H, m), 7.20-7.13 (4H, m), 6.85 (2H, s), 4.50 (2H, s), 3.99 (3H, s), 1.80 (3H, s), m/z=517 (M+1).

EXAMPLE 7

4-Amino-2-(1-ethyl-6-(3,3,4,4,4-pentafluorobutyl)-1H-pyrazolo[3,4-d]pyrimidin-4-yl)-5-methyl-5-phenyl-5H-pyrrolo[2,3-d]pyrimidin-6(7H)-one

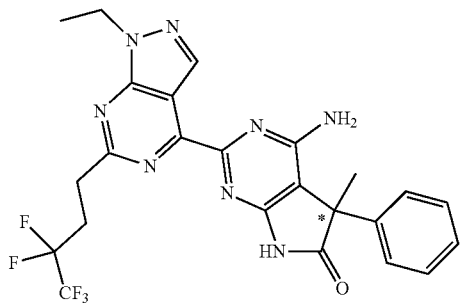 [SMILES: CCn1ncc2c(-c3nc(N)c4c(n3)NC(=O)C4(C)c3ccccc3)nc(CCC(F)(F)C(F)(F)F)nc21]

Step A: 5-Amino-1-ethyl-1H-pyrazole-4-carbonitrile

To a solution of ethyl hydrazine oxalate (10.0 g, 66.6 mmol) in EtOH (150 mL) was added ethoxymethylene malononitrile (8.13 g, 66.6 mmol) and DIEA (8.61 g, 66.6 mmol). The resulting mixture was refluxed for 18 h. The solution was cooled to RT and concentrated in vacuo. The crude product was purified by silica gel chromatography using 0% to 10% MeOH (with 2M NH$_3$) in CH$_2$Cl$_2$ gradient to give the title compound.

Step B: 5-Amino-1-ethyl-1H-pyrazole-4-carboxamide

The title compound was prepared from the intermediate from Step A according to the procedures described in Step B of Example 2.

Step C: 1-Ethyl-6-(3,3,4,4,4-pentafluorobutyl)-1H-pyrazolo[3,4-d]pyrimidine-4-carboximidamide The title compound was prepared from the intermediate from Step B and 4,4,5,5,5-pentafluoropentanoic acid from Step A of Example 1 according to the procedure described in Step A to Step C of Example 4.

Step D: 4-Amino-2-(1-ethyl-6-(3,3,4,4,4-pentafluorobutyl)-1H-pyrazolo[3,4-d]pyrimidin-4-yl)-5-methyl-5-phenyl-5H-pyrrolo[2,3-d]pyrimidin-6(7H)-one The title compound was prepared from the intermediate from Step C and Intermediate 2B according to the procedures described in Step G of Example 1. $^1$H NMR (500 MHz, DMSO-d$_6$): 11.31 (1H, s), 9.00 (1H, s), 7.38-7.25 (5H, m), 6.81 (2H, s), 4.50 (2H, q, J=7.22 Hz), 3.38-3.30 (2H, partially overlapping with H$_2$O), 2.96-2.82 (2H, m), 1.82 (3H, s), 1.45 (3H, t, J=7.22 Hz), m/z=533 (M+1).

EXAMPLE 8

4-Amino-5-(4-fluorophenyl)-5-methyl-2-(6-(3,3,4,4,4-pentafluorobutyl)-1H-pyrazolo[3,4-d]pyrimidin-4-yl)-5H-pyrrolo[2,3-d]pyrimidin-6(7H)-one

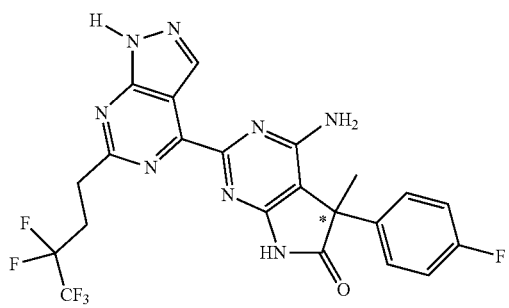 [SMILES: CC1(c2ccc(F)cc2)C(=O)Nc2nc(-c3nc(CCC(F)(F)C(F)(F)F)nc4[nH]ncc34)nc(N)c21]

Step A: 6-(3,3,4,4,4-Pentafluorobutyl)-1H-pyrazolo[3,4-d]pyrimidine-4-carboximidamide The title compound was prepared from the intermediate described in Step B of Example 1 and 5-amino-1H-pyrazole-4-carboxamide according to the procedure described in Step C to Step F of Example 1.

Step B: 4-amino-5-(4-fluorophenyl)-5-methyl-2-(6-(3,3,4,4,4-pentafluorobutyl)-1H-pyrazolo[3,4-d]pyrimidin-4-yl)-5H-pyrrolo[2,3-d]pyrimidin-6(7H)-one The title compound was prepared from the intermediate from Step A and Intermediate 1B according to the procedures described in Step D of Example 2. $^1$H NMR (500 MHz, DMSO-d$_6$): δ 13.99 (1H, s), 11.31 (1H, s), 8.99 (1H, s), 7.30 (2H, dd, J=8.61, 5.37 Hz), 7.17 (2H, t, J=8.75 Hz), 6.80 (2H, br s), 3.39-3.22 (2H, partially overlapping with H$_2$O), 2.84-2.87 (2H, m), 1.80 (3H, s), m/z=523 (M+1).

Using essentially the same procedures described in Examples 1-8, the following compounds in Table 2A were made. Table 2B specifies the intermediate used to make each of Examples 9-27. Where the intermediate used was racemic, the final product was resolved into its S and R enantiomers using the noted technique.

TABLE 2A

| EX | R$^1$ | R$^2$ | R$^4$ | R$^3$ | m/z (M+H) |
|---|---|---|---|---|---|
| 9 | CH$_3$ | CH$_2$CF$_2$CF$_3$ | 4-F-phenyl | CH$_3$ | 537 |
| 10 | CH$_3$ | CH$_2$CF$_2$CF$_3$ | 4-Br-phenyl | CH$_3$ | 597 |
| 11 | CH3 | CH$_2$CF$_3$ | 4-F-phenyl | CH$_3$ | 487 |
| 12 | CD$_3$ | CH$_2$CF$_2$CF$_3$ | CH$_3$ | CH$_3$ | 460 |
| 13 | CD$_3$ | CH$_2$CF$_2$CF$_3$ | phenyl | CH$_3$ | 522 |
| 14 | CD$_3$ | CH$_2$CF$_2$CF$_3$ | 3-OMe-phenyl | CH$_3$ | 552 |
| 15 | CH$_3$ | CH$_2$CH$_2$CF$_3$ | 4-OMe-3-F-phenyl | CH$_3$ | 531 |
| 16 | CH$_3$ | CH$_2$CF$_2$CF$_3$ | 4-OMe-3-F-phenyl | CH$_3$ | 567 |
| 17 | CD$_3$ | CH$_2$CF$_2$CF$_3$ | cyclopropyl | CH$_3$ | 486 |
| 18 | CH$_3$ | CH$_2$CF$_2$CF$_3$ | cyclohexyl | CH$_3$ | 525 |
| 19 | Et | CH$_2$CF$_2$CF$_3$ | 4-F-phenyl | CH$_3$ | 551 |
| 20 | Et | CH$_2$CH$_2$CF$_3$ | 4-F-phenyl | CH$_3$ | 515 |

TABLE 2A-continued

| EX | R¹ | R² | R⁴ | R³ | m/z (M+H) |
|---|---|---|---|---|---|
| 21 | CH₃ | CH₂CF₂CF₃ | ←C≡CH | CH₃ | 467 |
| 22 | CD₃ | CH₂CF₂CF₃ | ←C≡CH | CH₃ | 470 |
| 23 | CH₃ | CH₂CF₂CF₃ | ←C≡CH | Et | 481 |
| 24 | CH₃ | CH₂CF₂CF₃ | ←C≡CH | cyclopropyl | 493 |
| 25 | CD₃ | CH₂CF₂CF₃ | ←n-butyl | cyclopropyl | 528 |
| 26 | CH₃ | CH₂CF₂CF₃ | CO₂Et | cyclopropyl | 541 |
| 27 | CH₃ | CH₂CH₂CF₃ | CO₂Et | cyclopropyl | 505 |

TABLE 2B

| EX | Chiral Source | Characterizaton Data |
|---|---|---|
| 9 | Intermediate 1B | ¹H NMR (500 MHz, DMSO-d₆): δ 11.32 (1 H, s), 9.01 (1 H, s), 7.30 (2 H, dd, J = 8.53, 5.44 Hz), 7.17 (2 H, t, J = 8.71 Hz), 6.83 (2 H, s), 407 (3 H, s), 3.40-3.21 (2 H, partially overlapping with H₂O), 2.95-2.81 (2 H, m), 1.81 (3 H, s). |
| 10 | Intermediate 4A | ¹H NMR (300 MHz, CD₃OD): δ 8.40 (1 H, s), 7.54 (2 H, dd, J = 6.6, 1.8 Hz), 7.30 (2 H, dd, J = 6.6, 2.1 Hz), 4.14 (3 H, s), 3.51-3.45 (2 H, m), 3.00-2.82 (2 H, m), 1.90 (3 H, s). |
| 11 | Intermediate 1B | ¹H NMR (500 MHz, DMSO-d₆): δ 11.31 (1 H, s), 9.01 (1 H, s), 7.30 (2 H, dd, J = 8.62, 5.40 Hz), 7.17 (2 H, t, J = 8.77 Hz), 6.82 (2 H, s), 4.07 (3 H, s), 3.36-3.22 (2 H, partially overlapping with H₂O), 2.98-2.87 (2 H, m), 1.80 (3 H, s), |
| 12 | Not applicable | ¹H NMR (500 MHz, DMSO-d₆): δ 11.15 (1 H, s), 8.98 (1 H, s), 7.01 (2 H, s), 3.37-3.30 (2 H, partially overlapping with H₂O), 2.94-2.79 (2 H, m), 1.37 (6 H, s). |
| 13 | Intermediate 2B | ¹H NMR (500 MHz, DMSO-d₆): δ 11.30 (1 H, s), 9.02 (1 H, s), 7.40-7.21 (5 H, m), 6.79 (2 H, s), 3.38-3.21 (2 H, partially overlapping with H₂O), 2.95-2.83 (2 H, m), 1.81 (3 H, s). |
| 14 | Racemic Intermediate 14 | ¹H NMR (500 MHz, DMSO-d₆): δ 11.30 (2 H, s), 9.01 (1 H, s), 7.25 (1 H, t, J = 7.98 Hz), 6.91-6.59 (5 H, m), 3.74 (3 H, s), 3.50-3.20 (2 H, overlapping with H₂O) 2.94-2.82 (2 H, m), 1.79 (3 H, s). Product resolved using Chiralpak AS. |
| 15 | Racemic Intermediate 17 | ¹H NMR (300 MHz, CDCl₃): δ 8.86 (1 H, s), 8.70 (1 H, s), 6.89-7.13 (3 H, m), 5.00 (1 H, br s), 4.16 (3 H, s), 3.89 (3 H, s), 3.26 (2 H, s), 2.23 (4 H, br s), 1.87 (3 H, s). Product resolved using Chiralpak AD-H |
| 16 | Racemic Intermediate 17 | ¹H NMR (300 MHz, CDCl₃): δ 10.23 (1 H, s), 8.68 (1 H, s), 6.90-7.12 (3 H, m), 4.97 (2 H, s), 4.14 (3 H, s), 3.87 (3 H, s), 3.39-3.44 (2 H, m), 2.67-2.85 (2 H, m), 1.84 (3 H, s). Product resolved using Chiralpak AD-H |

TABLE 2B-continued

| EX | Chiral Source | Characterizaton Data |
|---|---|---|
| 17 | Racemic Intermediate 19 | $^1$H NMR (500 MHz, DMSO-$d_6$): δ 11.06 (1 H, s), 9.00 (1 H, s), 6.98 (2 H, s), 3.50-3.20 (2 H, overlapping with H$_2$O), 2.93-2.80 (2 H, m), 1.46 (3 H, s), 1.41-1.35 (1 H, m), 0.57-0.52 (1 H, m), 0.42-0.33 (2 H, m), 0.20-0.15 (1 H, t, J = 6.75 Hz), Product resolved using Chiralcel OD |
| 18 | Racemic Intermediate 12 | $^1$H NMR (500 MHz, CD$_3$OD): δ 8.89 (1 H, s), 4.09 (3 H, s), 3.45-3.27 (2 H, m), 2.95-2.77 (2 H, m), 2.05-1.98 (1 H, m), 1.88-1.43 (10 H, m). Product resolved using Chiralpak IA |
| 19 | Intermediate 1B | $^1$H NMR (500 MHz, DMSO-$d_6$): δ 11.31 (1 H, s), 9.00 (1 H, s), 7.30 (2 H, dd, J = 8.56, 5.33 Hz), 7.17 (2 H, t, J = 8.71 Hz), 4.49 (2 H, q, J = 7.23 Hz), 3.40-3.25 (2 H, overlapping with H$_2$O), 2.86-2.89 (2 H, m), 1.80 (3 H, s), 1.45 (3 H, t, J = 7.22 Hz). |
| 20 | Intermediate 1B | $^1$H NMR (500 MHz, DMSO-$d_6$): δ 11.32 (1 H, s), 8.98 (1 H, s), 7.30 (2 H, dd, J = 8.61, 5.34 Hz), 7.17 (2 H, t, J = 8.74 Hz), 4.48 (2 H, q, J = 7.23 Hz), 3.14 (2 H, t, J = 7.62 Hz), 2.53-2.36 (2 H, m), 2.08 (2 H, t, J = 7.99 Hz), 1.80 (3 H, s), 1.45 (3 H, t, J = 7.22 Hz). |
| 21 | Racemic Intermediate7 | $^1$H NMR (500 MHz, DMSO-$d_6$): δ 11.51 (1 H, s), 8.98 (1 H, s), 7.15 (2 H, br s), 4.08 (3 H, s), 3.40 (1 H, s), 3.37-3.27 (2 H, overlapping with H$_2$O), 2.87-2.90 (2 H, m), 1.66 (3 H, s). Product resolved using Chiralpak AD-H |
| 22 | Racemic Intermediate7 | $^1$H NMR (500 MHz, CD$_3$OD): δ 8.94 (1 H, s), 3.48-3.49 (3 H, m), 2.93-2.89 (3 H, m), 1.77 (3 H, s). Product resolved using Chiralpak IC |
| 23 | Racemic Intermediate 8 | $^1$H NMR (500 MHz, DMSO-d6): δ 11.51 (1 H, s), 9.01 (1 H, s), 7.14 (2 H, br s), 4.08 (3 H, s), 3.40 (1 H, s), 3.37-3.28 (2 H, overlapping with H$_2$O), 2.87-2.90 (2 H, m), 2.37-2.38 (1 H, m), 2.07 (1 H, dt, J = 14.01, 7.26 Hz), 0.69 (4 H, t, J = 7.37 Hz). Product resolved using Chiralpak IC |
| 24 | Racemic Intermediate 8 | $^1$H NMR (500 MHz, DMSO-$d_6$): δ 11.47 (1 H, s), 9.02 (1 H, s), 6.72 (2 H, br s), 4.06 (3 H, s), 3.41 (1 H, s), 3.37-3.27 (2 H, overlapping with H$_2$O), 2.90-2.82 (2 H, m), 1.32-1.34 (1 H, m), 0.80-0.82 (1 H, m), 0.50-0.52 (3 H, m). Product resolved using Chiralcel OD-H |
| 25 | Racemic Intermediate 18 | $^1$H NMR (500 MHz, DMSO-$d_6$): δ 11.11 (1 H, s), 9.03 (1 H, s), 7.00 (2 H, s), 3.36-3.30 (2 H, m, partially overlapping with H$_2$O), 2.95-2.81 (2 H, m), 2.44-2.34 (1 H, m), 1.86-1.77 (1 H, m), 1.44-0.37 (12 H, m). Product resolved using Chiralpak IC |
| 26 | Intermediate 10 | $^1$H NMR (300 MHz, CDCl$_3$): δ 9.10(s, 1H), 8.65 (1 H, s), 6.36 (1 H, br), 4.33-4.20 (2 H, m), 4.14 (3 H, s), 3.55-3.50 (2 H, m), 2.91-2.73 (2 H, m), 1.77-1.74 (1 H, m), 1.28-1.23 (3 H, m), 0.68-0.57 (4 H, m). Product resolved using Chiralpak AD-H |
| 27 | Intermediate 10 | $^1$H NMR (400 MHz, CDCl$_3$): δ 8.65 (1H, s), 7.28 (1 H, s), 5.82 (1 H, s), 5.37-4.25 (2 H, m), 4.18 (3 H, s), 3.32-3.28 (2 H, t, J = 6.8 Hz), 2.30 (4 H, m), 1.84-1.77 (1 H, m), 1.31-1.28 3 H, t, J = 6.8 Hz), 0.90 (1 H, m), 0.72 (3 H, m). Product resolved using Chiralpak IC |

EXAMPLE 28

4-Amino-N,5-dicyclopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide and the S and R enantiomers thereof

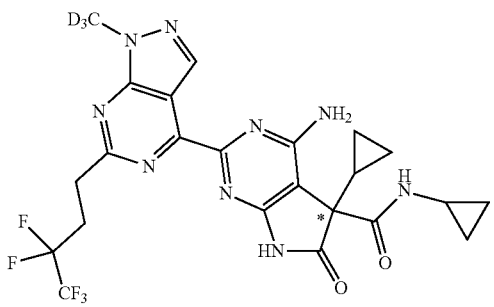 [SMILES: [2H]C([2H])([2H])n1ncc2c(-c3nc(N)c4c(n3)NC(=O)C4(C(=O)NC3CC3)C3CC3)nc(CCC(F)(F)C(F)(F)F)nc21]

Step A: Ethyl 4-amino-5-cyclopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxylate The title compound was prepared from the intermediate as described in Step C of Example 2 and Intermediate 11 according to the procedure described in Step D of Example 2.

Step B: 4-Amino-N,5-dicyclopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide The intermediate from Step A (0.137 g, 0.252 mmol) in cyclopropylamine (2 mL) was heated at 70° C. for 8 h. The reaction solution was then concentrated in vacuo and the residue was purified by reverse phase HPLC using water/acetonitrile (0.1% TFA) to give the title product. Chiral separation using SFC on a Chiralpak AD column provided both enantiomers of the title compound. $^1$H NMR (500 MHz, DMSO-$d_6$): δ 11.32 (1H, s), 8.99 (1H, s), 7.74 (1H, s), 7.13 (2H, s), 3.35-3.28 (2H, partially overlapping with H$_2$O), 2.93-2.80 (2H, m), 2.74-2.68 (1H, m), 1.78-1.71 (1H, m), 0.69-0.61 (2H, m), 0.54-0.44 (4H, m), 0.39-0.31 (2H, m). m/z=555 (M+1).

EXAMPLE 29

4-Amino-5-cyclopropyl-N-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide and the S and R enantiomers thereof

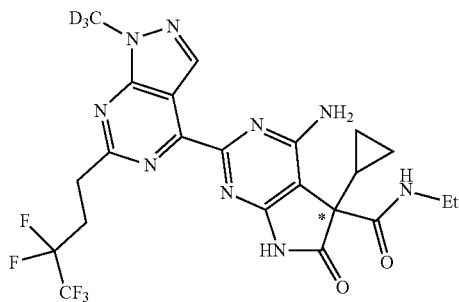 [SMILES: [2H]C([2H])([2H])n1ncc2c(-c3nc(N)c4c(n3)NC(=O)C4(C(=O)NCC)C3CC3)nc(CCC(F)(F)C(F)(F)F)nc21]

To the intermediate from Step A of Example 28 (0.126 g, 0.232 mmol) was added EtNH$_2$ (2.0 mL, 7 M in THF) and the resulting mixture was heated at 50° C. for 3 h. The reaction solution was then concentrated in vacuo and the residue was purified on silica gel eluting with a 0% to 100% EtOAc in hexanes gradient to afford the title product. Chiral separation using SFC on a Chiralpak AD column provided both enantiomers of the title compound. $^1$H NMR (500 MHz, DMSO-d$_6$): δ 11.43 (1H, br s), 8.98 (1H, s), 7.80 (1H, s), 7.22 (2H, s), 3.37-3.26 (2H, m, overlapping with H$_2$O), 3.16-3.18 (2H, m), 2.87 (2H, t, J=9.30 Hz), 1.71-1.72 (1H, m), 1.04 (3H, t, J=7.16 Hz), 0.48-0.50 (2H, m), 0.41-0.43 (1H, m), 0.33-0.36 (1H, m).

EXAMPLE 30

4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide and the S and R enantiomers thereof

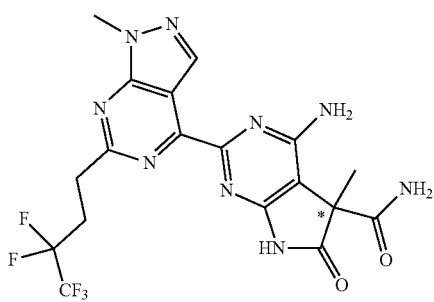 [SMILES: Cn1ncc2c(-c3nc(N)c4c(n3)NC(=O)C4(C)C(N)=O)nc(CCC(F)(F)C(F)(F)F)nc21]

Step A: Ethyl 4-amino-5-methyl-2-(1-methyl-6-(3,3,4,4,4-pentafluorobutyl)-H-pyrazolo[3,4-d]pyrimidin-4-yl)-6-oxo-6,7-dihydro-5H-pyrrolo[2,3-d]pyrimidine-5-carboxylate The title compound was prepared from the intermediate described in Step F of Example 1 and Intermediate 3 according to the procedures described in Step D of Example 2.

Step B: 4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide A 7 M solution of ammonia in MeOH (3.0 mL, 21.0 mmol) was added to the intermediate from Step A (0.100 g, 0.194 mmol) and the resulting mixture was heated at 50° C. for 18 h. The reaction solution was then concentrated in vacuo and the residue was purified by reverse phase HPLC using water/acetonitrile (0.1% TFA) to give the title product. Chiral separation using SFC on a Chiralpak AD column provided both enantiomers of the title compound. $^1$H NMR (500 MHz, DMSO-d$_6$): δ 11.4 (1H, s), 8.98 (1H, s), 7.45 (1H, s), 7.22 (1H, s), 4.06 (3H, s), 3.33-3.25 (2H, overlapping with H$_2$O), 2.88 (2H, t, J=8.03 Hz), 1.59 (3H, s). m/z=486 (M+1).

Using essentially the same procedures described in the Examples 28-30, the following compounds in Table 3A were made, with Table 3B providing NMR characterization and chiral separation of final products via the noted technique to obtain S and R enantiomers of each product.

TABLE 3A

| EX | R$^1$ | R$^3$ | R$^4$ | m/z (M + H) |
|---|---|---|---|---|
| 31 | CH$_3$ | CH$_3$ | (cyclopropylaminocarbonyl) | 526 |
| 32 | CD$_3$ | CH$_3$ | (cyclopropylaminocarbonyl) | 529 |
| 33 | CH$_3$ | cyclopropyl | (cyclopropylaminocarbonyl) | 552 |
| 34 | CD$_3$ | Et | (cyclopropylaminocarbonyl) | 543 |
| 35 | CD$_3$ | isopropyl | (cyclopropylaminocarbonyl) | ~ |

TABLE 3A-continued

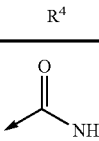

| EX | R¹ | R³ | R⁴ | m/z (M + H) |
|---|---|---|---|---|
| 36 | CD₃ | Et |  | 503 |
| 37 | CD₃ |  |  | ~ |
| 38 | Et |  | 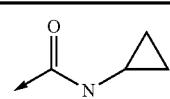 | ~ |
| 39 | CD₃ | CH₃ | 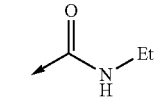 | ~ |

TABLE 3B

| EX | Chiral Source | Characterization Data |
|---|---|---|
| 31 | Chiralcel OD | ¹H NMR (500 MHz, DMSO-d₆): δ 11.32 (1 H, s), 8.99 (1 H, s), 7.65 (1 H, s), 6.93 (2 H, s), 4.06 (3 H, s), 3.42-3.21 (2 H, overlapping with H₂O), 2.92-2.80 (2 H, m), 2.67-2.60 (1 H, m), 1.57 (3 H, s), 0.61-0.57 (2 H, m), 0.47-0.44 (2 H, m). |
| 32 | Chiralcel OD | ¹H NMR (500 MHz, DMSO-d₆): δ 11.35 (1 H, s), 8.99 (1 H, s), 7.64 (1 H, s), 6.95 (2 H, s), 3.42-3.21 (2 H, overlapping with H₂O), 2.93-2.80 (2 H, m), 2.67-2.61 (1 H, m), 1.57 (3 H, s), 0.59-0.56 (2 H, m), 0.47-0.42 (2 H, m). |
| 33 | Chiralpak AD-H | ¹H NMR (500 MHz, DMSO-d₆): δ 11.42 (1 H, br s), 8.99 (1 H, s), 7.72 (1 H, s), 7.15 (2 H, br s), 4.07 (3 H, s), 3.43-3.25 (2 H, partially overlapping with H₂O), 2.90-2.87 (2 H, m), 2.72-2.69 (1 H, m), 1.78-1.71 (1 H, m), 0.65 (2 H, t, J = 6.84 Hz), 0.48-0.51 (4 H, m), 0.33-0.37 (2 H, m). |
| 34 | Chiralpak AD | ¹H NMR (500 MHz, CD₃OD): δ 8.90 (1 H, s), 4.60 (s, 3 H), 3.45-3.47 (2 H, m), 2.87-2.90 (2 H, m), 2.72 (1 H, tt, J = 7.21, 3.86 Hz), 2.42-2.34 (1 H, m), 2.26 (1 H, dt, J = 13.94, 7.17 Hz), 0.82-0.72 (5 H, m), 0.60-0.51 (2 H, m). |
| 35 | Chiralpak AD | ¹H NMR (500 MHz, CD₃OD): δ 8.90 (1 H, s), 4.59 (3 H, s), 3.46 (2 H, t, J = 8.08 Hz), 2.93-2.83 (3 H, m), 2.78-2.71 (1 H, m), 1.13 (3 H, d, J = 6.72 Hz), 0.88 (3 H, d, J = 6.91 Hz), 0.83-0.75 (2 H, m), 0.63-0.53 (2 H, m). |
| 36 | Chiralpak AD | ¹H NMR (500 MHz, CD₃OD): δ 8.89 (1 H, s), 4.59 (3 H, s), 3.49-3.42 (2 H, m), 2.93-2.82 (2 H, m), 2.42 (1 H, dt, J = 13.88, 7.28 Hz), 2.29 (1 H, dd, J = 13.97, 7.28 Hz), 0.82 (3 H, t, J = 7.32 Hz). |
| 37 | Chiralpak AD | ¹H NMR (500 MHz, CD₃OD): δ 8.91 (1 H, s), 4.59 (3 H, s), 3.51-3.42 (2 H, m), 2.96-2.83 (3 H, m), 1.19 (3 H, d, J = 6.74 Hz), 0.91 (3 H, d, J = 6.94 Hz). |
| 38 | Chiralpak AD-H | ¹H NMR (500 MHz, DMSO-d₆): δ 11.37 (1 H, br s), 8.97 (1 H, s), 7.72 (1 H, s), 7.14 (2 H, s), 4.49 (2 H, q, J = 7.23 Hz), 3.38-3.28 (2 H, partially overlapping with H₂O), 2.93-2.79 (2 H, m), 2.73-2.68 (1 H, m), 1.74 (1 H, m), 1.44 (3 H, t, J = 7.22 Hz), 0.67-0.60 (2 H, m), 0.55-0.46 (4 H, m), 0.40-0.29 (2 H, m). |
| 39 | Chiralpak AD-H | ¹H NMR (500 MHz, DMSO-d₆): δ 11.40 (1 H, br s), 8.98 (1 H, s), 7.68 (2 H, s), 6.99 (2 H, br s), 3.43-3.28 (2 H, partially overlapping with H₂O), 3.09 (2 H, t, J = 6.90 Hz), 2.92-2.79 (2 H, m) 1.58 (3 H, s), 0.98 (3 H, t, J = 7.15 Hz). |

EXAMPLE 40

4-Amino-N-cyclopropyl-2-(6-(2,3-difluorobenzyl)-1-methyl-1H-pyrazolo[3,4-d]pyrimidin-4-yl)-5-methyl-6-oxo-6,7-dihydro-5H-pyrrolo[2,3-d]pyrimidine-5-carboxamide

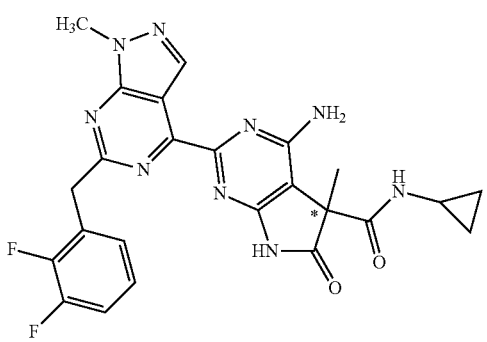 [SMILES: Cn1ncc2c(-c3nc(N)c4c(n3)NC(=O)C4(C)C(=O)NC3CC3)nc(Cc3cccc(F)c3F)nc21]

Step A: Ethyl 4-amino-2-(6-(2,3-difluorobenzyl)-1-methyl-1H-pyrazolo[3,4-d]pyrimidin-4-yl)-5-methyl-6-oxo-6,7-dihydro-5H-pyrrolo[2,3-d]pyrimidine-5-carboxylate The title compound was prepared from the intermediate described in Step A of Example 6 and Intermediate 3 according to the procedures described in Step D of Example 2. Chiral separation using SFC on a Chiralpak AD column provided both enantiomers of the title compound.

Step B: 4-Amino-N-cyclopropyl-2-(6-(2,3-difluorobenzyl)-1-methyl-1H-pyrazolo[3,4-d]pyrimidin-4-yl)-5-methyl-6-oxo-6,7-dihydro-5H-pyrrolo[2,3-d]pyrimidine-5-carboxamide The title compound was prepared from the intermediate (faster eluting enantiomer) in Step A according to the procedure described in Step B of Example 28. $^1$H NMR (500 MHz, DMSO-$d_6$): δ 11.39 (1H, br s), 9.01 (1H, s), 7.66 (1H, d, J=3.91 Hz), 7.32 (1H, d, J=9.32 Hz), 7.20-7.06 (2H, m), 4.49 (2H, s), 3.98 (3H, s), 2.68-2.60 (1H, m), 1.57 (3H, s), 0.63-0.55 (2H, m), 0.44-0.47 (2H, m), m/z=506 (M+1).

EXAMPLE 41

4-Amino-5-cyclopropyl-2-(6-(3,3,4,4,4-pentafluorobutyl)-1-trideuteriomethyl-1H-pyrazolo[3,4-d]pyrimidin-4-yl)-6-oxo-N-(pyridin-2-yl)-6,7-dihydro-5H-pyrrolo[2,3-d]pyrimidine-5-carboxamide and the S and R enantiomers thereof

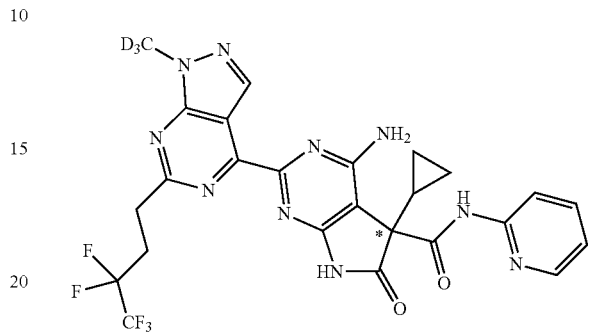

Trimethylaluminum (2.0M in toluene, 1.6 mL, 3.13 mmol) was added dropwise to a solution of 2-aminopyridine (0.294 g, 3.13 mmol) in 4 mL toluene at 0° C. The solution was then stirred at RT for 4 h. This solution was added to the intermediate described in Step A of Example 28 (0.170 g, 0.313 mmol) and the mixture was heated at 80° C. for 5 h. The reaction mixture was cooled to RT, quenched with 6N NaOH, and extracted with EtOAc. The organic phase was washed with brine, dried with MgSO$_4$, filtered, and concentrated in vacuo. Purification by reverse phase HPLC using water/acetonitrile (0.1% TFA) gave the title compound. Chiral separation using SFC on a Chiralpak IC column provided both enantiomers of the title compound. $^1$H NMR (500 MHz, DMSO-$d_6$): δ 11.73 (1H, s), 9.95 (1H, s), 9.01 (1H, s), 8.36 (1H, d, J=4.82 Hz), 8.09 (1H, d, J=8.36 Hz), 7.88-7.83 (1H, m), 7.31 (2H, s), 7.20 (1H, dd, J=7.33, 4.95 Hz), 3.35-3.28 (2H, partially overlapping with H$_2$O), 2.94-2.81 (2H, m), 2.03-1.91 (1H, m), 0.65-0.53 (3H, m), 0.43-0.37 (1H, m). m/z=592 (M+1).

EXAMPLE 42

4-amino-5-methyl-N-(1-methyl-1H-pyrazol-4-yl)-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide and the S and R enantiomers thereof

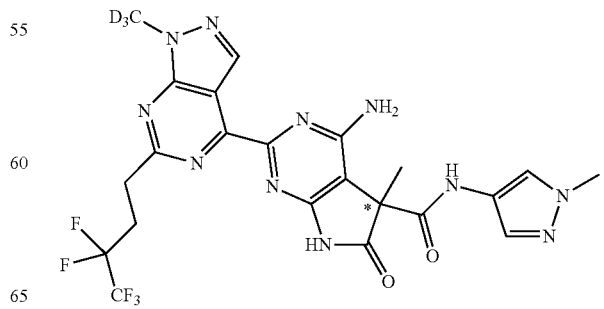

Step A: Ethyl 4-amino-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxylate The title compound was prepared from the intermediate described in Step C of Example 2 and Intermediate 3 according to the procedures described in Step D of Example 2.

Step B: 4-Amino-5-methyl-N-(1-methyl-1H-pyrazol-4-yl)-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide The title compound was prepared from the intermediate from Step A and 1-methyl-1H-pyrazol-4-amine according to the procedure described for Example 41.

Chiral separation using SFC on a Chiralpak AD-H column provided both enantiomers of the title compound. $^1$H NMR (500 MHz, DMSO-$d_6$): δ 11.46 (1H, s), 9.61 (1H, s), 9.00 (1H, s), 7.87 (1H, s), 7.46 (1H, s), 6.95 (2H, s), 3.76 (3H, s), 3.36-3.25 (2H, partially overlapping with H$_2$O), 2.95-2.82 (2H, m), 1.67 (3H, s). m/z=569 (M+1).

EXAMPLE 43

4-Amino-5-(4-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one

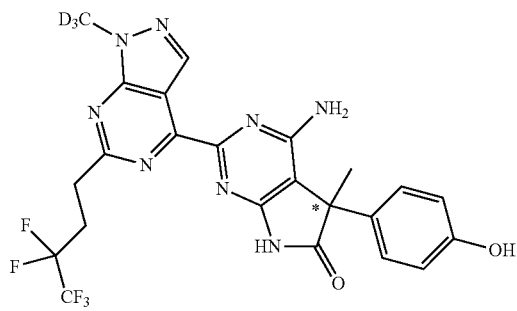 [SMILES: [2H]C([2H])([2H])n1ncc2c(-c3nc(N)c4c(n3)NC(=O)C4(C)c3ccc(O)cc3)nc(CCC(F)(F)C(F)(F)F)nc21]

Step A: 4-Amino-5-(4-methoxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one The indicated compound was prepared from the intermediate described in Step C of Example 2, and Intermediate 13B according to the procedure described in Step D of Example 2. Chiral separation using SFC on a Chiralcel OJ column provided both enantiomers of the title compound.

Step B: 4-Amino-5-(4-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one BBr$_3$ (1.45 mL, 1.45 mmol, 1M in DCM) was added to a DCM solution (1 mL) containing faster eluting enantiomer of Step A (40 mg, 0.072 mmol) and the resulting solution was stirred for 1 h. DCM was removed and the resulting material was dissolved in dioxane and purified by reverse phase HPLC using water/acetonitrile (0.1% TFA) to give the title product. $^1$H NMR (500 MHz, DMSO-$d_6$): δ 11.21 (1H, s), 9.39 (1H, s), 9.01 (1H, s), 7.06 (2H, d, J=8.34 Hz), 6.72 (4H, m, a doublet with J=8.34 Hz overlapping with a broad singlet), 3.36-3.25 (2H, partially overlapping with H$_2$O), 2.94-2.81 (2H, m), 1.75 (3H, s). m/z=538 (M+1).

EXAMPLE 44

4-Amino-5-(3-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one

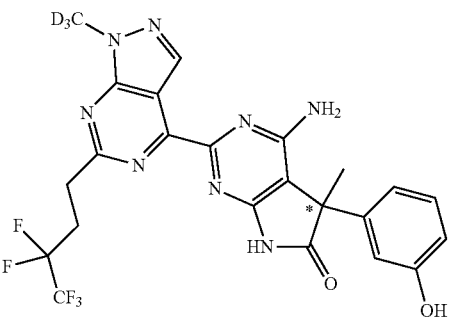 [SMILES: [2H]C([2H])([2H])n1ncc2c(-c3nc(N)c4c(n3)NC(=O)C4(C)c3cccc(O)c3)nc(CCC(F)(F)C(F)(F)F)nc21]

The title compound was prepared from Example 14 according to the procedures described in Step B of Example 43. $^1$H NMR (500 MHz, DMSO-$d_6$): δ 8.97 (1H, s), 7.08 (1H, t, J=7.82 Hz), 6.71-6.59 (5H, m, overlapping with a broad singlet), 3.36-3.25 (2H, overlapping with H$_2$O), 2.95-2.82 (6H, m), 1.66 (3H, s). m/z=538 (M+1).

EXAMPLE 45

5-(4-(1,3,4-Oxadiazol-2-yl)phenyl)-4-amino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one

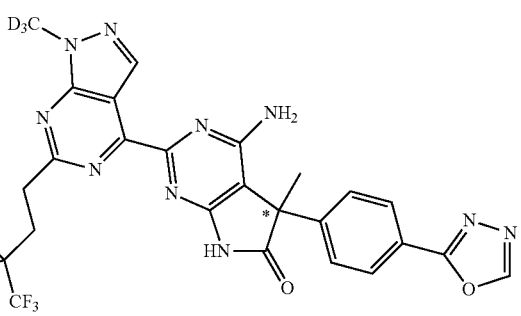

Step A: Ethyl 4-(4-amino-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidin-5-yl)benzoate The title compound was prepared from the intermediate described in Step C of Example 2 and Intermediate 14B according to the procedure described in Step D of Example 2.

Step B: 4-(4-Amino-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidin-5-yl)benzohydrazide Hydrazine hydrate (0.12 mL, 2.53 mmol) was added to a MeOH (4 mL) solution of the intermediate (0.030 g, 0.051 mmol) from Step A. The mixture was heated at 70° C. for 2 h, cooled to RT, and concentrated in vacuo to give the title compound.

Step C: 5-(4-(1,3,4-Oxadiazol-2-yl)phenyl)-4-amino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one A mixture of the intermediate from Step B (0.050 g, 0.086 mmol) and formic acid (4.0 mL, 105 mmol) in CH$_3$CN (4 mL) was stirred at 80° C. for 3 h, cooled to RT, and concentrated in vacuo. Polyphosphoric acid (5 mL) was then added. The resulting mixture was heated at 125° C. for 5 h and cooled to RT. Water (5 mL) was added and followed by adding solid K$_2$CO$_3$ until the pH was 7. The material was extracted with EtOAc. The organic layer was dried, filtered, and concentrated in vacuo. The crude product was purified by reverse phase HPLC using water/acetonitrile (0.1% TFA) to give the title compound. $^1$H NMR (500 MHz, DMSO-d$_6$): δ 11.40 (1H, s), 9.34 (1H, s), 9.03 (1H, s), 8.02 (2H, d, J=8.25 Hz), 7.51 (2H, d, J=8.27 Hz), 6.89 (2H, s), 3.39-3.31 (2H, m, partially overlapping with H$_2$O), 2.95-2.82 (2H, m), 1.87 (3H, s). m/z=590 (M+1).

EXAMPLE 46

4-Amino-5-methyl-5-(4-(1-methyl-1H-pyrazol-4-yl)phenyl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one

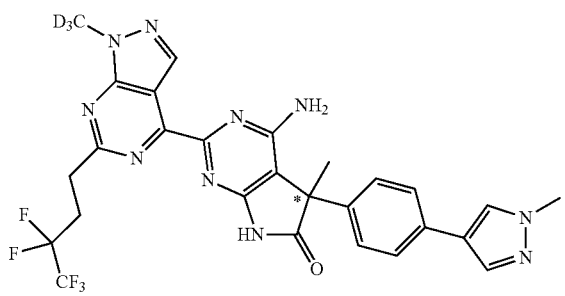 [SMILES: [2H]C([2H])([2H])n1ncc2c(-c3nc(N)c4c(n3)NC(=O)C4(C)c3ccc(-c4cnn(C)c4)cc3)nc(CCC(F)(F)C(F)(F)F)nc21]

Step A: 4-Amino-5-(4-iodophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one The indicated compound was prepared from the intermediate described in Step C of Example 2 and Intermediate 9B according to the procedure described in Step D of Example 2.

Step B: 4-Amino-5-methyl-5-(4-(1-methyl-1H-pyrazol-4-yl)phenyl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one The intermediate from step A (20 mg, 0.031 mmol), chloro(2-dicyclohexylphosphino-2',4',6'-triisopropyl-1,1'-biphenyl)[2-(2'-amino-1,1'-biphenyl)]palladium(II) (4.9 mg, 6.2 μmol), and 1-methyl-4-(4,4,5,5,-tetramethyl-1,3,2-dioaborolan-2-yl)-1H-pyrazole (10.0 mg, 0.046 mmol) were weighed out into a 2 dram vial. THF (1 mL) and 0.5 M potassium phosphate (tribasic) solution (0.5 mL, 0.250 mmol) were added in order. The mixture was stirred at RT for 18 h. The crude product was purified by reversed phase HPLC using acetonitrile/pH 10 NH$_4$OH to give the title product. m/z=602 (M+1).

EXAMPLE 47

4-(4-Amino-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidin-5-yl)benzonitrile

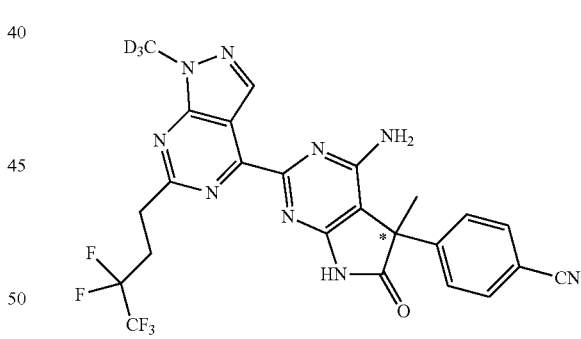

A mixture of intermediate (0.042 mg, 0.065 mmol) described in Step A of Example 46, ZnCN$_2$ (0.008 g, 0.065 mol), Pd$_2$(dba)$_3$ (0.006 g, 0.0065 mmol), dppf (7 mg, 0.013 g) in DMF (2 mL) was stirred at 100° C. for 1 h. The mixture was filtered and the filtrate was concentrated in vacuo. The crude product was purified by reverse phase HPLC using water/acetonitrile (0.1% TFA) to give the title compound. $^1$H NMR (500 MHz, DMSO-d$_6$): δ 11.43 (1H, s), 9.02 (1H, s), 7.83 (2H, d, J=8.22 Hz), 7.48 (2H, d, J=8.22 Hz), 6.92 (2H, br s), 3.40-3.20 (2H, m, partially overlapping with H$_2$O), 2.95-2.82 (2H, m), 1.85 (3H, s). m/z=547 (M+1).

EXAMPLE 48

5-(4-Fluorophenyl)-4-hydroxy-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one

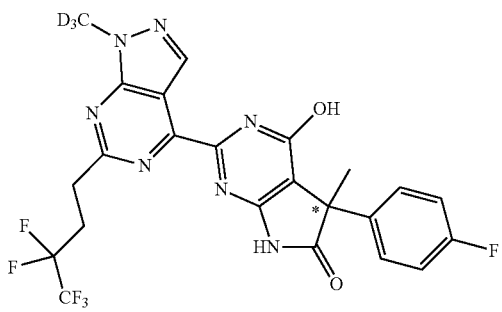 [SMILES: [2H]C([2H])([2H])n1ncc2c(-c3nc(O)c4c(n3)NC(=O)C4(C)c3ccc(F)cc3)nc(CCC(F)(F)C(F)(F)F)nc21]

To 4-amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one (see Example 2) (25 mg, 0.046) in DCE (1.5 mL) was added tert-butyl nitrite (14 mg, 0.14 mmol) and water (3 mg, 0.14 mmol) mmol). The mixture was stirred at 60° C. for 4 h. The mixture was then concentrated in vacuo. The crude product was purified by reverse phase HPLC using water/acetonitrile (0.1% TFA) to give the title compound. $^1$H NMR (500 MHz, DMSO-$d_6$): δ 12.90 (1H, br s), 11.25 (1H, br s), 8.73 (1H, s), 7.44 (2H, dd, J=8.54, 5.42 Hz), 7.14 (2H, t, J=8.76 Hz), 3.43-3.22 (2H, m, partially overlapping with H$_2$O), 3.11-2.96 (2H, m), 1.73 (3H, s), m/z=541 (M+1).

EXAMPLE 49

4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carbonitrile and the S and R enantiomers thereof

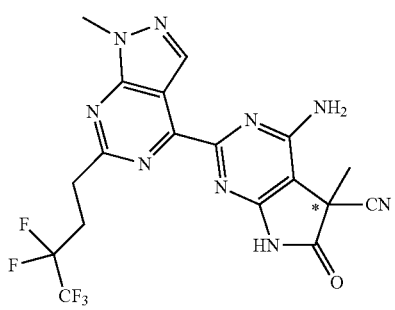 [SMILES: Cn1ncc2c(-c3nc(N)c4c(n3)NC(=O)C4(C)C#N)nc(CCC(F)(F)C(F)(F)F)nc21]

To 4-amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide racemate (see Example 30) (210 mg, 0.433 mmol) in pyridine (8 mL) was added POCl$_3$ (531 mg, 3.47 mmol) dropwise at 0° C. The resulting solution was stirred for 20 min at ambient temperature and concentrated in vacuo. The mixture was quenched by the addition of water/ice. The pH value of the solution was adjusted to 9 with saturated sodium carbonate aqueous solution. The resulting solution was extracted with EtOAc and the organic layers were combined. The resulting mixture was washed with brine, dried over anhydrous sodium sulfate, filtered, and concentrated in vacuo. The crude product was purified by silica gel chromatography using 0 to 15% MeOH in CH$_2$Cl$_2$ gradient to give the title compound. Chiral separation using Prep-HPLC on a Chiralpak IC column provided both enantiomers of the title compound. $^1$H NMR (300 MHz, CD$_3$OD): δ 8.91 (s, 1H), 4.13 (s, 3H), 3.50-3.44 (m, 2H), 2.98-2.80 (m, 2H), 1.91 (s, 3H), m/z=468 (M+1).

EXAMPLE 50

4,5-Diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one

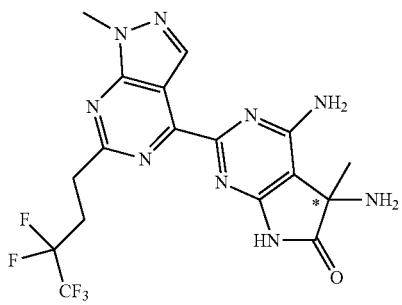 [SMILES: Cn1ncc2c(-c3nc(N)c4c(n3)NC(=O)C4(C)N)nc(CCC(F)(F)C(F)(F)F)nc21]

Step A: 4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carbohydrazide Hydrazine hydrate (0.39 mL, 8.12 mmol) was added to a MeOH (8 mL) solution of the intermediate described in Step A of Example 30 (0.42 g, 0.812 mmol). The mixture was heated at 50° C. for 2 h, cooled to RT, and concentrated in vacuo. The crude product was purified by silica gel chromatography using 0% to 20% MeOH in DCM gradient to give the title compound.

Step B: tert-Butyl (4-amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)carbamate Into a 100-mL 3-necked round-bottom flask purged and maintained with an inert atmosphere of nitrogen, were placed the intermediate from Step A (2.0 g, 4.0 mmol), THF (40 mL) and trifluoroacetic acid (0.52 g, 4.64 mmol, 1.15 equiv). This was followed by the addition of t-butyl nitrite (1.2 g, 11.99 mmol, 3.0 equiv) dropwise with stirring at 0° C. The resulting solution was stirred for 1 h at 0° C., and then concentrated in vacuo. t-Butanol (40 mL) was added at RT and the mixture was stirred at 80° C. for 1 h. The reaction was then quenched by the addition of water. The pH value of the solution was adjusted to 8 with aqueous sodium carbonate (1 N). The resulting solution was extracted with EtOAc, washed with brine, dried over anhydrous sodium sulfate and filtered. The filtrate was concentrated in vacuo to dryness. The residue was purified by silica gel chromatography using MeOH/DCM gradient to give the title compound. Chiral separation using Prep-HPLC on a Chiralpak IC column provided both enantiomers of the title compound.

Step C: 4,5-Diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one To the intermediate from Step B (slower eluting enantiomer) (0.34 g, 0.61 mmol) in DCM (5 mL) was added trifluoroacetic acid (2.5 mL). The resulting solution was stirred for 3 h at RT and concentrated in vacuo. The pH value of the solution was adjusted to 8 with saturated aqueous sodium carbonate solution. The resulting solution was extracted with EtOAc and the organic layers were combined, washed with brine, dried over anhydrous sodium sulfate and filtered. The filtrate was concentrated in vacuo to give the title compound. $^1$H NMR (400 MHz, DMSO-$d_6$): δ 11.12 (1H, br s), 8.97 (1H, s), 6.910 (2H, br s), 4.08 (3H, s), 3.36 (2H, t, J=7.2 Hz), 2.96-2.82 (2H, m), 2.31 (2H, s), 1.39 (3H, s), m/z=458 (M+1).

EXAMPLE 51

N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)picolinamide

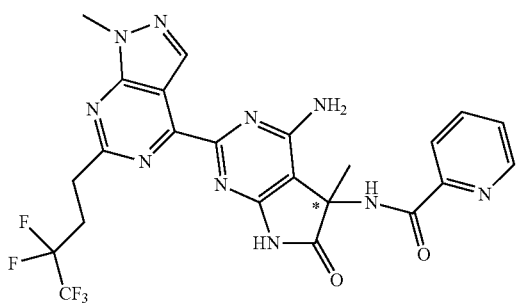 [SMILES: Cn1ncc2c(-c3nc(N)c4c(n3)NC(=O)C4(C)NC(=O)c3ccccn3)nc(CCC(F)(F)C(F)(F)F)nc21]

Into a 8-mL round-bottom flask, were placed a solution of pyridine-2-carboxylic acid (15 mg, 0.12 mmol) in N,N-dimethylformamide (4 mL), N,N,N,N-tetramethyl-O-(7-azabenzotriazol-1-yl)uronium hexafluorophosphate (62 mg, 0.16 mmol) and triethylamine (22 mg, 0.22 mmol). The resulting solution was stirred for 30 min at RT. Then 4,5-diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one (see Example 50) (50 mg, 0.11 mmol) was added. The resulting solution was stirred for 4 h at ambient temperature. The reaction was then quenched by the addition of brine (50 mL). The resulting solution was extracted with EtOAc (3×30 mL) and the organic layers were combined, dried over anhydrous sodium sulfate and filtered. The filtrate was concentrated in vacuo. The residue was purified by silica gel chromatography using EtOAc/petroleum ether gradient to give the title compound. $^1$H NMR (400 MHz, CDCl$_3$): δ 9.47 (1H, s), 8.71-8.59 (3H, m), 8.15 (1H, d, J=8.0 Hz), 7.91-7.87 (1H, m), 7.52-7.49 (1H, m), 6.28 (2H, br s), 4.18 (3H, s), 3.56-3.52 (2H, m), 2.88-2.75 (2H, m), 1.95 (3H, s), m/z=563 (M+1).

EXAMPLE 52

N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)-2-cyclopropylacetamide

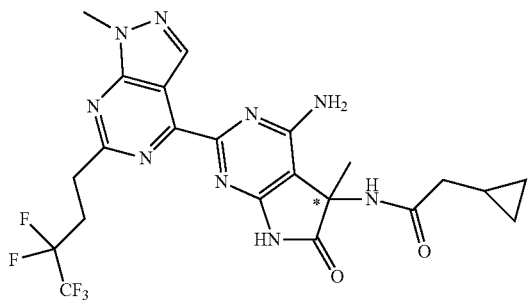 [SMILES: Cn1ncc2c(-c3nc(N)c4c(n3)NC(=O)C4(C)NC(=O)CC3CC3)nc(CCC(F)(F)C(F)(F)F)nc21]

The title compound was prepared from 4,5-diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one (See Example 50) and 2-cyclopropylacetic acid according to the procedures described in Example 51. $^1$H NMR (300 MHz, CDCl$_3$): δ 8 10.59 (1H, br s), 8.53 (1H, s), 6.86 (1H, br s), 6.41 (2H, br s), 4.15 (3H, s), 3.52-3.36 (2H, m), 2.87-2.70 (2H, m), 2.12 (1H, d, J=7.2 Hz), 1.81 (3H, s), 0.97-0.89 (1H, m), 0.62-0.57 (2H, m), 0.20-0.12 (2H, m), m/z=540 (M+1).

EXAMPLE 53

N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)cyclopropanecarboxamide

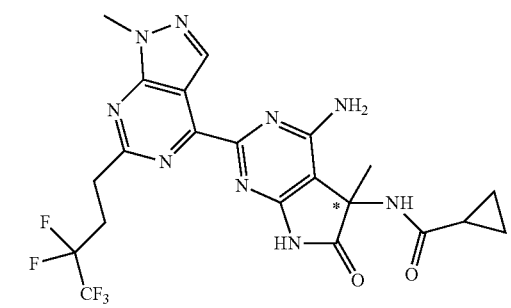 [SMILES: Cn1ncc2c(-c3nc(N)c4c(n3)NC(=O)C4(C)NC(=O)C3CC3)nc(CCC(F)(F)C(F)(F)F)nc21]

The title compound was prepared from 4,5-diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one (see Example 50) and cyclopropanecarboxylic acid according to the procedures described in Example 51. $^1$H NMR (300 MHz, CD$_3$OD): δ 8.91 (1H, s), 4.14 (3H, s), 3.49-3.47 (2H, m), 2.97-2.84 (2H, m), 1.75-1.68 (1H, m), 1.66 (3H, s), 0.86-0.77 (4H, m), m/z=526 (M+1).

EXAMPLE 54

4-Amino-5-((cyclopropylmethyl)amino)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one

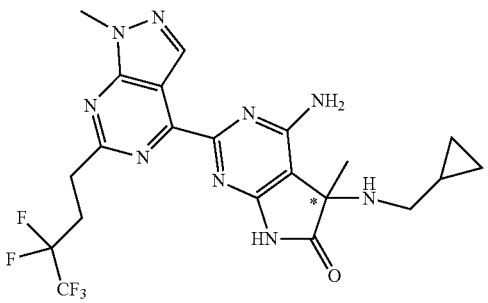 [SMILES: Cn1ncc2c(-c3nc(N)c4c(n3)NC(=O)C4(C)NCC3CC3)nc(CCC(F)(F)C(F)(F)F)nc21]

Into a 8-mL sealed tube, were placed the product of Example 50 (60 mg, 0.13 mmol), 1,2-dichloroethane (6 mL), and cyclopropanecarbaldehyde (15 mg, 0.19 mmol, 1.5 equiv), and the mixture was stirred for 10 min at ambient temperature. To this was added sodium triacetoxyborohydride (110 mg, 0.52 mmol, 4.0 equiv). The resulting mixture was stirred for 16 h at RT and quenched by the addition of water (50 mL). The resulting solution was extracted with DCM (3×50 mL) and the organic layers were combined. The resulting mixture was washed with brine (50 mL), dried over anhydrous sodium sulfate and filtered. The filtrate was concentrated in vacuo. The residue was purified by silica gel chromatography using 0% to 20% MeOH in DCM gradient to afford the title compound. This was further purified by recrystallization from DCM/hexanes. $^1$H NMR (300 MHz, CDCl$_3$): δ 8.73 (2H, br s), 7.73 (1H, s), 5.75 (2H, br s), 4.16 (3H, s), 3.56-3.50 (2H, m), 2.89-2.71 (2H, m), 2.36-2.34 (1H, m), 2.11-2.05 (1H, m), 1.63 (3H, s), 0.92-0.86 (1H, m), 0.55-0.40 (2H, m), 0.15-0.05 (2H, m), m/z=512 (M+1).

EXAMPLE 55

4-Amino-5-(isopropylamino)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one

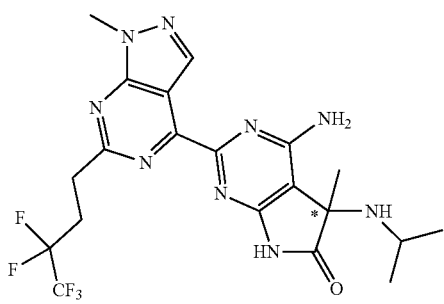 [SMILES: CC(C)NC1(C)C(=O)Nc2nc(-c3nc(CCC(F)(F)C(F)(F)F)nc4c3cnn4C)nc(N)c21]

The title compound was prepared from the product of Example 50 and acetone according to the procedures described in Example 54. $^1$H NMR (300 MHz, CDCl$_3$): δ 8.74 (1H, br s), 8.62 (1H, br), 5.77 (2H, br), 4.17 (3H, s), 3.58-3.52 (2H, m), 2.90-2.65 (3H, m), 1.58 (3H, s), 1.07 (3H, d, J=6.3 Hz), 0.99 (3H, d, J=6.3 Hz), m/z=500 (M+1).

EXAMPLE 56

4-Amino-5-methoxy-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one and the S and R enantiomers thereof

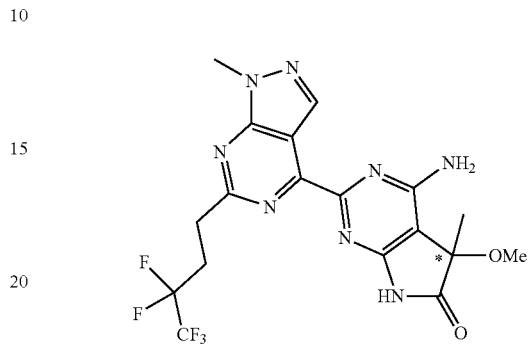

Into a 50-mL sealed tube, were placed 4-amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide (racemate) see Example 30) (170 mg, 0.35 mmol), N-bromosuccinimide (137 mg, 0.77 mmol), MeOH (12 mL) and 1,8-diazabicyclo[5.4.0]undec-7-ene (203 mg, 1.33 mmol). The resulting mixture was stirred for 30 min at 80° C. The reaction progress was monitored by LC/MS (liquid chromatography-mass spectrometry). The reaction was then quenched by the addition of water (100 mL). The resulting solution was extracted with EtOAc (4×50 mL) and the organic layers were combined. The resulting mixture was washed with brine (30 mL), dried over anhydrous sodium sulfate and filtered. The filtrate was concentrated in vacuo to dryness. The residue was purified by silica gel chromatography using EtOAc/petroleum ether gradient to give the title compound. Chiral separation using Prep-HPLC on a Chiralpak IC column provided both enantiomers of the title compound. $^1$H NMR (400 MHz, CDCl$_3$): δ 8.82 (1H, br s), 8.73 (1H, s), 5.85 (2H, br s), 4.20 (3H, s), 3.60-3.52 (2H, m), 3.25 (3H, s), 2.95-2.82 (2H, m), 1.72 (3H, s), m/z=473 (M+1).

EXAMPLE 57

4-Amino-5-methyl-5-trideuteriomethoxy-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one and the S and R enantiomers thereof

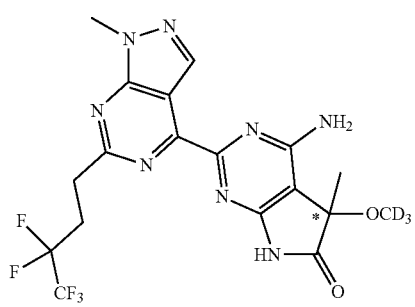

The title compound was prepared from 4-amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide (racemic) (see Example 30) and CD$_3$OD according to the procedures described in Example 56. $^1$H NMR (300 MHz, CDCl$_3$): δ 8.70 (1H, s), 8.61 (1H, br s), 5.85 (2H, br s), 4.18 (3H, s), 3.59-3.54 (2H, m), 2.95-2.77 (2H, m), 1.70 (3H, s), m/z=476 (M+1).

EXAMPLE 58

4-Amino-2-(3-chloro-1-methyl-6-(3,3,4,4,4-pentafluorobutyl)-1H-pyrazolo[3,4-d]pyrimidin-4-yl)-5-(4-fluorophenyl)-5-methyl-5H-pyrrolo[2,3-d]pyrimidin-6(7H)-one

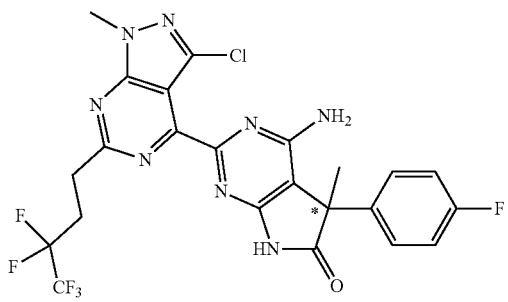 [SMILES: Cn1nc(Cl)c2c(-c3nc(N)c4c(n3)NC(=O)C4(C)c3ccc(F)cc3)nc(CCC(F)(F)C(F)(F)F)nc21]

Step A: 3-Chloro-1-methyl-6-(3,3,4,4,4-pentafluorobutyl)-1H-pyrazolo[3,4-d]pyrimidine-4-carboximidamide A mixture of the intermediate (2.0 g, 6.21 mmol) described in Step F of Example 1, 1,3-dichloro-5,5-dimethylimidazolidine-2,4-dione (2.45 g, 12.41 mmol) and palladium(II) acetate (139 mg, 0.621 mmol) were heated in acetic acid (62 mL) at 100° C. for 18 h in a sealed tube. The mixture was cooled to RT and concentrated. The residue was purified by supercritical fluid chromatography with MeOH as the carrier to afford the title compound.

Step B: 4-Amino-2-(3-chloro-1-methyl-6-(3,3,4,4,4-pentafluorobutyl)-1H-pyrazolo[3,4-d]pyrimidin-4-yl)-5-(4-fluorophenyl)-5-methyl-5H-pyrrolo[2,3-d]pyrimidin-6(7H)-one The title compound was prepared from the intermediate from Step A and Intermediate 1B (slower eluting enantiomer) according to the procedures described in Step D of Example 2. $^1$H NMR (500 MHz, DMSO-d$_6$): δ 11.25 (1H, s), 7.29 (2H, dd, J=8.55, 5.37 Hz), 7.20 (2H, t, J=8.73 Hz), 4.04 (3H, s), 3.38-3.29 (2H, m, overlapping with H$_2$O), 2.93-2.79 (2H, m), 1.81 (3H, s), m/z=571 (M+1).

EXAMPLE 59

4-Amino-2-(3-cyclopropyl-6-(3,3,4,4,4-pentafluorobutyl)-1-trideuteriomethyl-1H-pyrazolo[3,4-d]pyrimidin-4-yl)-5-(4-fluorophenyl)-5-methyl-5H-pyrrolo[2,3-d]pyrimidin-6(7H)-one

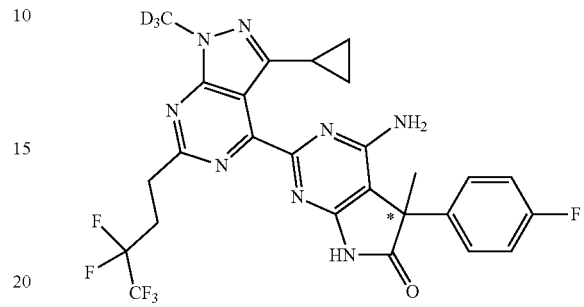

To a 4 mL vial in the glovebox were added 4-amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one (Example 2) (20 mg, 0.037 mmol), potassium cyclopropyltrifluoroborate (44.0 mg, 0.297 mmol), manganese(IV) oxide (25.8 mg, 0.297 mmol), HOAc (200 μl), H$_2$O (60.0 μl), TFA (2.86 μl, 0.037 mmol)) in order. The mixture was heated at 50° C. for 24 h and cooled to RT. Solid NaHCO$_3$ was added until CO$_2$ evolution ceased. The resulting mixture was extracted with extracted with methyl t-butyl ether (10 mL) and the organic layer was concentrated in vacuo. The residue was purified by reverse phase HPLC using acetonitrile in water with 0.1% TFA as the eluent to give the title product as a TFA salt. $^1$H NMR (500 MHz, CDCl$_3$): δ 9.41 (1H, br s), 7.34 (2H, m), 7.14 (2H, m), 5.32 (2H, br s), 3.50 (2H, m), 2.82 (2H, m), 2.37 (1H, m), 1.91 (3H, s), 1.05 (2H, m), 0.92 (2H, m), m/z=580 (M+1).

EXAMPLE 60

4-Amino-5-methyl-2'-(3,3,4,4,4-pentafluorobutyl)-5-phenyl-7'-trideuteriomethyl-5H,7'H-[2,4'-bipyrrolo[2,3-d]pyrimidin]-6(7H)-one

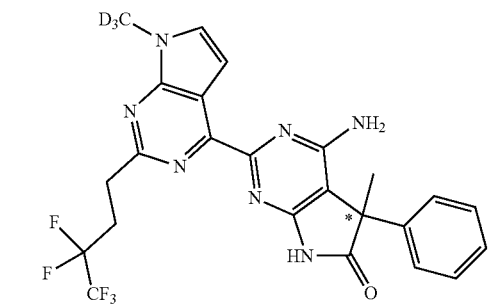 [SMILES: [2H]C([2H])([2H])n1ccc2c(-c3nc(N)c4c(n3)NC(=O)C4(C)c3ccccc3)nc(CCC(F)(F)C(F)(F)F)nc21]

Step A: 4,4,5,5,5-Pentafluoropentanimidamide

Trimethyl aluminum (2.0 M toluene, 32.5 mL, 65.1 mmol) was added to NH$_4$Cl (3.48 g, 65.1 mmol) suspended in toluene (100 mL) at 0° C. The solution was then stirred at RT for 1 h. 4,4,5,5,5-Pentafluoropentanoic acid (2.50 g, 13.0 mmol) described in Step A of Example 1 was added and the resulting mixture was stirred at 100° C. for 18 h. The reaction mixture was cooled to RT and quenched with silica-gel and a 1:1 mixture of MeOH/chloroform (50 mL). The resulting slurry was stirred vigorously for 30 min. The reaction mixture was filtered through a silica gel pad and washed with MeOH. The filtrate was concentrated. The crude product was purified by silica gel chromatography using a 0% to 30% MeOH (with 2M NH$_3$) in DCM gradient to give the title compound Step B: 6-Amino-5-(2,2-diethoxyethyl)-2-(3,3,4,4,4-pentafluorobutyl)pyrimidin-4-ol A mixture of the intermediate from Step A (1.01 g, 5.29 mmol) and NaOEt (0.72 g, 10.6 mmol) in EtOH (20 mL) was stirred at RT for 20 min. A solution of ethyl 2-cyano-4,4-diethoxybutanoate (1.34 g, 5.82 mmol) in 20 mL of EtOH was added and the resulting mixture was refluxed for 18 h. The reaction mixture was cooled to RT, concentrated in vacuo and the residue was diluted with EtOAc. The solution was then washed with water, dried over MgSO$_4$, filtered, and concentrated in vacuo. The crude product was purified by silica gel chromatography using a 0% to 15% MeOH (with 2M NH$_3$) in DCM gradient to give the title compound.

Step C: 2-(3,3,4,4,4-Pentafluorobutyl)-7H-pyrrolo[2,3-d]pyrimidin-4-ol

To a solution of the intermediate from Step B (1.170 g, 3.13 mmol) in 50 mL of EtOH was added TFA dropwise. The resulting mixture was stirred at RT for 18 h and concentrated in vacuo to give the title compound which was used in the next step without further purification.

Step D: 4-Chloro-2-(3,3,4,4,4-pentafluorobutyl)-7H-pyrrolo[2,3-d]pyrimidine

A solution of the intermediate from Step C (0.88 g, 3.13 mmol) in POCl$_3$ (10 mL) was refluxed for 3 h. The resulting mixture was concentrated in vacuo and the residue was diluted with diethyl ether, washed with water, dried over MgSO$_4$, filtered, and concentrated in vacuo. The crude product was purified by silica gel chromatography using a 0% to 70% EtOAc/CH$_2$Cl$_2$ (1/1) mixture in hexanes gradient to give the title compound.

Step E: 4-Chloro-2-(3,3,4,4,4-pentafluorobutyl)-7-trideuteriomethyl-7H-pyrrolo[2,3-d]pyrimidine To a suspension of NaH (0.025 g, 0.629 mmol) in DMF (4 mL) at 0° C. was added dropwise a solution of the intermediate from Step D (0.145 g, 0.484 mmol) in DMF (4 mL). The reaction mixture was stirred at RT for 15 min and then CD$_3$I (0.140 g, 0.968 mmol) was added. The resulting mixture was then stirred at RT for 2 h and partitioned between EtOAc and water. The organic phase was washed with brine, dried with MgSO$_4$, filtered, and concentrated in vacuo. The crude product was purified by silica gel chromatography using a 0% to 30% EtOAc in hexanes gradient to give the title compound.

Step F: 2-(3,3,4,4,4-Pentafluorobutyl)-7-trideuteriomethyl-7H-pyrrolo[2,3-d]pyrimidine-4-carbonitrile To a solution of the intermediate from Step E (0.130 g, 0.411 mmol) in DMF (6 mL) was added zinc cyanide (0.048 g, 0.411 mmol), Pd$_2$dba$_3$ (0.038 g, 0.041 mmol), DPPF (0.046 g, 0.082 mmol). The resulting solution was heated at 100° C. for 1 h. The reaction was cooled to RT, diluted with water (10 mL) and extracted with EtOAc. The organic phase was washed with brine, dried with MgSO$_4$, filtered, and concentrated in vacuo. The crude product was purified by silica gel chromatography using a 0% to 50% EtOAc in hexanes gradient to give the title compound.

Step G: 2-(3,3,4,4,4-Pentafluorobutyl)-7-trideuteriomethyl-7H-pyrrolo[2,3-d]pyrimidine-4-carboximidamide Trimethylaluminum (2.0 M in toluene, 32.8 mL, 65.7 mmol) was added dropwise to a suspension of NH$_4$Cl (3.51 g, 65.7 mmol) in 100 mL toluene cooled to 0° C. The solution was then stirred at RT for 1 h. This solution (7.97 mL, 3.91 mmol) was then added to the intermediate from Step F (0.12 g, 0.391 mmol) and then heated at 110° C. for 18 h. The reaction mixture was cooled to RT and quenched with silica-gel and 1:1 MeOH-chloroform (25 mL). The resulting slurry was stirred vigorously for 30 min. The reaction mixture was filtered through a silica gel pad (1") and washed with MeOH. The filtrate was concentrated in vacuo to yield the title compound.

Step H: 4-Amino-5-methyl-2'-(3,3,4,4,4-pentafluorobutyl)-5-phenyl-7'-trideuteriomethyl-5H,7'H-[2,4'-bipyrrolo[2,3-d]pyrimidin]-6(7H)-one The title compound was prepared from the intermediate from Step G and intermediate 2B (slower eluting enantiomer) according to the procedure described in Step G of Example 1. $^1$H NMR (500 MHz, DMSO-d$_6$): δ 11.23 (1H, s), 7.64 (1H, d, J=3.46 Hz), 7.39-7.34 (3H, m), 7.31 (3H, t, J=7.49 Hz), 6.63 (2H, s), 3.35-3.28 (2H, partially overlapping with H$_2$O), 2.94-2.80 (3H, m), 1.83 (3H, s), m/z=521 (M+1).

EXAMPLE 61

4-Amino-5-(4-fluorophenyl)-5,7'-dimethyl-2'-(3,3,4,4,4-pentafluorobutyl)-5H,7'H-[2,4'-bipyrrolo[2,3-d]pyrimidin]-6(7H)-one

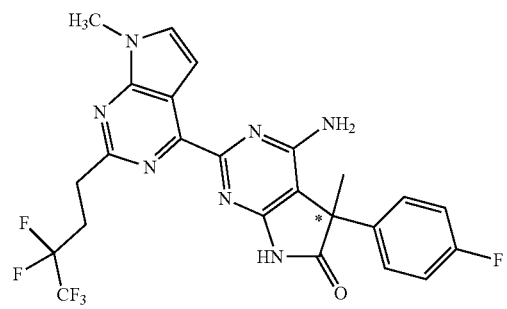 [SMILES: Cn1ccc2c(-c3nc(N)c4c(n3)NC(=O)C4(C)c3ccc(F)cc3)nc(CCC(F)(F)C(F)(F)F)nc21]

Step A: 4-Chloro-7-methyl-2-(3,3,4,4,4-pentafluorobutyl)-7H-pyrrolo[2,3-d]pyrimidine To a suspension of NaH (0.200 g, 4.99 mmol) in DMF (5 mL) at 0° C. was added dropwise a solution of the intermediate (0.748 g, 2.496 mmol) described in Step D of Example 60 in DMF (10 mL). The reaction mixture was stirred at RT for 15 min and then MeI (0.709 g, 4.99 mmol) was added. The resulting mixture was then stirred at RT for 1 h and partitioned between EtOAc and water. The organic phase was washed with brine, dried with MgSO$_4$, filtered, and concentrated in vacuo. The crude product was purified by silica gel chromatography using a 0 to 40% EtOAc in hexanes gradient to give the title compound.

Step B: 7-Methyl-2-(3,3,4,4,4-pentafluorobutyl)-7H-pyrrolo[2,3-d]pyrimidine-4-carbonitrile To a solution of the intermediate from Step A (0.681 g, 2.17 mmol) in DMF (10 mL) was added zinc cyanide (0.255 g, 2.17 mmol), Pd$_2$dba$_3$ (0.199 g, 0.217 mmol), dppf (0.241 g, 0.434 mmol). The resulting solution was heated at 100° C. for 1 h. The reaction was cooled to RT, diluted with water (10 mL) and extracted with EtOAc. The organic phase was washed with brine, dried with MgSO$_4$, filtered, and concentrated in vacuo. The crude product was purified by silica gel chromatography using a 0 to 40% EtOAc in hexanes gradient to give the title compound.

Step C: 7-Methyl-2-(3,3,4,4,4-pentafluorobutyl)-7H-pyrrolo[2,3-d]pyrimidine-4-carboximidamide Trimethylaluminum (2.0 M in toluene, 18.9 mL, 37.8 mmol) was added dropwise to a suspension of NH$_4$Cl (2.02 g, 37.8 mmol) in 55 mL toluene cooled to 0° C. The solution was then stirred at RT for 1 h. This solution (27.9 mL, 14.23 mmol) was then added to the intermediate from Step B (0.541 g, 1.778 mmol) and then heated at 100° C. for 18 h. The reaction mixture was cooled to RT and quenched with silica-gel and 1:1 MeOH-chloroform (25 mL). The resulting slurry was stirred vigorously for 30 min. The reaction mixture was filtered through a silica gel pad (1″) and washed with MeOH. The filtrate was concentrated in vacuo to yield the title compound.

Step D: 4-Amino-5-(4-fluorophenyl)-5,7′-dimethyl-2′-(3,3,4,4,4-pentafluorobutyl)-5H,7′H-[2,4′-bipyrrolo[2,3-d]pyrimidin]-6(7H)-one The title compound was prepared from the intermediate from Step C and intermediate 1B (slower eluting enantiomer) according to the procedures described in Step G of Example 1. $^1$H NMR δ (500 MHz, DMSO-d$_6$): δ 11.24 (1H, s), 7.63 (1H, d, J=3.48 Hz), 7.36-7.28 (3H, m), 7.17 (2H, t, J=8.75 Hz), 6.66 (2H, s), 3.84 (3H, s), 3.35-3.28 (2H, partially overlapping with H$_2$O), 2.91-2.78 (2H, m), 1.80 (3H, s), m/z=536 (M+1).

Using essentially the same procedures described in Example 61, the following compounds in Table 4 were synthesized.

TABLE 4

| EX | R$^4$ | m/z (M + H) | Chiral Source | Data |
|---|---|---|---|---|
| 62 | phenyl | 518 | Intermediate 2B | $^1$H NMR (500 MHz, DMSO-d$_6$): δ 11.23 (1 H, s), 7.64 (1 H, d, J = 3.47 Hz), 7.39-7.34 (3 H, m), 7.31 (3 H, t, J = 7.59 Hz), 6.62 (2 H, s), 3.86 (3 H, s), 3.35-3.28 (2 H, partially overlapping with H$_2$O), 2.93-2.80 (2 H, m), 1.83 (3 H, s). |
| 63 | Me | 456 | Not applicable | $^1$H NMR (500 MHz, DMSO-d$_6$): δ 11.08 (1 H, s), 7.63 (1 H, d, J = 3.48 Hz), 7.31 (1 H, d, J = 3.46 Hz), 6.86 (2 H, s), 3.84 (3 H, s), 3.35-3.27 (2 H, partially overlapping with H$_2$O), 2.91-2.78 (2 H, m), 1.38 (6 H, s). |

EXAMPLE 64

4-Amino-2′-(2,3-difluorobenzyl)-5,7′-dimethyl-5-phenyl-5H,7′H-[2,4′-bipyrrolo[2,3-d]pyrimidin]-6(7H)-one

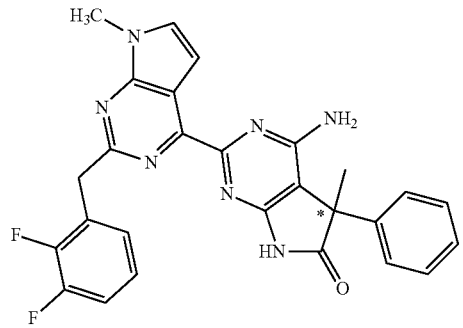 [SMILES: Cn1ccc2c(-c3nc(N)c4c(n3)NC(=O)C4(C)c3ccccc3)nc(Cc3cccc(F)c3F)nc21]

Step A: 2-(2,3-Difluorobenzyl)-7-methyl-7H-pyrrolo[2,3-d]pyrimidine-4-carboximidamide The title compound was prepared from 2-(2,3-difluorophenyl)acetic acid in place of 4,4,5,5,5-pentafluoropentanoic acid according to the procedures described in Step A to Step G of Example 60.

Step B: 4-Amino-2'-(2,3-difluorobenzyl)-5,7'-dimethyl-5-phenyl-5H,7'H-[2,4'-bipyrrolo[2,3-d]pyrimidin]-6(7H)-one The title compound was prepared from the intermediate from Step A and Intermediate 2B according to the procedure described in Step G of Example 1. $^1$H NMR (500 MHz, DMSO-$d_6$): δ 11.23 (1H, s), 7.63 (1H, d, J=3.48 Hz), 7.40-7.28 (7H, m), 7.17-7.10 (2H, m), 6.62 (2H, s), 4.44 (2H, s), 3.78 (3H, s), 1.83 (3H, s). m/z=498 (M+1).

EXAMPLE 65

4-Amino-5-methyl-2'-(3,3,4,4,4-pentafluorobutyl)-5-phenyl-5H,7'H-[2,4'-bipyrrolo[2,3-d]pyrimidin]-6(7H)-one

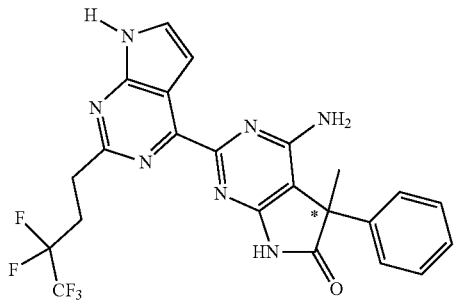 [SMILES: CC1(c2ccccc2)C(=O)Nc2nc(-c3nc(CCC(F)(F)C(F)(F)F)nc4[nH]ccc34)nc(N)c21]

Step A: 2-(3,3,4,4,4-Pentafluorobutyl)-7H-pyrrolo[2,3-d]pyrimidine-4-carbonitrile A mixture of the intermediate (0.166 g, 0.554 mmol) described in Step D of Example 60 and KCN (0.289 g, 4.43 mmol) in DMSO (4 mL) was heated at 140° C. for 4 h. The resulting mixture was partitioned between EtOAc and water. The organic phase was washed with brine, dried with MgSO$_4$, filtered, and concentrated in vacuo. The crude product was purified by silica gel chromatography using 0% to 50% EtOAc in hexanes gradient to give the title compound.

Step B: 2-(3,3,4,4,4-Pentafluorobutyl)-7H-pyrrolo[2,3-d]pyrimidine-4-carboximidamide Trimethyl aluminum (2.0 M toluene, 1.83 mL, 3.66 mmol) was added to ammonium chloride (0.15 g, 3.65 mmol) suspended in toluene (9 mL) at 0° C. The solution was then stirred at RT for 1 h. The intermediate from Step A (0.106 g, 0.365 mmol) was then added. The resulting mixture was left stirring at 100° C. for 18 h. The reaction mixture was cooled to RT and quenched with silica-gel and 1:1 MeOH-chloroform (250 mL). The resulting slurry was stirred vigorously for 30 min. The reaction mixture was filtered through a silica gel pad (1") and washed with MeOH. The filtrate was concentrated in vacuo to yield the title compound.

Step C: 4-Amino-5-methyl-2'-(3,3,4,4,4-pentafluorobutyl)-5-phenyl-5H,7'-[2,4'-bipyrrolo-[2,3-d]pyrimidin]-6(7H)-one The title compound was prepared from the intermediate from Step B and Intermediate 2B according to the procedures described in Step G of Example 1. $^1$H NMR (500 MHz, DMSO-$d_6$): δ 12.09 (1H, s), 11.24 (1H, s), 7.60 (1H, t, J=2.75 Hz), 7.40-7.28 (6H, m), 6.62 (2H, s), 3.35-3.25 (2H, m, partially overlapping with H$_2$O), 2.91-2.77 (2H, m), 1.83 (3H, s). m/z=504 (M+1).

EXAMPLE 66

4-Amino-2-(5-(2,3-difluorobenzyl)-3-methyl-3H-[1,2,3]triazolo[4,5-d]pyrimidin-7-yl)-5-(4-fluorophenyl-5-methyl-5H-pyrrolo[2,3-d]pyrimidin-6(7H)-one

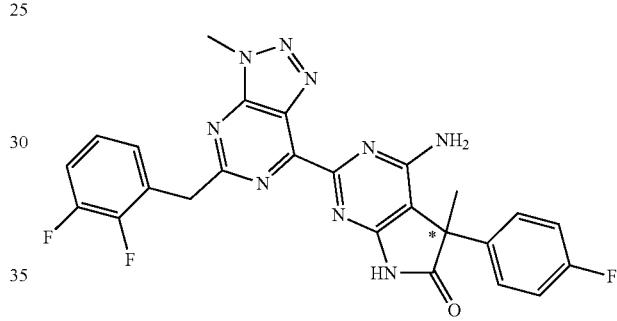

Step A:
5-Amino-1-methyl-1H-1,2,3-triazole-4-carboxamide 5-amino-1H-1,2,3-triazole-4-carboxamide was prepared according to the procedure described by Albert et. al. *J. Chem. Soc.* (C) 1969, 9, 152. To 5-amino-1H-1,2,3-triazole-4-carboxamide (0.830 g, 6.53 mmol) in MeOH (20 mL) was added NaOMe solution (1.79 mL, 7.84 mmol, 25%) dropwise at RT. The solution was then stirred for 30 min at RT and dimethyl sulfate was added (0.75 mL, 7.84 mmol). The resulting mixture was left stirring at RT for 3 h and concentrated in vacuo. The crude product was purified by silica gel chromatography using 0% to 15% MeOH in DCM gradient to give the title compound.

Step B: 5-(2,3-Difluorobenzyl)-3-methyl-3H-[1,2,3]triazolo[4,5-d]pyrimidin-7-ol

An EtOH (5 mL) solution containing the intermediate from Step A (0.98 g, 0.69 mmol), methyl 2-(2,3-difluorophenyl)acetate (259 mg, 1.39 mmol) and NaOEt (0.52 mL, 1.39 mmol, 21% solution in EtOH) was refluxed for 20 h. The resulting mixture was cooled to RT and concentrated in vacuo. The residue was suspended in water and extracted with 30% IPA/CHCl$_3$ (3×). The organic layer was concentrated in vacuo to give the title compound, which was used in the next step without further purification.

Step C: 5-(2,3-difluorobenzyl)-3-methyl-3H-[1,2,3]triazolo[4,5-d]pyrimidine-7-carboximidamide The title compound was prepared from the intermediate from Step B according to the procedures described in Step D to Step F of Example 1.

Step F: 4-Amino-2-(5-(2,3-difluorobenzyl)-3-methyl-3H-[1,2,3]triazolo[4,5-d]pyrimidin-7-yl)-5-(4-fluorophenyl)-5-methyl-5H-pyrrolo[2,3-d]pyrimidin-6(7H)-one The title compound was prepared from the intermediate from Step C and Intermediate 1B according to the procedure described in Step G of Example 1. $^1$H NMR (500 MHz, DMSO-$d_6$): δ 11.36 (1H, s), 7.32 (2H, dd, J=8.76, 5.50 Hz), 7.19 (2H, t, J=8.43 Hz), 4.57 (2H, s), 4.25 (3H, s), 1.82 (3H, s). m/z=518 (M+1).

EXAMPLE 67

4-Amino-5-(4-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one

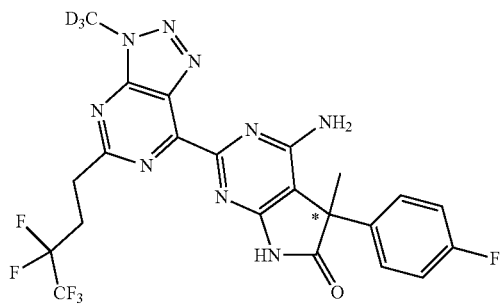 [SMILES: [2H]C([2H])([2H])n1nnc2c(-c3nc(N)c4c(n3)NC(=O)C4(C)c3ccc(F)cc3)nc(CCC(F)(F)C(F)(F)F)nc21]

Step A: 5-Amino-3-trideuteriomethyl-1H-1,2,3-triazole-4-carboxamide

The title compound was prepared from 5-amino-1H-1,2,3-triazole-4-carboxamide and dimethyl sulfate-$d_6$ according to the procedures described in Step A of Example 66.

Step B: 5-(3,3,4,4,4-Pentafluorobutyl)-3-trideuteriomethyl-3H-[1,2,3]triazolo[4,5-d]pyrimidine-7-carboximidamide The title compound was prepared from the intermediate from Step A and the intermediate described in Step B of Example 1 according to the procedures described in Steps B to C of Example 66.

Step C: 4-Amino-5-(4-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one The indicated compound was prepared from the intermediate from Step B and Intermediate 1B according to the procedure described in Step D of Example 2. $^1$H NMR (500 MHz, DMSO-$d_6$): δ 11.36 (1H, s), 7.32 (2H, dd, J=8.57, 5.35 Hz), 7.20 (2H, t, J=8.71 Hz), 6.78 (2H, s), 3.42 (2H, t, J=7.86 Hz), 2.90 (2H, t, J=9.07 Hz), 1.83 (3H, s). m/z=541 (M+1).

Using essentially the same procedures described in the Examples 66 and 67, the following compounds in Table 5 were synthesized.

TABLE 5

| EX | R$^3$ | R$^4$ | m/z (M + H) | Chiral Source | Data |
|---|---|---|---|---|---|
| 68 | Me | ⌬ (phenyl) | 523 | I-2B | $^1$H NMR (500 MHz, DMSO-$d_6$): δ 11.34 (1 H, s), 7.37 (2 H, t, J = 7.41 Hz), 7.33-7.26 (3 H, m), 6.73 (2 H, s), 3.42 (3 H, t, J = 7.86 Hz), 2.96-2.83 (2 H, m), 1.84 (3 H, s). |

TABLE 5-continued

| EX | R³ | R⁴ | m/z (M + H) | Chiral Source | Data |
|---|---|---|---|---|---|
| 69 |  | 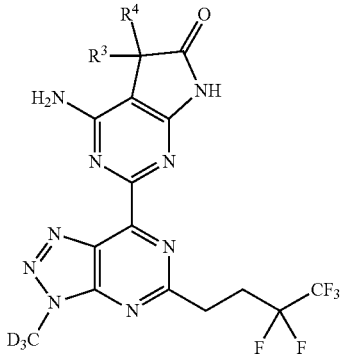 | 567 | I-16A | ¹H NMR (500 MHz, DMSO-d₆): δ 11.32 (1 H, s), 7.46 (2 H, dd, J = 8.56, 5.40 Hz), 7.22 (2 H, t, J = 8.74 Hz), 6.68 (2 H, s), 3.42 (3 H, t, J = 7.86 Hz), 2.96-2.83 (2 H, m), 2.05-1.99 (1 H, m), 0.99-0.93 (1 H, m), 0.78-0.72 (1 H, m), 0.57-0.50 (1 H, m), 0.19-0.13 (1 H, m). |
| 70 | Me |  | 557 | I-5A | ¹H NMR (500 MHz, DMSO-d₆): δ 11.37 (1 H, s), 7.43 (2 H, d, J = 8.37 Hz), 7.29 (2 H, d, J = 8.27 Hz), 6.80 (2 H, s), 3.42 (2 H, t, J = 7.86 Hz), 2.89 (2 H, t, J = 7.89 Hz), 1.82 (3 H, s). |
| 71 | Me |  | 553 | I-12B | ¹H NMR (500 MHz, DMSO-d₆): δ 11.30 (1 H, s), 7.21 (2 H, d, J = 8.43 Hz), 6.93 (2 H, d, J = 8.44 Hz), 6.70 (2 H, s), 3.75 (3 H, s), 3.43 (3 H, t, J = 7.94 Hz), 2.98-2.84 (3 H, m), 1.81 (3 H, s). |
| 72 | Me |  | 571 | I-22A | ¹H NMR (500 MHz, DMSO-d₆): δ 11.36 (1 H, s), 7.18-7.11 (2 H, m), 6.77 (2 H, s), 6.72 (1 H, ddd, J = 6.22, 4.70, 2.45 Hz), 3.86 (3 H, s), 3.42 (3 H, t, J = 7.86 Hz), 2.96-2.84 (2 H, m), 1.83 (3 H, s). |
| 73 | Me |  | 575 | I-21A | ¹H NMR (400 MHz, CDCl₃): δ 8.86 (1 H, br s), 7.55 (1 H, t, J = 8.0 Hz), 7.32-1.29 (1 H, m), 7.16-7.13 (1 H, m), 5.08 (2 H, r s), 3.63 (2 H, d, J = 8.0 Hz), 2.92-2.79 (2 H, m), 1.92 (3 H, s). |

Biological Assays: Cell-Based sGC Functional Assay (CASA Assay)

sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods:

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 μg/mL penicillin/streptomycin, 0.5 mg/mL hygromycin and 0.25 mg/mL G418. The cells were then cryopreserved in LN2. On the day of the assay, cells were thawed and resuspended in EBSS Assay Buffer (EAB, Sigma, E3024) supplemented with 5 mM MgCl₂, 10 mM HEPES (4-(2-hydroxyethyl)piperazine-1-ethanesulfonic acid) and 0.05% BSA (bovine serum albumin) and cell density was then adjusted to 4×105/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were incubated with compounds in the presence and absence of 1 μM of Diethylenetriamine/nitric oxide adduct (DETA-NO; Sigma, 17018) for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation) of the published sGC-HDA Compound A:

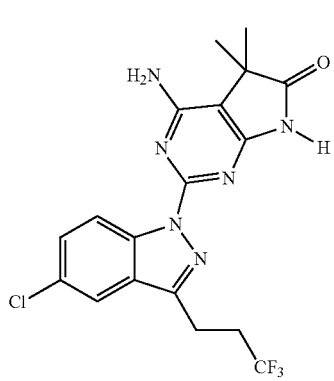

Compound A (Example 1 in WO 2010/065275, published Jun. 10, 2010). The test compounds' activity was then expressed as a percentage of Compound A, the standard in every experiment. This percent activation was calculated either in the presence or absence of DETA-NO which was then plotted. IP and maximum fold induction was derived using ADA analysis software for 4P fit.

Most preferred compounds had an IP of less than or equal to about 500 nM. Data for the compounds of the Examples is provided in Table 6.

TABLE 6

| EX | IP (nM) | % ACT |
|---|---|---|
| 1 | 40 | 101 |
| 2 | 32 | 97 |
| 3 | 119 | 132 |
| 4 | 130 | 108 |
| 5 | 53 | 122 |
| 6 | 157 | 127 |
| 7 | 85 | 110 |
| 8 | 341 | 109 |
| 9 | 46 | 110 |
| 10 | 197 | 116 |
| 11 | 146 | 121 |
| 12 | 285 | 75 |
| 13 | 40 | 101 |
| 14 | 21 | 110 |
| 15 | 52 | 113 |
| 16 | 15 | 112 |
| 17 | 286 | 104 |
| 18 | 171 | 122 |
| 19 | 53 | 119 |
| 20 | 143 | 123 |
| 21 | 92 | 106 |
| 22 | 46 | 128 |
| 23 | 49 | 106 |
| 24 | 105 | 120 |
| 25 | 49 | 80 |
| 26 | 830 | 93 |
| 27 | 602 | 98 |
| 28 | 53 | 112 |
| 29 | 135 | 131 |
| 30 | 245 | 84 |
| 31 | 190 | 132 |
| 32 | 52 | 131 |
| 33 | 53 | 112 |
| 34 | 143 | 122 |

TABLE 6-continued

| EX | IP (nM) | % ACT |
|---|---|---|
| 35 | 62 | 107 |
| 36 | 878 | 121 |
| 37 | 540 | 93 |
| 38 | 648 | 112 |
| 39 | 43 | 104 |
| 40 | 55 | 121 |
| 41 | 77 | 100 |
| 42 | 111 | 134 |
| 43 | 209 | 110 |
| 44 | 111 | 88 |
| 45 | 716 | 138 |
| 46 | 90 | 91 |
| 47 | 30 | 95 |
| 48 | 664 | 93 |
| 49 | 248 | 105 |
| 50 | 1236 | 101 |
| 51 | 746 | 109 |
| 52 | 614 | 92 |
| 53 | 869 | 104 |
| 54 | 87 | 118 |
| 55 | 119 | 118 |
| 56 | 44 | 104 |
| 57 | 113 | 139 |
| 58 | 632 | 70 |
| 59 | 299 | 94 |
| 60 | 47 | 106 |
| 61 | 61 | 91 |
| 62 | 19 | 92 |
| 63 | 502 | 76 |
| 64 | 12 | 83 |
| 65 | 255 | 102 |
| 66 | 156 | 69 |
| 67 | 1069 | 114 |
| 68 | 403 | 107 |
| 69 | 1137 | 98 |
| 70 | 327 | 95 |
| 71 | 594 | 67 |
| 72 | 424 | 66 |
| 73 | 429 | 97 |

Acute Efficacy in Spontaneously Hypertensive Rats (SHR)

Spontaneously hypertensive rats (SHR, male, Charles River) were implanted with DSI TA 11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 min. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 h light-dark cycle.

Maximum peak decreases of systolic blood pressure (SBP) in SHR at a particular P.O. dose (mpk milligrams per kilogram) for the following Example compounds are provided. Category A=SBP in SHRs<25 mmHg; Category B=SBP in SHRs 25-40 mmHg; Category C=SBP in SHRs>40 mmHg.

TABLE 7

| EX | Dose (P.O. mpk) | Category |
|----|-----------------|----------|
| 1  | 1   | C |
| 2  | 1   | C |
| 4  | 3   | C |
| 6  | 3   | A |
| 7  | 3   | B |
| 9  | 1   | C |
| 12 | 1   | B |
| 28 | 1   | C |
| 31 | 0.3 | B |
| 32 | 1   | A |
| 61 | 1   | A |
| 62 | 1   | A |
| 67 | 1   | A |
| 69 | 3   | B |
| 71 | 1   | A |
| 73 | 3   | A |

What is claimed is:

1. A compound having structural Formula I:

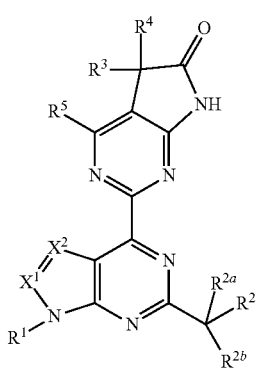

or a pharmaceutically acceptable salt thereof wherein:
$X^1$ and $X^2$ are each independently CR or N;
R is —H, halo or cyclopropyl;
$R^1$ is —H or —$C_{1-6}$ alkyl unsubstituted or substituted with one to three of —F;
$R^2$ is (a) —$C_{1-6}$alkyl unsubstituted or substituted with
 (i) one to six of —F,
 (ii) —$C_{3-6}$cycloalkyl unsubstituted or substituted with one to three of —F or
 (iii) phenyl unsubstituted or independently substituted at each occurrence with one to three of halo, —CN, —$CH_3$ or —$OCH_3$,
(b) —$C_{3-6}$cycloalkyl unsubstituted or substituted with one to three of —F, or
(c) phenyl unsubstituted or independently substituted at each occurrence with one to three of halo, —CN, —$CH_3$ or —$OCH_3$;
$R^{2a}$ is —H or —$C_{1-3}$ alkyl unsubstituted or substituted with one to three of —F;
$R^{2b}$ is —H or —$C_{1-3}$alkyl unsubstituted or substituted with one to three of —F;
or $R^{2b}$ is —H and $R^2$ and $R^{2a}$ are joined together with the carbon to which they are both attached to represent
 (a) —$C_{3-6}$cycloalkyl unsubstituted or substituted with one to three of —F, or
 (b) a 4 to 6 membered heterocycle comprised of carbons and one or two heteroatoms independently selected from N, O or S, wherein the heterocycle is unsubstituted or independently substituted at each occurrence with one to three of halo, —CN, —$CH_3$ or —$OCH_3$;
$R^3$ is —$C_{1-6}$alkyl or —$C_{3-6}$cycloalkyl;
$R^4$ is (a) —$C_{1-6}$alkyl,
 (b) —$OC_{1-6}$alkyl
 (c) —$C_{2-6}$alkynyl,
 (d) —$C_{3-6}$cycloalkyl,
 (e) —COO—$C_{1-6}$alkyl
 (f) —$NHR^a$,
 (g) —NH—C(O)—$R^a$,
 (h) —C(O)$NHR^a$,
 (i) —CN,
 (j) phenyl unsubstituted or substituted with one to three substituents independently selected at each occurrence from halo, —$C_{1-6}$alkyl, —$OC_{1-6}$alkyl, —OH or —CN; or
 (k) phenyl substituted with a 5 or 6 membered heteroaryl comprised of carbon atoms, one to three of N, and zero or one of O, wherein the heteroaryl is unsubstituted or substituted with —$C_{1-3}$ alkyl;
$R^a$ is (a) —H, (b) —$C_{1-6}$alkyl unsubstituted or substituted with one or more substituents independently selected from —OH, one to three of —F,
 (c) —$C_{1-3}$alkyl-$C_{3-6}$cycloalkyl, (d) —$C_{3-6}$cycloalkyl, or (e) a 5 or 6 membered heteroaryl comprised of carbon atoms and one to three heteroatoms independently selected from N, O and S, wherein the heteroaryl is unsubstituted or substituted with —$C_{1-3}$alkyl;
$R^5$ is —H, —$OR^6$ or —$NHR^6$; and
$R^6$ is —H, —$C_{1-6}$alkyl or —$C_{3-6}$ cycloalkyl.

2. The compound of claim 1 or a pharmaceutically acceptable salt thereof wherein: $X^1$ and $X^2$ are each independently CH or N,
$R^1$ is —H or —$C_{1-3}$alkyl;
$R^3$ is —$C_{1-6}$alkyl or —$C_{3-6}$cycloalkyl; and
$R^5$ is —H, —OH or —$NH_2$.

3. The compound of claim 1 or a pharmaceutically acceptable salt thereof wherein:
$X^1$ and $X^2$ are each independently CH or N,
$R^1$ is —H or —$C_{1-3}$alkyl;
$R^2$ is (a) —$C_{1-6}$alkyl substituted with
 (i) one to six of —F,
 (ii) —$C_{3-6}$cycloalkyl substituted with one to three of —F or
 (iii) phenyl substituted with one to three of —F,
(b) —$C_{3-6}$cycloalkyl substituted with one to three of —F, or
(c) phenyl substituted with one to three of —F;
$R^3$ is —$C_{1-6}$alkyl or —$C_{3-6}$cycloalkyl;
$R^4$ is (a) —$C_{1-6}$alkyl,
 (b) —$OC_{1-6}$alkyl
 (c) —$C_{2-3}$ alkynyl,
 (d) —$C_{3-6}$cycloalkyl,
 (e) —COO—$C_{1-3}$ alkyl,
 (f) —$NHR^a$,
 (g) —NH—C(O)—$R^a$,
 (h) —C(O)$NHR^a$,
 (i) —CN,
 (j) phenyl unsubstituted or substituted with one to three substituents independently selected at each occurrence from halo, —$C_{1-3}$alkyl, —$OC_{1-3}$alkyl, —OH or —CN; or
 (k) phenyl substituted with a 5 or 6 membered heteroaryl comprised of carbon atoms, one to three of N, and zero or one of O, wherein the heteroaryl is unsubstituted or substituted with —$C_{1-3}$ alkyl;

$R^a$ is (a) —H,
(b) —$C_{1-6}$alkyl unsubstituted or substituted with one or more substituents independently selected from —OH and one to three of —F,
(c) —$C_{1-3}$ alkyl-$C_{3-6}$cycloalkyl,
(d) —$C_{3-6}$cycloalkyl, or
(e) 5 or 6 membered heteroaryl comprised of carbon atoms and one to three of N, wherein the heteroaryl is unsubstituted or substituted with —$C_{1-3}$alkyl; and $R^5$ is —H, —OH or —$NH_2$.

4. The compound of claim 1 or a pharmaceutically acceptable salt thereof wherein $R^2$ is
(a) —$C_{1-6}$alkyl substituted with
(i) one to six of —F,
(ii) —$C_{3-6}$cycloalkyl substituted with one to three of —F, or
(iii) phenyl substituted with one to three of —F,
(b) —$C_{3-6}$cycloalkyl substituted with one to three of —F, or
(c) phenyl substituted with one to three of —F.

5. The compound of claim 1 or a pharmaceutically acceptable salt thereof wherein is $R^3$ is —$C_{1-3}$alkyl or cyclopropyl.

6. The compound of claim 1 or a pharmaceutically acceptable salt thereof wherein is $R^4$ is
(a) —$C_{1-4}$alkyl,
(b) —$OC_{1-4}$alkyl,
(c) —$C_{2-3}$alkynyl,
(d) —$C_{3-6}$cycloalkyl,
(e) —COO—$C_{1-3}$ alkyl
(f) —$NHR^a$,
(g) —NH—C(O)—$R^a$,
(h) —C(O)$NHR^a$,
(i) —CN,
(j) phenyl unsubstituted or substituted with one to three substituents independently selected at each occurrence from —F, —Br, —$C_{1-3}$alkyl, —$OC_{1-3}$alkyl, —OH or —CN; or
(k) phenyl substituted with pyridyl, oxadiazolyl or pyrazolyl.

7. The compound of claim 1 or a pharmaceutically acceptable salt thereof wherein $R^a$ is (a) —H, (b) —$C_{1-4}$ alkyl unsubstituted or substituted with one or more substituents independently selected from —OH and one to three of —F, (c) —$CH_2$—$C_{3-6}$cycloalkyl, (d) —$C_{3-6}$ cycloalkyl, or (e) a heteroaryl which is pyridyl or pyrazolyl, wherein the heteroaryl is unsubstituted or substituted with —$C_{1-3}$alkyl.

8. The compound of claim 1 or a pharmaceutically acceptable salt thereof wherein $R^1$ is —H, —$CH_3$, —$CD_3$, —$CH_2CH_3$ or -$CD_2CD_3$.

9. The compound of claim 1 or a pharmaceutically acceptable salt thereof wherein $R^5$ is —$NH_2$.

10. The compound of claim 1, having the structural Formula Ia or a pharmaceutically acceptable salt thereof:

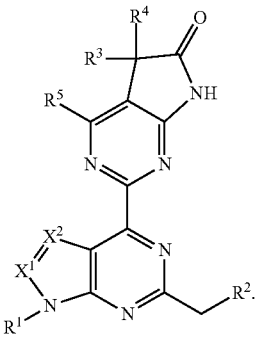

Ia

11. The compound of claim 1, having the structural Formula Ib or a pharmaceutically acceptable salt thereof:

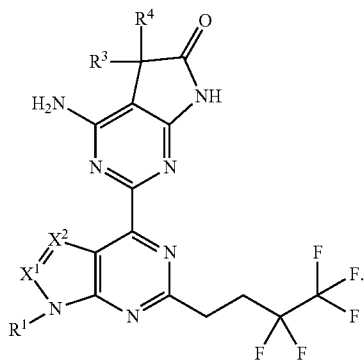

Ib

12. The compound of claim 1, which is:
4-Amino-5-methyl-2-(1-methyl-6-(3,3,4,4,4-pentafluorobutyl)-1H-pyrazolo[3,4-d]pyrimidin-4-yl)-5-phenyl-5H-pyrrolo[2,3-d]pyrimidin-6(7H)-one;
4-Amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;
4-Amino-5-methyl-2-(1-methyl-6-(4,4,4-trifluorobutyl)-1H-pyrazolo[3,4-d]pyrimidin-4-yl)-5-phenyl-5H-pyrrolo[2,3-d]pyrimidin-6(7H)-one;
4-Amino-5-methyl-2-(1-methyl-6-(3,3,3-trifluoropropyl)-1H-pyrazolo[3,4-d]pyrimidin-4-yl)-5-phenyl-5H-pyrrolo[2,3-d]pyrimidin-6(7H)-one;
4-Amino-2-(6-((3,3-difluorocyclobutyl)methyl)-1-methyl-1H-pyrazolo[3,4-d]pyrimidin-4-yl)-5-(4-fluorophenyl)-5-methyl-5H-pyrrolo[2,3-d]pyrimidin-6(7H)-one;
4-Amino-2-(6-(2,3-difluorobenzyl)-1-methyl-1H-pyrazolo[3,4-d]pyrimidin-4-yl)-5-(4-fluorophenyl)-5-methyl-5H-pyrrolo[2,3-d]pyrimidin-6(7H)-one;
4-Amino-2-(1-ethyl-6-(3,3,4,4,4-pentafluorobutyl)-1H-pyrazolo[3,4-d]pyrimidin-4-yl)-5-methyl-5-phenyl-5H-pyrrolo[2,3-d]pyrimidin-6(7H)-one;
4-Amino-5-(4-fluorophenyl)-5-methyl-2-(6-(3,3,4,4,4-pentafluorobutyl)-1H-pyrazolo[3,4-d]pyrimidin-4-yl)-5H-pyrrolo[2,3-d]pyrimidin-6(7H)-one;
4-Amino-5-(4-fluorophenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-(4-bromophenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-(4-fluorophenyl)-5-methyl-2-(1-methyl-6-(3,3,3-trifluoropropyl)-1H-pyrazolo[3,4-d]pyrimidin-4-yl)-5H-pyrrolo[2,3-d]pyrimidin-6(7H)-one;

4-Amino-5,5-dimethyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-methyl-2-(6-(3,3,4,4,4-pentafluorobutyl)-1-trideuteriomethyl-1H-pyrazolo[3,4-d]pyrimidin-4-yl)-5-phenyl-5H-pyrrolo[2,3-d]pyrimidin-6(7H)-one;

4-Amino-5-(3-methoxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-(3-fluoro-4-methoxyphenyl)-5-methyl-2-(1-methyl-6-(4,4,4-trifluorobutyl)-1H-pyrazolo[3,4-d]pyrimidin-4-yl)-5H-pyrrolo[2,3-d]pyrimidin-6(7H)-one;

4-Amino-5-(3-fluoro-4-methoxyphenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-cyclopropyl-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-cyclohexyl-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-2-(1-ethyl-6-(3,3,4,4,4-pentafluorobutyl)-1H-pyrazolo[3,4-d]pyrimidin-4-yl)-5-(4-fluorophenyl)-5-methyl-5H-pyrrolo[2,3-d]pyrimidin-6(7H)-one;

4-Amino-2-(1-ethyl-6-(4,4,4-trifluorobutyl)-1H-pyrazolo[3,4-d]pyrimidin-4-yl)-5-(4-fluorophenyl)-5-methyl-5H-pyrrolo[2,3-d]pyrimidin-6(7H)-one;

4-Amino-5-ethynyl-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-ethynyl-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-ethyl-5-ethynyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-cyclopropyl-5-ethynyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-butyl-5-cyclopropyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

Ethyl 4-amino-5-cyclopropyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxylate;

Ethyl 4-amino-5-cyclopropyl-2-(1-methyl-6-(4,4,4-trifluorobutyl)-1H-pyrazolo[3,4-d]pyrimidin-4-yl)-6-oxo-6,7-dihydro-5H-pyrrolo[2,3-d]pyrimidine-5-carboxylate;

4-Amino-N,5-dicyclopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-5-cyclopropyl-N-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-N,5-dicyclopropyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-5-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-5-isopropyl-2-(6-(3,3,4,4,4-pentafluorobutyl)-1-trideuteriomethyl-1H-pyrazolo[3,4-d]pyrimidin-4-yl)-6-oxo-6,7-dihydro-5N-pyrrolo[2,3-d]pyrimidine-5-carboxamide;

4-Amino-5-ethyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-5-isopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-N,5-dicyclopropyl-2-(1-ethyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide;

4-Amino-N-ethyl-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-2-(6-(2,3-difluorobenzyl)-1-methyl-1H-pyrazolo[3,4-d]pyrimidin-4-yl)-5-methyl-6-oxo-6,7-dihydro-5H-pyrrolo[2,3-d]pyrimidine-5-carboxamide;

4-Amino-5-cyclopropyl-2-(6-(3,3,4,4,4-pentafluorobutyl)-1-trideuteriomethyl-1H-pyrazolo[3,4-d]pyrimidin-4-yl)-6-oxo-N-(pyridin-2-yl)-6,7-dihydro-5H-pyrrolo[2,3-d]pyrimidine-5-carboxamide;

4-amino-5-methyl-N-(1-methyl-1H-pyrazol-4-yl)-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-5-(4-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-(3-hydroxyphenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

5-(4-(1,3,4-Oxadiazol-2-yl)phenyl)-4-amino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-methyl-5-(4-(1-methyl-1H-pyrazol-4-yl)phenyl)-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-(4-Amino-5-methyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidin-5-yl)benzonitrile;

5-(4-Fluorophenyl)-4-hydroxy-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carbonitrile;

4,5-Diamino-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)picolinamide;

N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)-2-cyclopropylacetamide;

N-(4-Amino-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidin-5-yl)cyclopropanecarboxamide;

4-Amino-5-((cyclopropylmethyl)amino)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-(isopropylamino)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-methoxy-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5-methyl-5-trideuteriomethoxy-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-2-(3-chloro-1-methyl-6-(3,3,4,4,4-pentafluorobutyl)-1H-pyrazolo[3,4-d]pyrimidin-4-yl)-5-(4-fluorophenyl)-5-methyl-5H-pyrrolo[2,3-d]pyrimidin-6(7H)-one;

4-Amino-2-(3-cyclopropyl-6-(3,3,4,4,4-pentafluorobutyl)-1-trideuteriomethyl-1H-pyrazolo[3,4-d]pyrimidin-4-yl)-5-(4-fluorophenyl)-5-methyl-5H-pyrrolo[2,3-d]pyrimidin-6(7H)-one;

4-Amino-5-methyl-2'-(3,3,4,4,4-pentafluorobutyl)-5-phenyl-7'-trideuteriomethyl-5H,7'H-[2,4'-bipyrrolo[2,3-d]pyrimidin]-6(7H)-one;

4-Amino-5-(4-fluorophenyl)-5,7'-dimethyl-2'-(3,3,4,4,4-pentafluorobutyl)-5H,7'H-[2,4'-bipyrrolo[2,3-d]pyrimidin]-6(7H)-one;

4-Amino-5,7'-dimethyl-2'-(3,3,4,4,4-pentafluorobutyl)-5-phenyl-5H,7'H-[2,4'-bipyrrolo[2,3-d]pyrimidin]-6(7H)-one;

4-Amino-5,5,7'-trimethyl-2'-(3,3,4,4,4-pentafluorobutyl)-5H,7'H-[2,4'-bipyrrolo[2,3-d]pyrimidin]-6(7H)-one;

4-Amino-2'-(2,3-difluorobenzyl)-5,7'-dimethyl-5-phenyl-5H,7'H-[2,4'-bipyrrolo[2,3-d]pyrimidin]-6(7H)-one;

4-Amino-5-methyl-2'-(3,3,4,4,4-pentafluorobutyl)-5-phenyl-5H,7'H-[2,4'-bipyrrolo[2,3-d]pyrimidin]-6(7H)-one;

4-Amino-2-(5-(2,3-difluorobenzyl)-3-methyl-3H-[1,2,3]triazolo[4,5-d]pyrimidin-7-yl)-5-(4-fluorophenyl)-5-methyl-5H-pyrrolo[2,3-d]pyrimidin-6(7H)-one;

4-Amino-5-(4-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-methyl-2-(5-(3,3,4,4,4-pentafluorobutyl-3-trideuteriomethyl)-3H-[1,2,3]triazolo[4,5-d]pyrimidin-7-yl)-5-phenyl-5H-pyrrolo[2,3-d]pyrimidin-6(7H)-one;

4-Amino-5-cyclopropyl-5-(4-fluorophenyl)-2-(5-(3,3,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-(4-chlorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-(4-methoxyphenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-(4-fluoro-3-methoxyphenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-(4-chloro-2-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

or a pharmaceutically acceptable salt of each of the foregoing compounds.

13. The compound of claim 1, which is:

4-Amino-5-methyl-2-(1-methyl-6-(3,3,4,4,4-pentafluorobutyl)-1H-pyrazolo[3,4-d]pyrimidin-4-yl)-5-phenyl-5H-pyrrolo[2,3-d]pyrimidin-6(7H)-one;

4-Amino-5-(4-fluorophenyl)-5-methyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-5-methyl-2-(1-methyl-6-(3,3,3-trifluoropropyl)-1H-pyrazolo[3,4-d]pyrimidin-4-yl)-5-phenyl-5H-pyrrolo[2,3-d]pyrimidin-6(7H)-one;

4-Amino-2-(6-(2,3-difluorobenzyl)-1-methyl-1H-pyrazolo[3,4-d]pyrimidin-4-yl)-5-(4-fluorophenyl)-5-methyl-5H-pyrrolo[2,3-d]pyrimidin-6(7H)-one;

4-Amino-2-(1-ethyl-6-(3,3,4,4,4-pentafluorobutyl)-1H-pyrazolo[3,4-d]pyrimidin-4-yl)-5-methyl-5-phenyl-5H-pyrrolo[2,3-d]pyrimidin-6(7H)-one;

4-Amino-5-(4-fluorophenyl)-5-methyl-2-(1-methyl-6-(3,3,4,4,4-pentafluorobutyl)-1H-pyrazolo[3,4-d]pyrimidin-4-yl)-5H-pyrrolo[2,3-d]pyrimidin-6(7H)-one;

4-Amino-5,5-dimethyl-2-(6-(3,3,4,4,4-pentafluorobutyl)-1-trideuteriomethyl-1H-pyrazolo[3,4-d]pyrimidin-4-yl)-5H-pyrrolo[2,3-d]pyrimidin-6(7H)-one;

4-Amino-N,5-dicyclopropyl-2-(6-(3,3,4,4,4-pentafluorobutyl)-1-trideuteriomethyl-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-5-methyl-2-(1-methyl-6-(3,3,4,4,4-pentafluorobutyl)-1H-pyrazolo[3,4-d]pyrimidin-4-yl)-6-oxo-6,7-dihydro-5H-pyrrolo[2,3-d]pyrimidine-5-carboxamide;

4-Amino-N-cyclopropyl-5-methyl-2-(6-(3,3,4,4,4-pentafluorobutyl)-1-trideuteriomethyl-1H-pyrazolo[3,4-d]

pyrimidin-4-yl)-6-oxo-6,7-dihydro-5H-pyrrolo[2,3-d]pyrimidine-5-carboxamide;

4-Amino-5-(4-fluorophenyl)-5,7'-dimethyl-2'-(3,3,4,4,4-pentafluorobutyl)-5H,7'H-[2,4'-bipyrrolo[2,3-d]pyrimidin]-6(7H)-one;

4-Amino-5,7'-dimethyl-2'-(3,3,4,4,4-pentafluorobutyl)-5-phenyl-5H,7'H-[2,4'-bipyrrolo[2,3-d]pyrimidin]-6(7H)-one;

4-Amino-5-(4-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-cyclopropyl-5-(4-fluorophenyl)-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-(4-methoxyphenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

4-Amino-5-(4-chloro-2-fluorophenyl)-5-methyl-2-(5-(3,3,4,4,4-pentafluorobutyl-3-trideuteriomethyl)-3H-[1,2,3]triazolo[4,5-d]pyrimidin-7-yl)-5H-pyrrolo[2,3-d]pyrimidin-6(7H)-one;

or a pharmaceutically acceptable salt of each of the foregoing compounds.

14. A method for activating soluble guanylate cyclase comprising the step of administering an amount efficacious therefore of the compound of claim 1 or a pharmaceutically acceptable salt thereof.

15. A method for the treatment of hypertension comprising administering a therapeutically effective amount of the compound of claim 1, or a pharmaceutically acceptable salt thereof, to a patient in need thereof.

16. A method for the treatment of heart failure comprising administering a therapeutically effective amount of the compound of claim 1, or a pharmaceutically acceptable salt thereof, to a patient in need thereof.

17. A pharmaceutical composition comprising the compound of claim 1, or a pharmaceutically acceptable salt thereof, and a pharmaceutically acceptable carrier.

18. The pharmaceutical composition of claim 17 further comprising one or more additional active agents selected from an angiotensin converting enzyme inhibitor, an angiotensin II receptor antagonist, a neutral endopeptidase inhibitor, an aldosterone antagonist, a renin inhibitor, an endothelin receptors antagonist, an aldosterone synthase inhibitor, a phosphodiesterase-5 inhibitor, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent or a metabolic altering agent.

* * * * *